(12) United States Patent
Botella Mesa et al.

(10) Patent No.: US 7,745,603 B1
(45) Date of Patent: Jun. 29, 2010

(54) PLANT PROMOTER AND USES THEREFOR

(75) Inventors: Jose Botella Mesa, Kenmore (AU); Christopher Ian Cazzonelli, Malanda (AU)

(73) Assignee: The University of Queensland, St. Lucia, Queensland (AU)

( * ) Notice: Subject to any disclaimer, the term of this patent is extended or adjusted under 35 U.S.C. 154(b) by 0 days.

(21) Appl. No.: 09/763,957

(22) PCT Filed: Aug. 31, 1999

(86) PCT No.: PCT/AU99/00705

§ 371 (c)(1),
(2), (4) Date: Jun. 18, 2001

(87) PCT Pub. No.: WO00/12714

PCT Pub. Date: Mar. 9, 2000

(30) Foreign Application Priority Data

Aug. 31, 1998 (AU) ................................. PP5572

(51) Int. Cl.
C12N 15/09 (2006.01)
C12N 15/63 (2006.01)
C12N 15/67 (2006.01)
C12N 15/82 (2006.01)

(52) U.S. Cl. .................. 536/24.1; 536/23.1; 435/320.1; 435/69.1; 435/91.2; 435/91.4

(58) Field of Classification Search ................ 435/69.1, 435/321.1, 172.3, 419, 325, 252.3, 468, 411, 435/24.33, 320.1, 410, 430; 800/283, 286, 800/287, 288; 536/24.1, 24.3
See application file for complete search history.

(56) References Cited

U.S. PATENT DOCUMENTS

| 5,523,221 A | 6/1996 | Weiner |
| 5,702,933 A | 12/1997 | Klee et al. |
| 5,723,766 A | 3/1998 | Theologis et al. |
| 5,750,667 A | 5/1998 | Wickens et al. |
| 5,756,343 A | 5/1998 | Wu et al. |
| 5,767,376 A | 6/1998 | Stiles et al. |

FOREIGN PATENT DOCUMENTS

| WO | WO 94/08449 | * 10/1993 |
| WO | WO 96/35792 | 11/1996 |
| WO | WO 97/11166 | 3/1997 |
| WO | WO 97/27308 | 7/1997 |
| WO | WO 98/06852 | 2/1998 |
| WO | WO 98/14465 | 4/1998 |
| WO | WO 98/42445 | 10/1998 |

OTHER PUBLICATIONS

N Resnick et al., Medical Sciences, "Platelet-derived growth factor B chain promoter contains a cis-acting fluid shear-stress-responsive element," May 1993, vol. 90, pp. 4591-4595.*
B Blume et al., The Plant Journal, "Expression of ACC oxidase promoter-GUS fusions in tomato and *Nicotiana plumbaginifolia* regulated by developmental and environmental stimuli," 1997, 12(4), 731-746.*
Knox et al, In Vivo Stimulation of a Chimeric Promoter by Binding Sites for Nuclear Factor I, Molecular and Cellular Biology, Jun. 1991, pp. 2946-2951.*
Protein structure prediction-Wikipedia, downloaded Oct. 14, 2005.*
Tertiary structures- Biology Pages, downloaded Oct. 14, 2005..*
Smith et al, Surface point mutations that significantly alter the structure and stability of a protein's denatured state, Protein Science, 1996, vol. 5, pp. 2009-2019.*
Botella et al., Plant Molecular Biology, vol. 18, pp. 793-797, 1992.
Botella et al., Plant Molecular Biology, vol. 20, pp. 425-436, 1992.
Botella et al., Proc. Natl. Acad. Sci. USA, vol. 92, pp. 1595-1598, 1995.
Yoon et al., Plant Cell Physiol, vol. 40(4), pp. 431-438, 1999.
Liu et al., EMBL Accession No. X67100.
Peck et al., Plant Journal, vol. 14(5), pp. 573-581, 1998.
Peck et al., Plant Molecular Biology, vol. 28(2), pp. 293-301, 1995.

* cited by examiner

*Primary Examiner*—Maria Marvich
(74) *Attorney, Agent, or Firm*—Knobbe Martens Olson & Bear LLP

(57) ABSTRACT

The present invention relates generally to a novel plant promoter. More particularly, the present invention provides a plant promoter capable of induction by physical and/or environmental stimuli in cells in which the promoter is indigenous and, in the absence of any negative regulatory mechanism, is capable of constitutive expression in cells in which the promoter is non-indigenous. The present invention is further directed to derivatives of the subject promoter including modular forms of the promoter which are, for example, inducible by different physical and environmental stimuli or which are constitutively expressed. The promoter of the present invention has a range of uses including directing expression of genes conferring useful traits on plants.

25 Claims, 28 Drawing Sheets

AIM-1 OLIGONUCLEOTIDES

-Oligonucleotide primers (SEQ ID NOS:4-9) used during Long Distance Inverse PCR
-Oligo's bind to regions of AIM-I (Mung bean ACC Synthase)

NSE-1 to NSE-6 correspond to SEQ ID NOS:4-9, respectively.

*NSE-1*
    5' -GCGGAT↓CCATCTTGGACAACAAGGGAGTT - 3'
    29'omer
    Tm = 68

*NSE-2*
    5' -TAGGATC↓CAGAAAGACACTGAGAACCGTGG- 3'
    30'omer
    Tm = 70

*NSE-3*
    5' -ACGGATCC↓GGTGTATGTGGTTAGAGTGTG- 3'
    29'omer
    Tm = 62

*NSE-4*
    5' -CAGGATC↓CAGACATAGAGTGTGACCGCAA- 3'
    29'omer
    Tm = 66

*NSE-5*
5' -ATCGATCATATGAGCTCTAGACCCGGGCTGCAGGATCC↓GGTGTATGTGGTTAGAGTGTG- 3'
59'omer
Tm = 62
note: NSE-5 is identical to NSE-3 except different restriction enzyme sites have been incorporated
(ie. 5'-Cla I, Nde I, Sac I, Xba I, Sma I, Pst I & Bam HI-3')

*NSE-6*
5' -CCGCGGAGATCTATCGATCTCGAGAATTCAAGCTT ↓ CAGACATAGAGTGTGACCGCAA-3'
57'omer
Tm = 66
note: NSE-6 is identical to NSE-4 except different restriction enzyme sites have been incorporated
(ie. 5'-Sac II, Bgl II, Cla I, Xho I, Eco RI, & Hind III-3')

FIGURE 1

Figure 4 corresponds to SEQ ID NO:3 pGEL-1 2.5Kb Promoter Fragment
Length: 2470

```
   1  TTACAGATAC ACAGAATCAG ACGACACATC TACTTTAATA ACAGAAAAAT
  51  AATAAGTGTC GGAGATTATG GTACGACAAG ATGAAATGTT TTTATATGGT
 101  TGAGATTATT TTGGTCTGTT GTTGGAAGTT TCACGAATCA TGATTTTGAT
 151  TTTACGTATT AAAAAATGAA AAGTTGAATC ATGCATTTTA TCTAGAAGCT
 201  GGGAACTGAA CCAAAAAAAT AGCCAGTTGA ACAACTGCAG TATTTGTAGG
 251  CGTATTCATT TCTCCTTTCC TACAATAATC CTTGGTTGCT CTTTATCGGA
 301  AAAAAACCAA AAGCAATAGC TACTCTGTAA GGTCCTCGAT TGCCGACAAG
 351  AACATCACAT GCGTGCTGTC GAAGAACACA TAATTTTGAG GTTGAAGCTC
 401  ACGTGCGAGT TTTGCATATT TTTAGGTTAT GTGTACACGT ATGGAGTGAG
 451  TTCCGCGTAT ATAGTGTAGG TAGTTGAGTG GCTGAGTAGC GAGTGAATCA
 501  GGTAACACTA TCTTTTCAAG CCACCTAATT AAGGGATTTA ATGTTCATGC
 551  AACTGTTCTT CGCTAACTAA GGCCCCACTT ACCTTTATAA TATTCTCTCT
 601  AACTCCGGGC TTTTGGTAAG TACAACTTTT CTACTCTTAT TTAATGGAGG
 651  GATTATTTTT TCCATATACC AATTAATTTA TTTTTTAATT TATGCATTTT
 701  GATCTTATAT TAAAACAATT ATGGTATGGA TTAAGTCGTA TATCGGTGAC
 751  AATTGAAGTT TTCCTCAAGT TTAGCCATTT TTATGAAATT AAACTTAATC
 801  ACTACTATTA GGTAAATTCA TATGTATCAT TAACAATTTC AATGTGAGTT
 851  CAATTTTACC CAAGATTTGA AAGTTGTTGT CAACTTCTGT TAACTAAAGT
 901  TGTATTATAA GGTTGACGAC TTTAACCTAA ATCTATTTTG AATTGAAGGG
 951  GTTGATGACT TCAGCTTTAA AATAATTCAA CTAAAGTTCT AGACTACATT
1001  GGAGATTTTA GTGTTCATAA AATTTTAGAA AAAGGCTGAG TTAAAGTTAT
1051  GAAAAGATT GGTGACTATT CAATTAATTA GTTGTGAATT GATGACAAAT
1101  ATTTCATGAG CATAACCAAT CAGAGAAATA CCACCTCGAC CGACTACAAC
1151  AATCTCAATG TTAATTAATG AAGCATTGTA GTATAAGGAG TCTAGAATAA
1201  ATTTCTTAAA TATTAGAGGA AAACTATTTT TAAAAAATTA CAAGAAAAGT
1251  TTGATCTATA ACCTCTTTAA ACTTTAAATT ATCTAACAAT TTTCTTATGA
```

FIGURE 4(i)

```
1301  CTCACATTGT GTTGATAGGG TGATTTTGTC AAAATATATG TCTATTTTAT
1351  ACTAGTATGA TTTGTCTGCG AATTATATAT AGTATTAACT TGGAGAAATG
1401  ATTGCCTAAT AAGTTATAAA AAAGGAGAAA ATATTTATTC ATAAAAAAAA
1451  TACACTTAAA TAAGTAACAA TAATAAAAAA CATTATATAA GAGATTAAGA
1501  TAATTTAATA AGTATTGAAT GTAGAATAAT TTTTATTTAT AAATTTGAAC
1551  TAAAATATTC AAATAATATT CAAAGTAAAT AATAGATATA ATTCATCATT
1601  CAATACGAGT AATTCAATCT ATTATAATCC ATATATTAGA TAAATATACA
1651  AATATTTGTT AAATTTTACA TTATTATATT ACTAAATATA TATTAATTTC
1701  CTTTGAATAT CTTTTATACA AGTAGGTAGA CTAGAAGAAT TATCTTATCT
1751  CCCGTATATT TGTAGATGTT AAATGTAACG GGCTTAGACT GATGTTTTG
1801  TATTATATTA TTTATAAATC CATTAGAGAT TTAAGTTAAT GTCTCTCTTT
1851  GATTTTAAAC ATGGTCTAAA AATTAGGTTT AATCATTGCG TCCTCAATGA
1901  ACCCATGCTA TATGTTTTAA AGTTTTTTGT TTTTTGACAA TGTTTTTTAT
1951  TTCTGAGATT GCTCTTAGGA TTGAAATTAT GTTTGATACT AGAAAACGAA
2001  GAAGTAGAGA GTAGTGTATA CACGTGTAAA AAATAATAGT TGTGGGAACT
2051  TAAGTTGGAT TTGAATACTA GGACGAGGCT GGAAGGGTTT CCACTAAGTT
2101  GACAAAAATT ATTACAAGTG GCAACTAGCT AGGTCTCACA AAGTATTACT
2151  AATTAATAGT GGGTCTGTCT GCATACCAAC TCTTGCCTAA TTTTCAAACA
2201  CCGCATTCTC TCTTCTTCTC TCCTTCTTCC TCTGGAAACT TCATCGATGT
2251  GGACTTCTGT CTCTCAAAAG TCAAGCTCAA TTTATCCAAT GCATTATAAA
2301  TACACACTCT CCCTCCCTTC TATTCTTCAT TGCATCACAT TTCCTCTATA
2351  AATTACTCAC ACCTTATTCC TAACTTCATT TCAACATCCT CTCTCCCACT
2401  TACTTCGATT TCATCAATTC CAATAAACTC AACACACTTT TTTACACTCC
2451  ACACTCTAAC CACATACACC
```

FIGURE 4(ii)

Reconstruction of 2.5 kb pGEL-1 promoter
(a)
1. Cut HindIII and blunt end pGS1.4
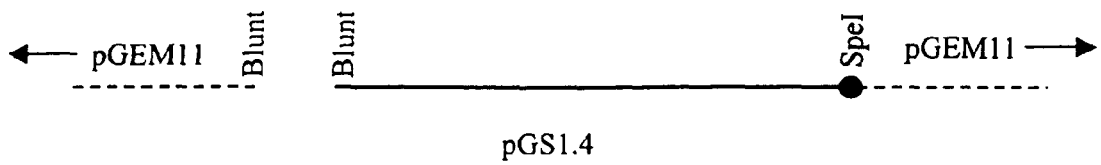
2. Cut SpeI
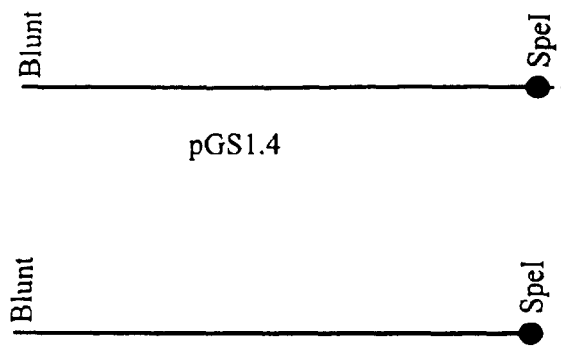
(b)
1. Cut SalI and blunt end pGS1.1
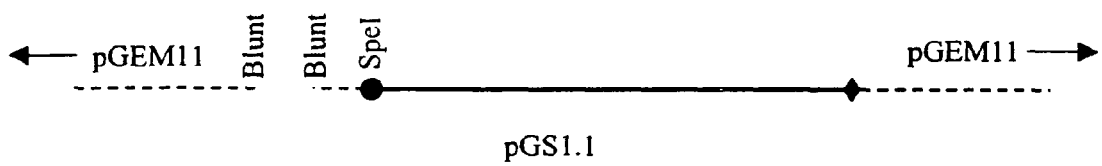
2. Digest with SpeI
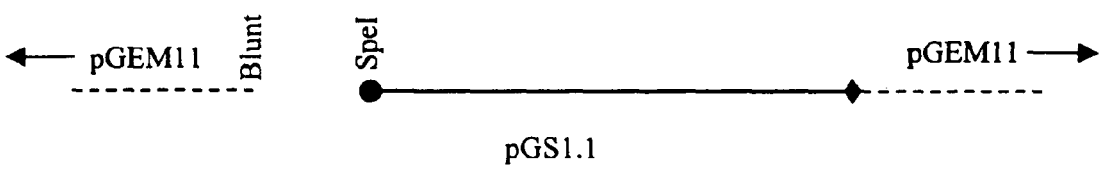
(c) Ligate (a) into (b)
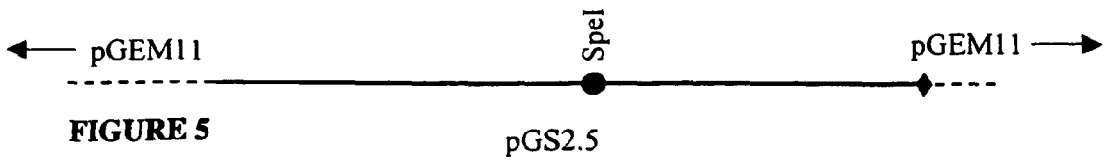
FIGURE 5

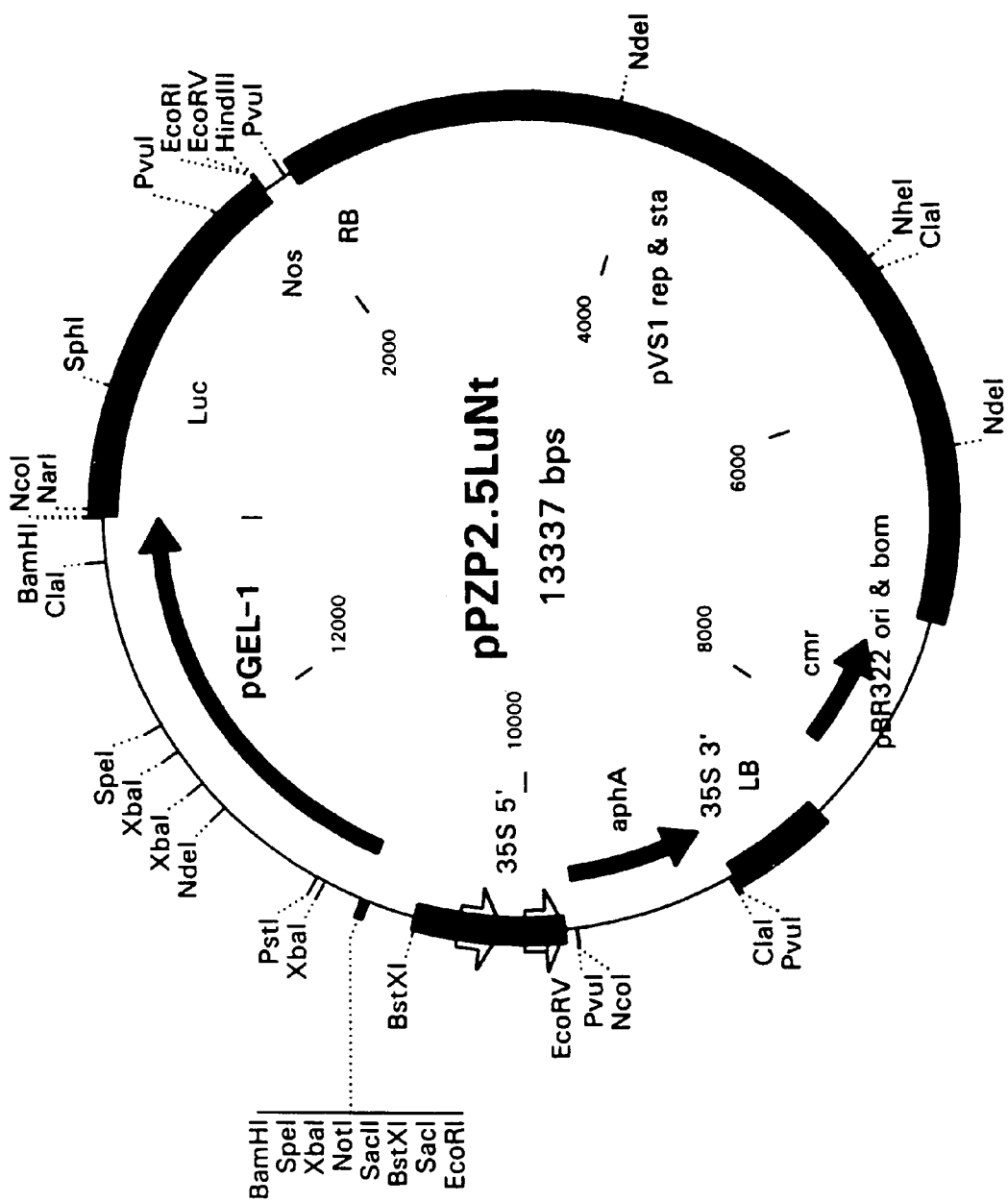
FIGURE 6A(ii)

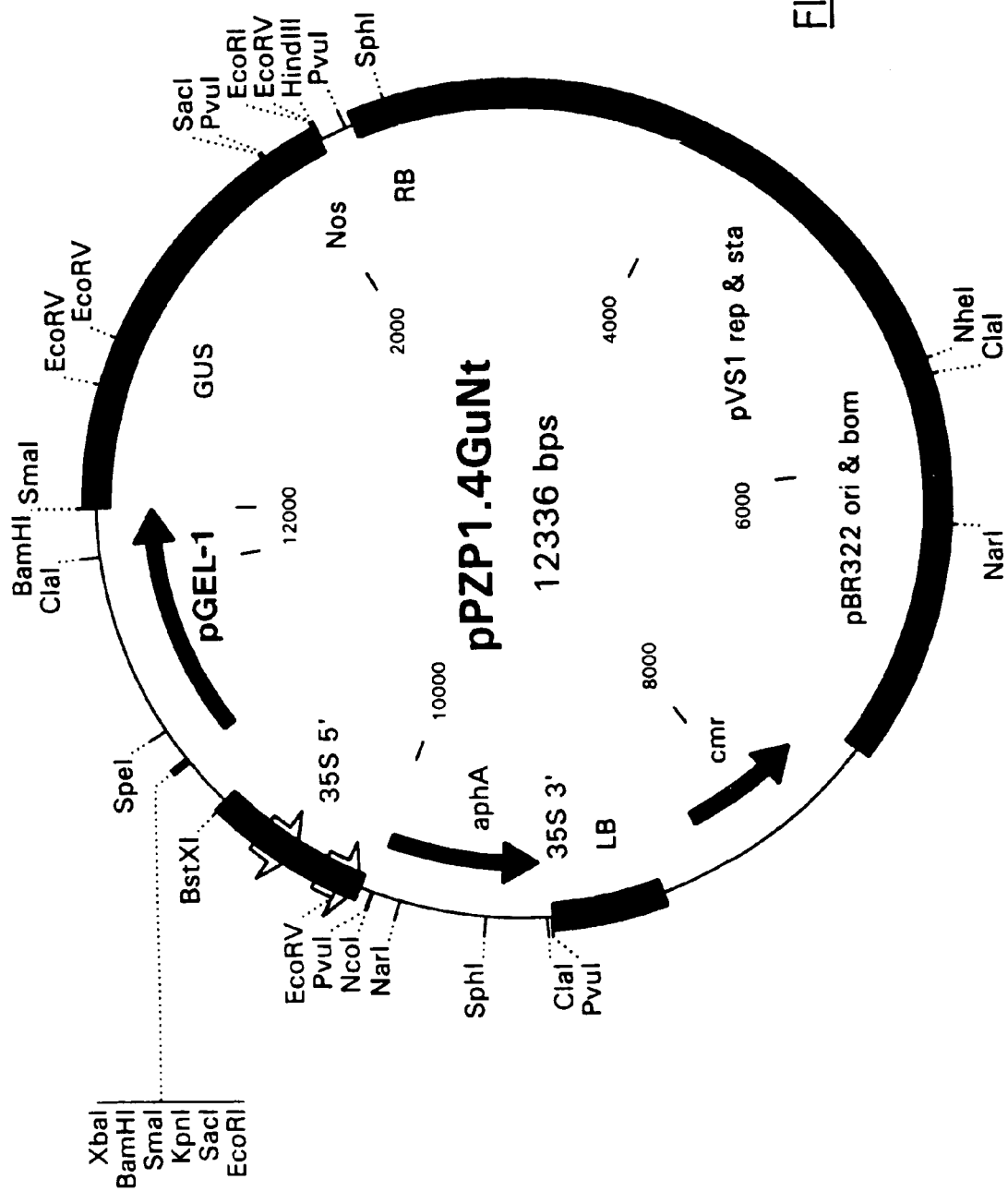
FIGURE 6A(iii)

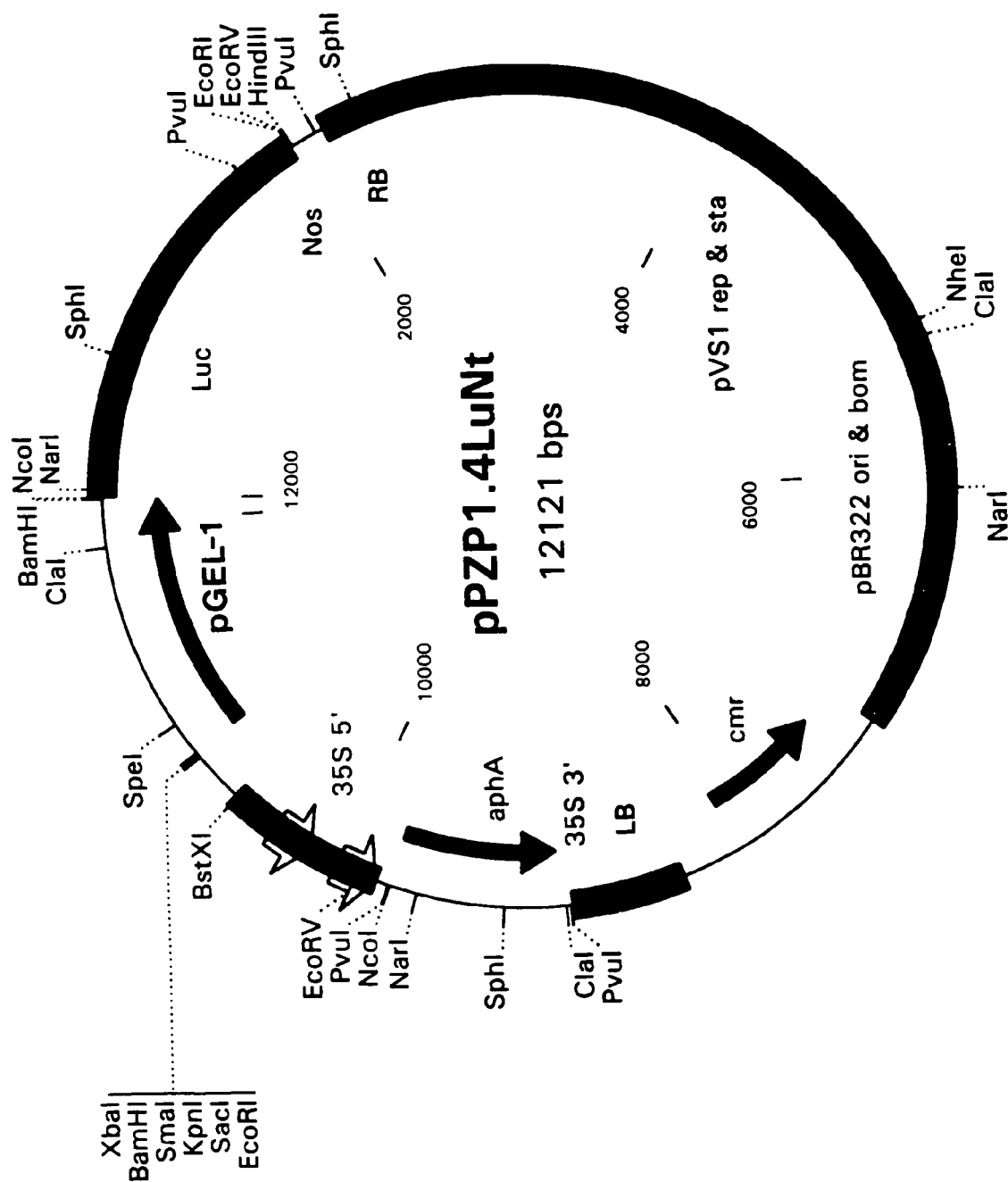
FIGURE 6A(iv)

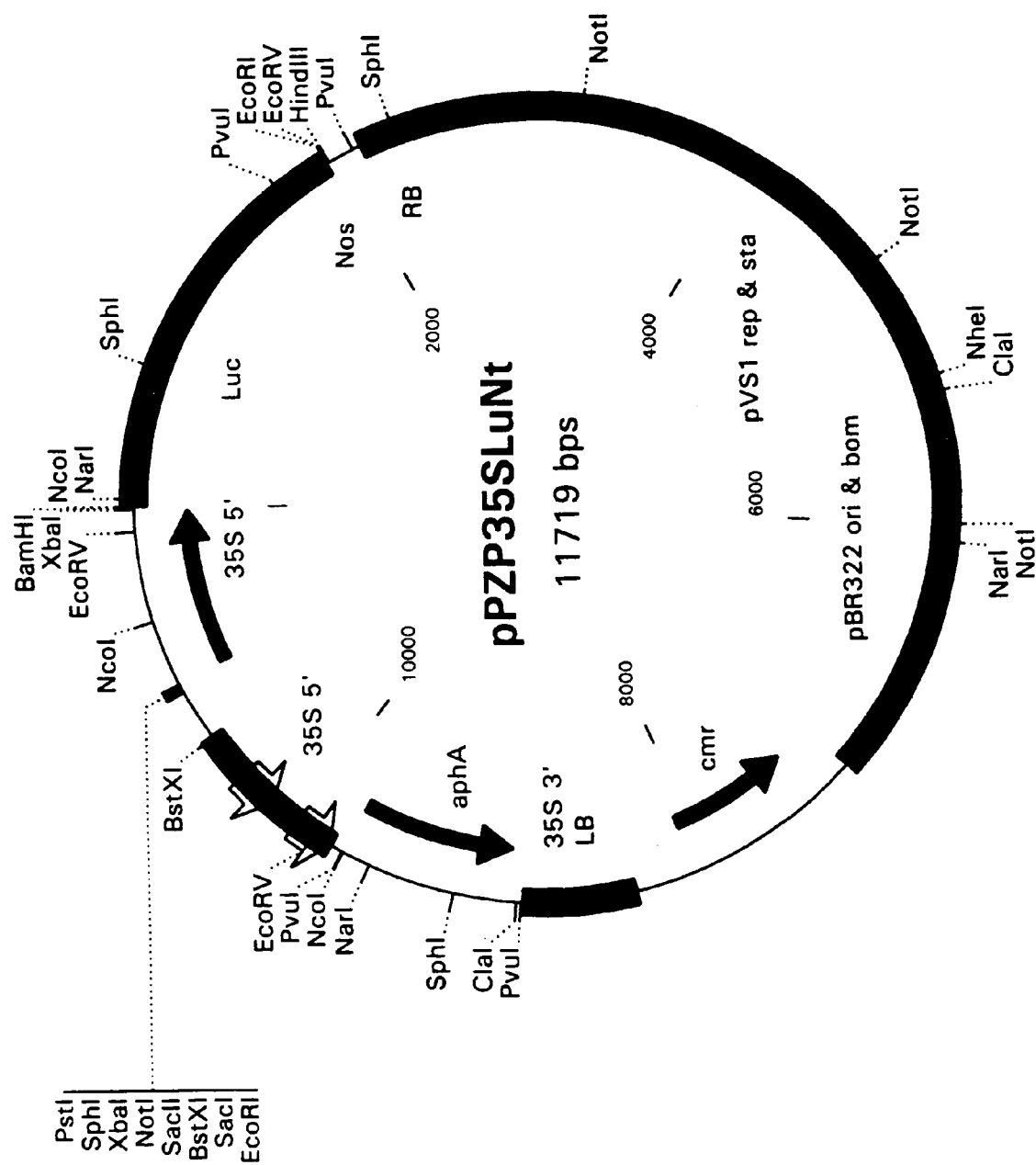
FIGURE 6A(vi)

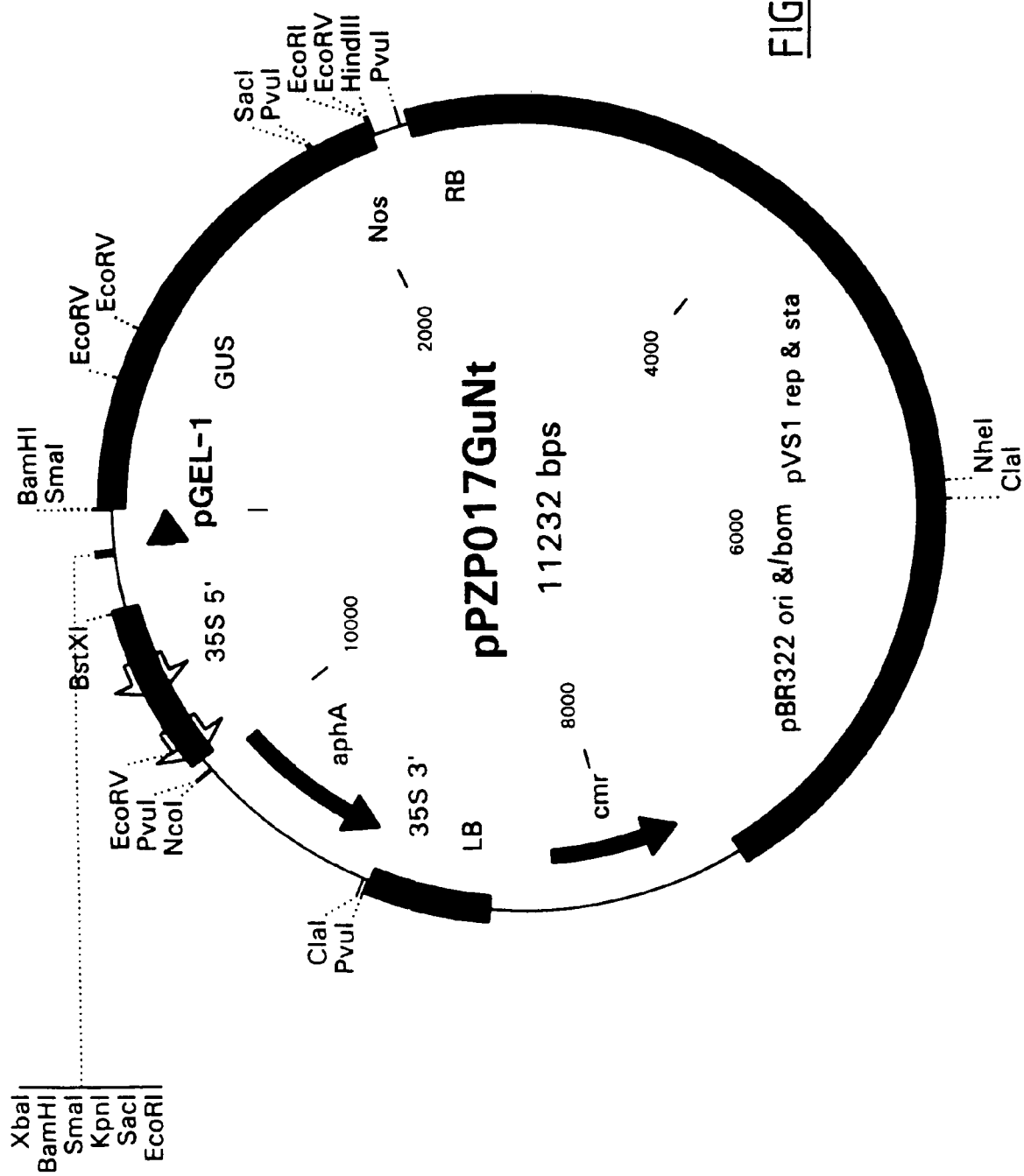
FIGURE 6A(vii)

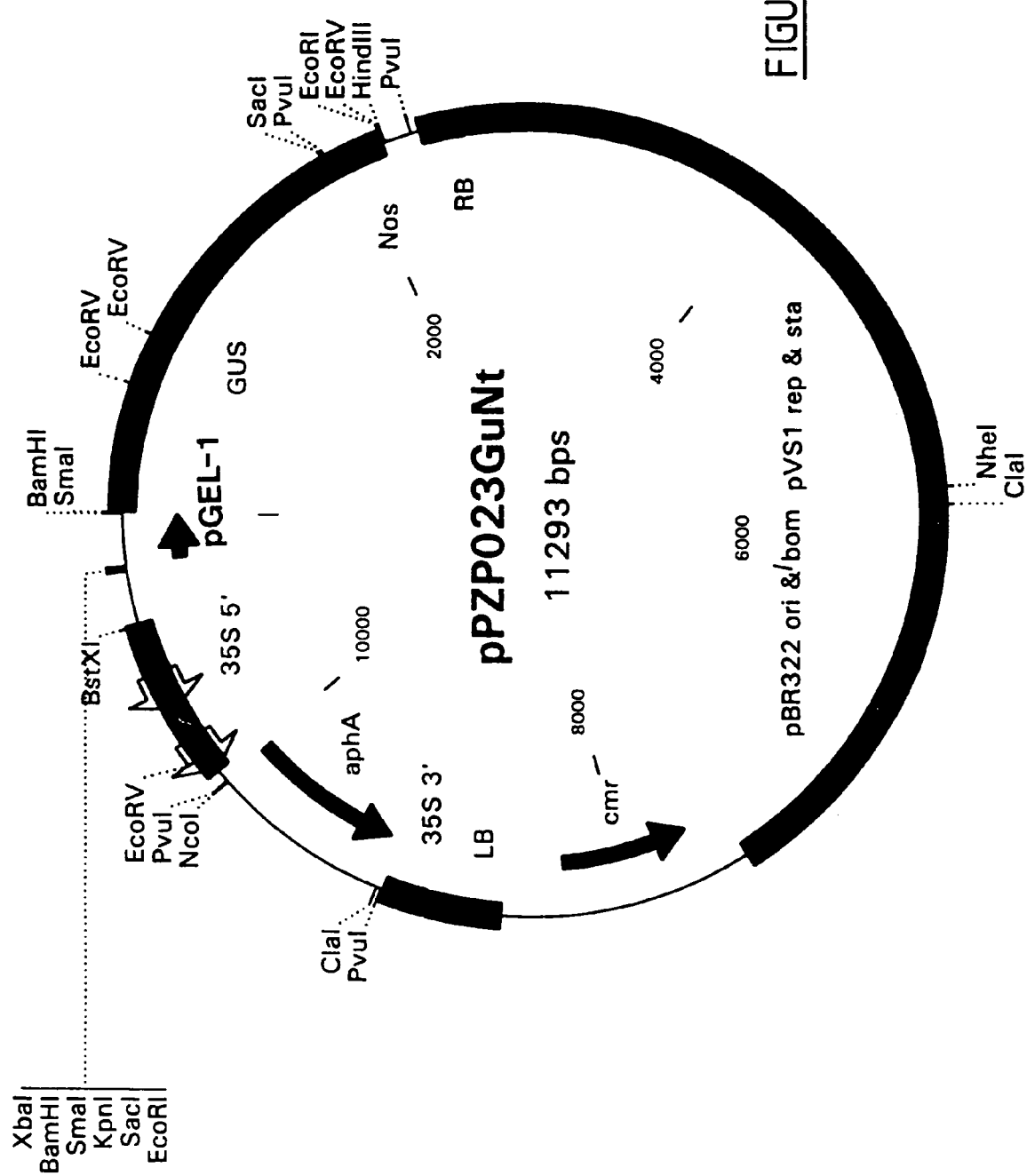
FIGURE 6A(viii)

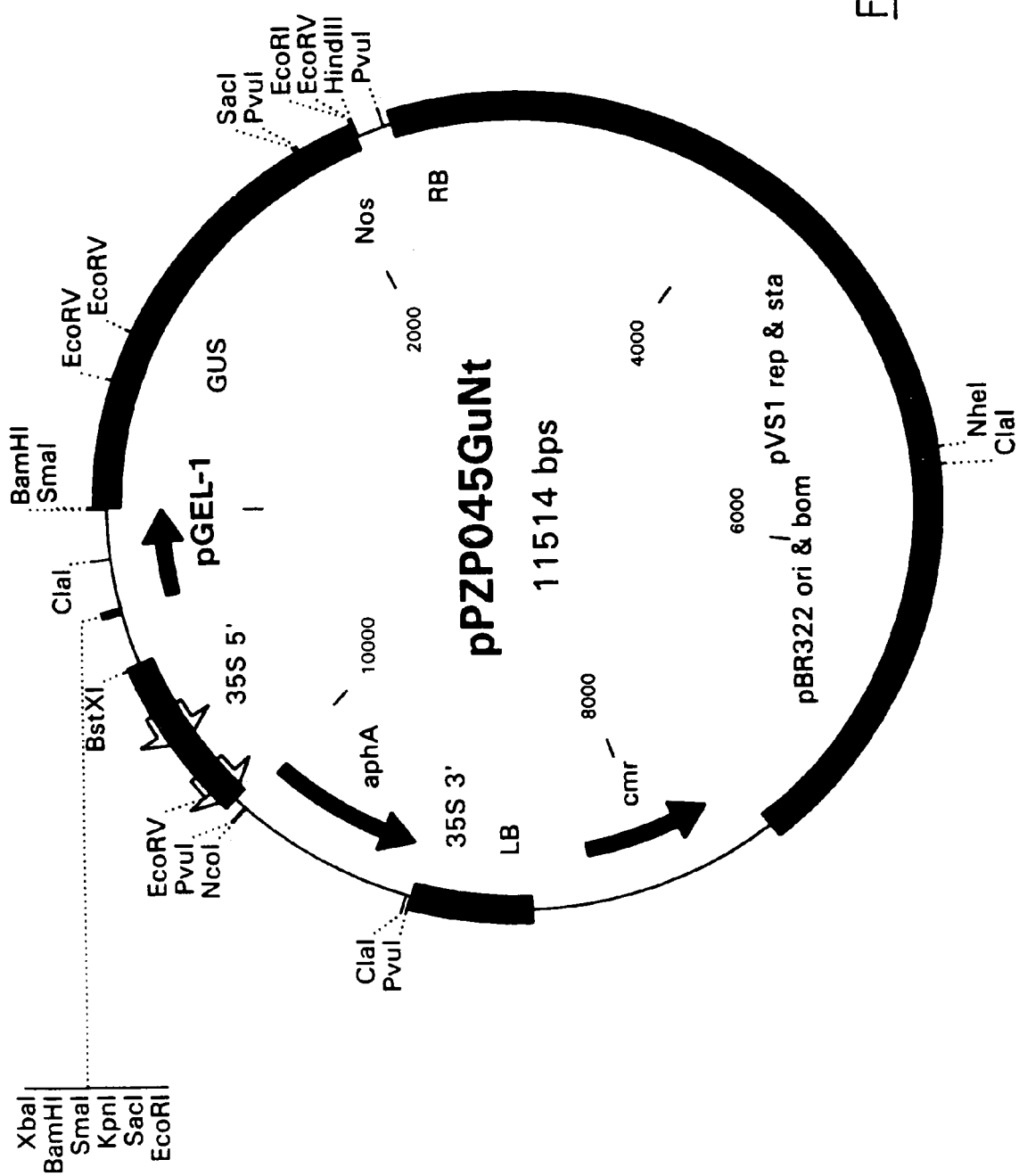
FIGURE 6A(ix)

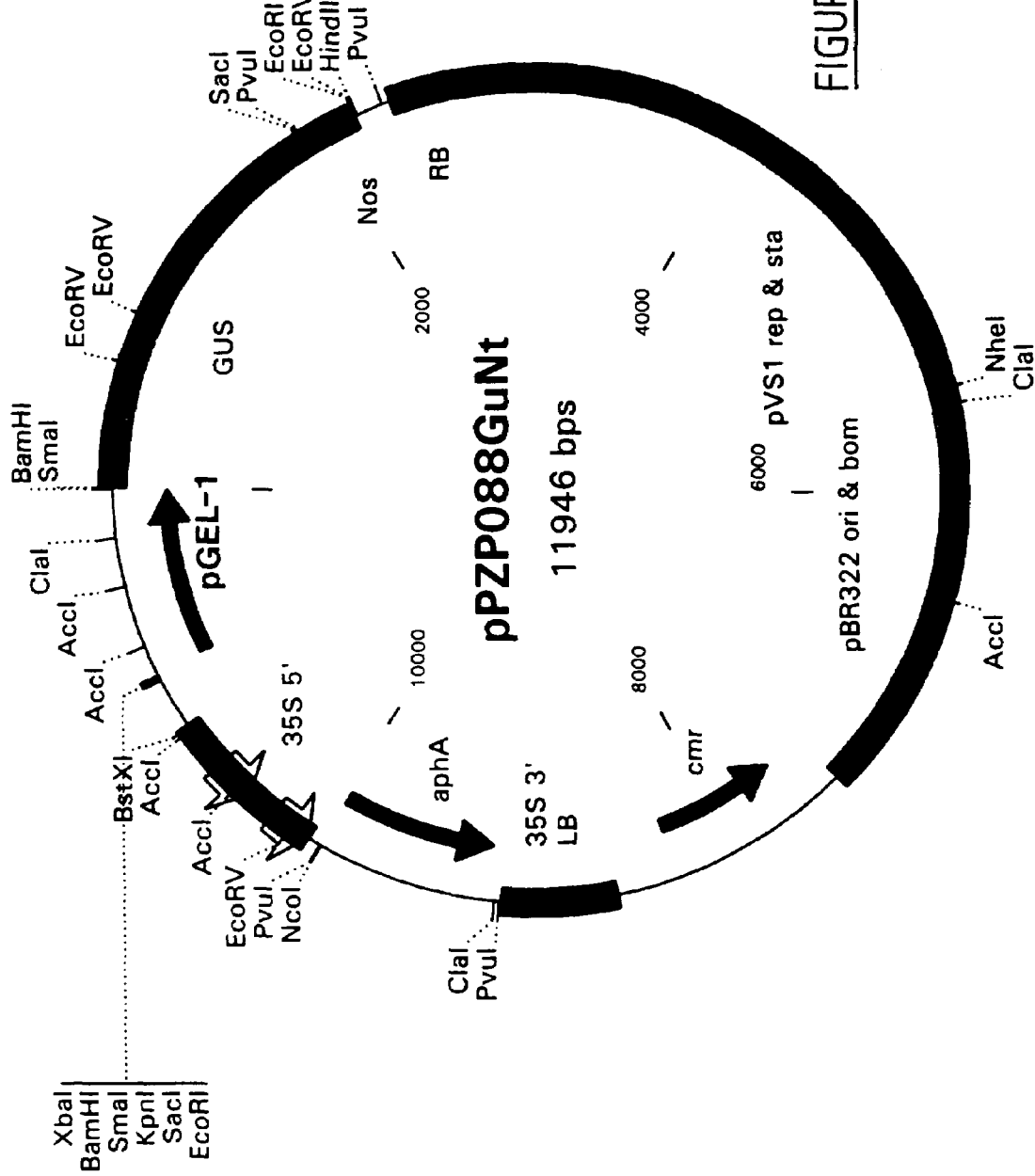
FIGURE 6A(xi)

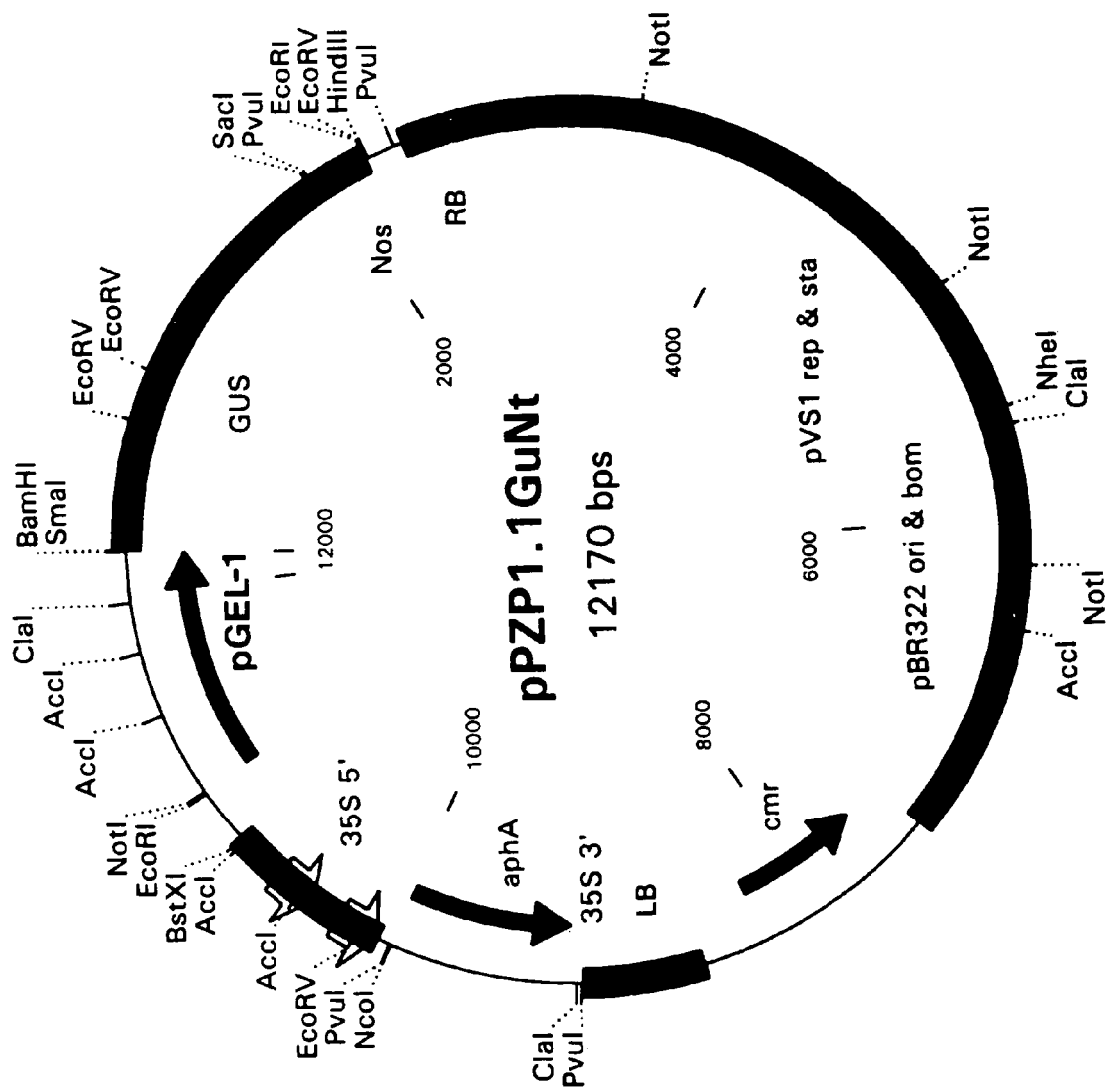
FIGURE 6A(xii)

PLANT PROMOTER AND USES THEREFOR

FIELD OF THE INVENTION

The present invention relates generally to a novel plant promoter. More particularly, the present invention provides a plant promoter capable of induction by physical and/or environmental stimuli in cells in which the promoter is indigenous and, in the absence of any negative regulatory mechanism, is capable of constitutive expression in cells in which the promoter is non-indigenous. The present invention is further directed to derivatives of the subject promoter including modular forms of the promoter which are, for example, inducible by different physical and environmental stimuli or which are constitutively expressed. The promoter of the present invention has a range of uses including directing expression of genes conferring useful traits on plants.

BACKGROUND OF THE INVENTION

Bibliographic details of the publications referred to in this specification are collected at the end of the description.

The subject specification contains nucleotide and amino acid sequence information prepared using the programme PatentIn Version 2.0, presented herein after the bibliography. Each nucleotide or amino acid sequence is identified in the sequence listing by the numeric indicator <210> followed by the sequence identifier (e.g. <210>1, <210>2, etc). The length, type of sequence (DNA, protein (PRT), etc) and source organism for each nucleotide or amino acid sequence are indicated by information provided in the numeric indicator fields <211>, <212> and <213>, respectively. Nucleotide and amino acid sequences referred to in the specification are defined by their sequence identifier (e.g. SEQ ID NO:1, SEQ ID NO:2, etc).

The designation of nucleotide residues referred to herein are those recommended by the IUPAC-IUB Biochemical Nomenclature Commission, wherein A represents Adenine, C represents Cytosine, G represents Guanine, T represents Thymine, Y represents a pyrimidine residue, R represents a purine residue, M represents Adenine or Cytosine, K represents Guanine or Thymine, S represents Guanine or Cytosine, W represents Adenine or Thymine, H represents a nucleotide other than Guanine, B represents a nucleotide other than Adenine, V represents a nucleotide other than Thymine, D represents a nucleotide other than Cytosine and N represents any nucleotide residue.

The rapidly increasing sophistication of recombinant DNA technology is greatly facilitating research and development of a range of biotechnologically-related industries. This is particularly the case in the horticultural, agricultural and plant industries. Substantial progress, for example, has been achieved in the genetic development of plant varieties exhibiting new or improved traits such as disease resistance, enhanced nutritional properties, greater tolerance to adverse environmental conditions and altered flower colour. However, progress in the genetic manipulation of some plants has been hampered by the lack of sufficient effective promoters and/or the lack of promoters capable of being induced by commercially inexpensive and useful effector stimuli. Furthermore, more promoters are required to facilitate expression of multiple traits in a target species. There is a need, therefore, to identify new promoters and to identify and characterize effector molecules and stimuli which are capable of inducing these promoters. There is also a need to identify promoters which are capable of directing constitutive expression.

Plants are subject to a variety of environmental and mechanical stimuli including stress. Although mechanical stress has been postulated to involve ethylene-mediated meristem morphogenesis (Selker et al., 1992), little is known about how mechanical stress induces ethylene production or the signal transduction process involved.

In work leading to the present invention, the inventors sought to identify and isolate promoters involved in mechanical stress-induced expression of genetic traits in *Vigna radiata* (mung bean). Mung bean plants are a useful model for physical and chemical induction of phenotypic expression of genetic traits due to their morphology, rapid growth rate and the ability to obtain a large number of uniform plants and, therefore, sufficient amounts of tissues to conduct analyses.

In accordance with the present invention, the inventors have isolated a promoter capable of induction following physical stimulus in cells in which the promoter is indigenous, i.e., cells of mung bean plants. The promoter is also capable of being induced by a range of chemical and other environmental stimuli. However, in cells in which the promoter is non-indigenous, the promoter is constitutively expressed. The promoter of the present invention is useful in the genetic manipulation of plants.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The promoter of the present invention is referred to herein as "pGEL-1". The promoter was referred to as the "AIM-1 promoter" (or in some cases "AIM-1") in the priority application. Reference herein to "AIM-1" means the structural gene encoding ACC synthase from *Vigna radiata*.

One aspect of the present invention provides an isolated nucleic acid molecule comprising a sequence of nucleotides or a complementary sequence of nucleotides defining a promoter or a derivative or homologue thereof wherein, in its native form, the promoter is inducible in response to physical stimulation.

Another aspect of the present invention is directed to an isolated nucleic acid molecule comprising a sequence of nucleotides or a complementary sequence of nucleotides defining a promoter or a derivative or homologue thereof, wherein said promoter, in its native form, directs expression of a gene associated with ethylene production and is inducible by physical stimulation.

Yet another aspect of the present invention relates to an isolated nucleic acid molecule comprising a sequence of nucleotides or a complementary sequence of nucleotides defining a promoter or a derivative or homologue thereof, wherein said promoter, in its native form, directs expression of a gene encoding ACC synthase and is inducible by physical stimulation.

Still another aspect of the present invention provides an isolated nucleic acid molecule comprising a sequence of nucleotides or a complementary sequence of nucleotides defining a promoter or a derivative or homologue thereof, wherein said promoter, in its native form, directs expression of a gene encoding ACC synthase or another gene associated with ethylene biosynthesis and is inducible by physical stimulation.

Still yet another aspect of the present invention is directed to an isolated nucleic acid molecule comprising a sequence of nucleotides or a complementary sequence of nucleotides defining a promoter or a derivative or homologue thereof, wherein said promoter, in its native form, directs expression of a gene encoding an ACC synthase having an amino acid sequence substantially as set forth in SEQ ID NO:2 or an amino acid sequence having at least 60% similarity to SEQ ID NO:2.

A further aspect of the present invention relates to an isolated nucleic acid molecule comprising a sequence of nucleotides or a complementary sequence of nucleotides defining a promoter or a derivative or homologue thereof wherein said promoter, in its native form, directs expression of a gene encoding ACC synthase and wherein said gene comprises a nucleotide sequence substantially as set forth in SEQ ID NO:1 or a sequence having at least 50% similarity thereto and/or a nucleotide sequence capable of hybridizing to SEQ ID NO:1 under low stringency conditions.

Still another aspect of the present invention is directed to an isolated nucleic acid molecule comprising a sequence of nucleotides or a complementary sequence of nucleotides defining a promoter or a derivative or homologue thereof, wherein said promoter, in its native form, comprises a nucleotide sequence substantially as set forth in SEQ ID NO:3 or a nucleotide sequence having at least 25% similarity thereto or a nucleotide sequence capable of hybridizing to SEQ ID NO:3 under low stringency conditions.

Another aspect of the present invention provides a modular promoter, said modular promoter comprising at least one portion which is derived from a promoter which, in its native form, directs expression of a gene associated with ethylene biosynthesis and is inducible by physical stimulation.

Yet another aspect of the present invention is directed to a modular promoter, said modular promoter comprising at least one portion which is derived from a promoter which, in its native form, directs synthesis of an ACC synthase having an amino acid sequence substantially as set forth in SEQ ID NO:2 or an amino acid sequence having at least 60% similarity thereto.

Still yet another aspect of the present invention is directed to a modular promoter, said modular promoter comprising at least one portion which is derived from a promoter which, it is native form, directs synthesis of an ACC synthase encoded by a gene comprising a nucleotide sequence substantially as set forth in SEQ ID NO:1 or a nucleotide sequence having at least 50% similarity thereto or a nucleotide sequence capable of hybridizing to SEQ ID NO:1 under low stringency conditions.

In still yet another aspect of the present invention, there is provided a modular promoter comprising a portion which is derived from a promoter which comprises, in its native form, a nucleotide sequence substantially as set forth in SEQ ID NO:3 or a nucleotide sequence having at least 25% similarity thereto or a nucleotide sequence capable of hybridizing to SEQ ID NO:3 under low stringency conditions.

Another aspect of the present invention contemplates a genetic construct comprising a promoter or modular promoter each as herein defined or a derivative or homologue thereof, means to facilitate insertion of a nucleotide sequence downstream of and operably linked to said promoter and optionally a gene encoding a selectable marker.

A further aspect of the present invention provides a genetic construct comprising a promoter or modular promoter each as herein defined or a derivative or homologue thereof, a nucleotide sequence operably linked to said promoter and optionally a gene encoding a selectable marker.

Another aspect of the present invention provides an isolated nucleic acid molecule comprising a sequence of nucleotides or a complementary sequence of nucleotides defining a promoter or a derivative or homologue thereof which is capable of constitutive expression in cells in which the promoter is non-indigenous.

Yet another aspect of the present invention is directed to an isolated nucleic acid molecule comprising a sequence of nucleotides or a complementary sequence of nucleotides defining a promoter or a derivative or homologue thereof, wherein said promoter, in its native form, directs expression in response to physical stimulation of a gene associated with ethylene production and which promoter in a non-native host cell is constitutively expressed.

Still yet another aspect of the present invention relates to an isolated nucleic acid molecule comprising a sequence of nucleotides or a complementary sequence of nucleotides defining a promoter or a derivative or homologue thereof, wherein said promoter, in its native form, directs expression in response to physical stimulation of a gene encoding ACC synthase and which promoter in a non-native host cell is constitutively expressed.

A further aspect of the present invention provides an isolated nucleic acid molecule comprising a sequence of nucleotides or a complementary sequence of nucleotides defining a promoter or a derivative or homologue thereof wherein said promoter, in its native form, directs expression of a gene encoding ACC synthase or another gene associated with ethylene biosynthesis and in a cell in which the promoter is indigenous, the promoter is inducible by physical stimulation whereas in a cell in which the promoter is non-indigenous, the promoter is constitutively expressed.

Another aspect of the present invention provides an isolated an isolated acid molecule comprising a sequence of nucleotides or complementary sequence of nucleotides defining a promoter or a derivative or homologue thereof, wherein, in its native form, the promoter is inducible in response to physical stimulation and wherein the promoter is selected from the list consisting of:

(i) a promoter which, in its native form, directs expression of a nucleotide sequence substantially as set forth in SEQ ID NO:1;

(ii) a promoter which, in its native form, directs expression of a nucleotide sequence which hybridizes under low stringency conditions to SEQ ID NO:1;

(iii) a promoter which, in its native form, directs expression of a nucleotide sequence having at least about 50% similarity to SEQ ID NO:1;

(iv) a promoter which, in its native form, directs expression of a nucleotide sequence which encodes an amino acid sequence substantially as set forth in SEQ ID NO:2;

(v) a promoter which, in its native form, directs expression of a nucleotide sequence which encodes an amino acid sequence which has at least about 60% similarity to SEQ ID NO:2;

(vi) a promoter comprising a nucleotide sequence substantially as set forth in SEQ ID NO:3;

(vii) a promoter comprising a nucleotide sequence capable of hybridizing to SEQ ID NO:3 under low stringency conditions; and (viii) a promoter comprising a nucleotide sequence having at least about 25% similarity to SEQ ID NO:3.

BRIEF DESCRIPTION OF THE FIGURES

FIG. 1 is a representation of the oligonucleotide primers used in Long Distance Inverse PCR.

FIG. 5 is a diagrammatic representation of the construction of full length pGEL-1.

DETAILED DESCRIPTION OF THE PREFERRED EMBODIMENTS

Figure 2:
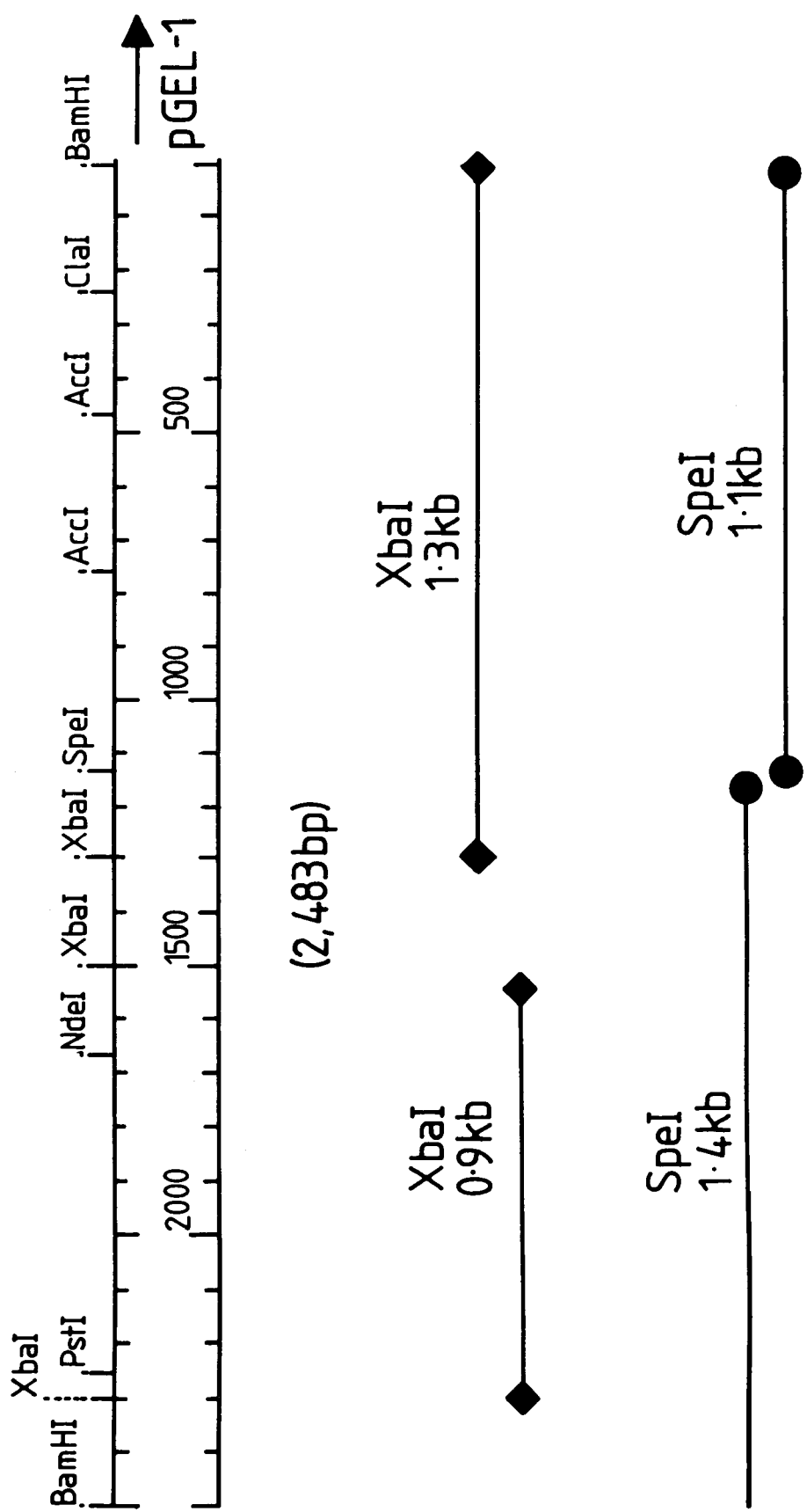
FIG. 2 is a diagrammatic representation showing generation of SpeI and XbaI fragments of pGEL-1.

The present invention is predicated in part on the identification of a promoter directing expression of a gene. The gene encodes 1-aminocyclopropane-1-carboxylic acid synthase ("ACC synthase") and is inducible, in its native form, by physical stimuli (Botella et al, 1992; Botella et al, 1995). Reference herein to "native form" with respect to a promoter means the promoter in cells in which the promoter is normally resident, i.e. indigenous. In the present case, cells from mung bean plants are cells in which the promoter is indigenous. When the promoter is transferred by genetic means to non-mung bean plant cells, the resulting cells are an example of cells carrying a non-indigenous promoter.

Accordingly, the present invention provides an isolated nucleic acid molecule comprising a sequence of nucleotides or a complementary sequence of nucleotides defining a promoter or a derivative or homologue thereof wherein, in its native form, the promoter is inducible in response to physical stimulation.

More particularly, the present invention is directed to an isolated nucleic acid molecule comprising a sequence of nucleotides or a complementary sequence of nucleotides defining a promoter or a derivative or homologue thereof, wherein said promoter, in its native form, directs expression of a gene associated with ethylene production and is inducible by physical stimulation.

Even more particularly, the present invention relates to an isolated nucleic acid molecule comprising a sequence of nucleotides or a complementary sequence of nucleotides defining a promoter or a derivative or homologue thereof wherein said promoter, in its native form, directs expression of a gene encoding ACC synthase and is inducible by physical stimulation.

In a related embodiment, the present invention relates to an isolated nucleic acid molecule comprising a sequence of nucleotides or a complementary sequence of nucleotides defining a promoter or a derivative or homologue thereof wherein said promoter, in its native form, directs expression of a gene encoding ACC synthase or another gene associated with ethylene biosynthesis and is inducible by physical stimulation.

Although the present invention is exemplified by the identification and isolation of the promoter directing synthesis of ACC synthase from *Vigna radiata* (mung bean), the present invention extends to any promoter which, in its native form, is inducible in response to physical stimulation and which directs expression of a nucleotide sequence having at least about 50% similarity to the nucleotide sequence set forth in SEQ ID NO:1 and/or nucleotide sequence capable of hybridizing to the nucleotide sequence of SEQ ID NO:1 under low stringency conditions, such as at 42° C.

Examples of promoters contemplated by the present invention include but are not limited to promoters directing expression of genes associated with ethylene biosynthesis such as the gene encoding ACC synthase.

The gene encoding ACC synthase from mung bean is referred to as AIM-1. ACC synthase from mung bean comprises the amino acid sequence substantially as set forth in SEQ ID NO:2.

Accordingly, another aspect of the present invention is directed to an isolated nucleic acid molecule comprising a sequence of nucleotides or a complementary sequence of nucleotides defining a promoter or a derivative or homologue thereof wherein said promoter, in its native form, directs expression of a gene encoding an ACC synthase having an amino acid sequence substantially as set forth in SEQ ID NO:2 or an amino acid sequence having at least 60% similarity to SEQ ID NO:2.

The percentage similarity at the amino acid or nucleotide sequence level is generally to a portion comprising at least about 20 contiguous amino acids or at least about 60 contiguous nucleotide bases. Preferably, however, the comparison is made to the entire amino acid sequence or entire nucleotide sequence. Alternative percentage similarities include at least about 70%, at least about 80%, at least about 90% and at least about 95% or above or discrete percentages there between.

Genes encoding ACC synthase enzymes not having 100% similarity to SEQ ID NO:2 include derivatives and homologous of the mung bean enzyme. A derivative includes parts, fragments, mutants and fusions of the mung bean ACC synthase defined in SEQ ID NO:2 including ACC synthase enzymes having one or more amino acid substitutions, additions and/or deletions to the amino acid sequence of SEQ ID NO:2. Homologues include enzymes from closely or distantly related plants including fungi.

A particularly preferred promoter of the present invention directs expression of AIM-1. The nucleotide sequence of AIM-1 is set forth in SEQ ID NO:1.

According to this embodiment, there is provided an isolated nucleic acid molecule comprising a sequence of nucleotides or a complementary sequence of nucleotides defining a promoter or a derivative or homologue thereof wherein said promoter in its native form directs expression of a gene encoding ACC synthase and wherein said gene comprises a nucleotide sequence substantially as set forth in SEQ ID NO:1 or a sequence having at least 50% similarity thereto and/or a nucleotide sequence capable of hybridizing to SEQ ID NO:1 under low stringency conditions, such as at 42° C.

For the purposes of defining the level of stringency, those skilled in the art will be aware that several different hybridization conditions may be employed. For example, a low stringency may comprise a hybridization and/or a wash carried out in 6×SSC buffer, 0.1% w/v SDS at from about room temperature to about 44° C. such as from about 28° C. to about 42° C. or equivalent condition sufficient for annealing of primers in a polymerase chain reaction or hybridization of oligonucleotide to DNA or RNA. A medium stringency may comprise a hybridization and/or wash carried out in 2×SSC buffer, 0.1% w/v SDS at a temperature in the range of from about 45° C. to about 65° C. A high stringency may comprise a hybridization and/or wash carried out in 0.1×SSC buffer, 0.1% w/v SDS at a temperature of at least about 65° C. The buffers may also contain from 0% to about 10 to about 15% v/v formamide for use in the hybridization and/or washing solutions.

Generally, the stringency is increased by reducing the concentration of SSC buffer, and/or increasing the concentration of SDS in the hybridization buffer or wash buffer and/or increasing the temperature at which the hybridization and/or wash are performed. Conditions for hybridizations and washes are well understood by one normally skilled in the art. For the purposes of clarification of parameters affecting hybridization between nucleic acid molecules, reference can conveniently be made to pages 2.10.8 to 2.10.16 of Ausubel et al (1987), which is herein incorporated by reference.

Alternative percentage similarities include those set forth above.

Nucleotide sequences not having 100% similarity to SEQ ID NO:1 include derivatives and homologues of mung bean AIM-1. A derivative includes, parts, fragments, mutants and fusions of the mung bean AIM-1 defined in SEQ ID NO:1 including AIM-1 genes having one or more nucleotide substitutions, additions and/or deletions to the nucleotide sequence of SEQ ID NO:1. Homologues include genes from closely or distantly related plants including fungi.

The term "similarity" as used herein includes exact identity between compared sequences at the nucleotide or amino acid level. Where there is non-identity at the nucleotide level, "similarity" includes differences between sequences which result in different amino acids that are nevertheless related to each other at the structural, functional, biochemical and/or conformational levels. Where there is non-identity at the amino acid level, "similarity" includes amino acids that are nevertheless related to each other at the structural, functional, biochemical and/or conformational levels. In a particularly preferred embodiment, nucleotide and sequence comparisons are made at the level of identity rather than similarity. Any number of programs are available to compare nucleotide and amino acid sequences. Preferred programs have regard to an appropriate alignment. One such program is Gap which considers all possible alignment and gap positions and creates an alignment with the largest number of matched bases and the fewest gaps. Gap uses the alignment method of Needleman and Wunsch (1970). Gap reads a scoring matrix that contains values for every possible GCG symbol match. GAP is available on ANGIS (Australian National Genomic Information Service) at their website. Most preferably, the promoter of the present invention comprises a nucleotide sequence substantially as set forth in SEQ ID NO:3 or a functional derivative or homologue thereof.

Accordingly, another aspect of the present invention is directed to an isolated nucleic acid molecule comprising a sequence of nucleotides or a complementary sequence of nucleotides defining a promoter or a derivative or homologue thereof wherein said promoter in its native form comprises a nucleotide sequence substantially as set forth in SEQ ID NO:3 or a nucleotide sequence having at least 25% similarity thereto or a nucleotide sequence capable of hybridizing to SEQ ID NO:3 under low stringency conditions such as at 42° C.

Still another aspect of the present invention provides an isolated nucleic acid molecule comprising a sequence of nucleotides or complementary sequence of nucleotides defining a promoter or a derivative or homologue thereof, wherein, in its native form, the promoter is inducible in response to physical stimulation and wherein the promoter is selected from the list consisting of:

(i) a promoter which, in its native form, directs expression of a nucleotide sequence substantially as set forth in SEQ ID NO:1;

(ii) a promoter which, in its native form, directs expression of a nucleotide sequence which hybridizes under low stringency conditions to SEQ ID NO:1;

(iii) a promoter which, in its native form, directs expression of a nucleotide sequence having at least about 50% similarity to SEQ ID NO:1;

(iv) a promoter which, in its native form, directs expression of a nucleotide sequence which encodes an amino acid sequence substantially as set forth in SEQ ID NO:2;

(v) a promoter which, in its native form, directs expression of a nucleotide sequence which encodes an amino acid sequence which has at least about 60% similarity to SEQ ID NO:2;

(vi) a promoter comprising a nucleotide sequence substantially as set forth in SEQ ID NO:3;

(vii) a promoter comprising a nucleotide sequence capable of hybridizing to SEQ ID NO:3 under low stringency conditions; and (viii) a promoter comprising a nucleotide sequence having at least about 25% similarity to SEQ ID NO:3.

The determination of low stringency conditions may be done from about room temperature to about 44° C. Preferably, low stringency is determined at 28° C. Alternatively, low stringency is determined at 42° C.

The promoter of the present invention is useful in the development of genetic constructs to express heterologous nucleotide sequences placed downstream of, and operably linked to, the promoter.

Reference herein to a "promoter" is to be taken in its broadest context and includes the transcriptional regulatory sequences of a classical genomic gene, including the TATA box which is required for accurate transcription initiation, with or without a CCAAT box sequence and additional regulatory elements (i.e. upstream activating sequences, enhancers and silencers) which alter gene expression in response to developmental and/or environmental stimuli, or in a tissue-specific or cell-type-specific manner. A promoter is usually, but not necessarily, positioned upstream of or 5' to a structural gene, the expression of which it regulates. Furthermore, the regulatory elements comprising a promoter are usually positioned within 2 kb of the start site of transcription of the gene.

In the present context, the term "promoter" is also used to describe a synthetic or fusion molecule, or derivative which confers, activates or enhances expression of a structural gene or other nucleic acid molecule in a plant cell.

The term "operably in connection" or "operably linked to" in the present context means placing a structural gene under the regulatory control of the promoter of the present invention by positioning the structural gene such that the expression of the gene is controlled by the promoter. Promoters and the like are generally positioned 5' (upstream) to the genes that they control. In the construction of heterologous promoter/structural gene combinations, it is generally preferred to position the promoter at a distance from the gene transcription start site that is approximately the same as the distance between that genetic sequence or promoter and the gene it controls in its natural setting, i.e., the gene from which the promoter is derived. As is known in the art, some variation in this distance can be accommodated without loss of function.

As used herein, a "structural gene" shall be taken to refer to that portion of a gene comprising a DNA segment encoding a protein, polypeptide or a portion thereof or alternatively, an isolated nucleic acid molecule which does not necessarily encode a polypeptide, such as an antisense, ribozyme, abzyme or co-suppression molecule.

The term "structural gene" also refers to copies of a structural gene naturally found within the cell, but artificially introduced, or the structural gene may encode a protein not normally found in the plant cell into which the gene is introduced, in which case it is termed a heterologous gene. A heterologous structural gene may be derived in whole or in part from a bacterial genome or episome, eukaryotic genomic or plastid DNA, cDNA, viral DNA, or chemically synthesized DNA. It is possible that a structural gene may contain one or more modifications in either the coding or the untranslated regions which affect the biological activity or the chemical structure of the expression product, the rate of expression, or the manner of expression control. Such modifications include, but are not limited to, mutations, insertions, deletions, and substitutions of one or more nucleotides.

Where the structural gene encodes a polypeptide, it may constitute an uninterrupted coding sequence or it may include one or more introns, bounded by the appropriate plant-functional splice junctions. The structural gene may be a composite of segments derived from a plurality of sources, naturally occurring or synthetic. The structural gene may also encode a fusion protein, as long as the experimental manipulations maintain functionality in the joining of the coding sequences.

Another aspect of the invention relates to the use of the promoter of the present invention or a derivative or homologue or modular form thereof in the identification and/or isolation of similar promoter sequences associated with from other genes.

According to this embodiment, there is contemplated a method for identifying a related nucleic acid molecule which is at least capable of conferring, increasing or otherwise facilitating the expression of a structural gene, when in native form, in response to physical stimulation, said method comprising contacting genomic DNA or parts or fragments thereof, with a hybridization-effective amount of the nucleotide sequence set forth in SEQ ID NO:1 or SEQ ID NO:3, or a part, analogue or derivative thereof or a complementary sequence thereto, and then detecting said hybridization.

Another aspect of the present invention contemplates a nucleic acid molecule defining a promoter or a homologue or derivative thereof said nucleic acid molecule obtainable by the method of isolating genomic DNA from plant cells, rendering the genomic DNA or portion thereof single stranded and then identifying a region on genomic DNA which hybridizes to a primer corresponding to all or part of SEQ ID NO:1 or a complementary form thereof and then cloning DNA upstream of the region of primer hybridization.

The related genetic sequence may be in a recombinant form, in a virus particle, bacteriophage particle, yeast cell, animal cell, or a plant cell. Preferably, the related genetic sequence originates from an agriculturally-important or horticulturally-important plant such as potato, tomato, wheat, barley, canola, oats, maize, sugar cane, cotton or rice and/or wild varieties and/or hybrids or derivatives and/or ancestral progenitors of same. Horticulturally important plants include rose, carnation, petunia, lisianthus, lily, iris, tulip, freesia, delphinium, limonium, pelargonium as well as fruit and vegetable crops such as papaya.

The present invention clearly extends to an isolated nucleic acid molecule which comprises a sequence of nucleotides which overlaps with the sequence set forth in SEQ ID NO:1 or SEQ ID NO:3.

Preferably, such isolated nucleic acid molecules comprise genomic DNA which is isolated using polymerase chain reaction or hybridization approaches based upon the nucleotide information disclosed in SEQ ID NO:1 or SEQ ID NO:3.

Preferably, the genetic sequence set forth in SEQ ID NO:1 or SEQ ID NO:3, or a derivative or analogue thereof, is labelled with a reporter molecule capable of producing an identifiable signal (e.g. a radioisotope such as $^{32}P$, or $^{35}S$, or a biotinylated molecule) to facilitate its use as a hybridization probe in the isolation of related nucleic acid molecules.

An alternative method contemplated in the present invention involves hybridising a nucleic acid primer molecule of at least 10 nucleotides in length, derived from SEQ ID NO:1 or SEQ ID NO:3, or a derivative or analogue thereof, to a nucleic acid "template molecule", said template molecule herein defined as for example, genomic DNA, or a functional part thereof. Specific nucleic acid molecule copies of the template molecule are amplified enzymatically in a polymerase chain reaction, a technique that is well known to one skilled in the art.

Preferably, the nucleic acid primer molecule or molecule effective in hybridization is contained in an aqueous mixture of other nucleic acid primer molecules. More preferably, the nucleic acid primer molecule is in a substantially pure form.

The nucleic acid template molecule may be in a recombinant form, in a virus particle, bacteriophage particle, yeast cell, animal cell, or a plant cell. Preferably, the related genetic sequence originates from an agricultural or horticultural plant or other suitable plant species.

The present invention extends to the subject promoter in a genetic construct.

The term "genetic construct" is used in its broadest sense to include an isolated nucleic acid molecule comprising a sequence of nucleotides.

The genetic construct is conveniently engineered so as to include means to facilitate insertion of a nucleotide sequence in a region 3' of the promoter, to place a nucleotide sequence downstream of and operably linked to, the promoter which then directs its transcription. Such a "means" includes but is not limited to a restriction endonuclease-mediated insertion, homologous recombination, transposon insertion, PCR mediated insertion and random insertion. Preferably, the means is a restriction endonuclease site. Generally, the inserted restriction site is unique to the genetic construct or may be represented, for example, twice but separated by a nucleic acid sequence which is deleted upon restriction digestion of the genetic construct. The required nucleotide sequence to be transcribed is then inserted into the deleted region.

The genetic construct of the present invention may comprise solely the promoter and optionally a nucleotide sequence downstream thereof or, alternatively, may comprise additional nucleotide sequences constituting promoter regulatory region(s), transcribed sequence regulatory regions, a marker (e.g., antibiotic resistance, chemical compound resistance or enzyme such as β-galactosidase (GUS) or luciferase (LUC) β-glucuronidase), autonomous replication region and/or or genome integration sequence. The promoter may be the naturally occurring promoter or may be an active fragment or part thereof or a derivative, analogue or homologue of the promoter.

Accordingly, another aspect of the present invention contemplates a genetic construct comprising a promoter or modular promoter each as herein defined or a derivative or homologue thereof, means to facilitate insertion of a nucleotide sequence operably linked to said promoter and optionally a gene encoding a selectable marker.

More particularly, this aspect provides a genetic construct comprising a promoter or modular promoter as herein defined or a derivative or homologue thereof, one or more unique restriction sites down stream of said promoter to enable the insertion of a heterologous nucleotide sequence operably linked to said promoter and a gene encoding a selectable marker.

In a related embodiment, the present invention provides a genetic construct comprising a promoter or modular promoter each as herein defined or a derivative or homologue thereof, a nucleotide sequence operably linked to said promoter and optionally a gene encoding a selectable marker.

The present invention extends to genetic constructs in which the genetic sequence of the invention, or a functional derivative, part, fragment, homologue, or analogue thereof, is operably linked to a structural gene sequence. The invention is not, however, limited by the nature of the structural gene sequence contained in such genetic constructs.

In one embodiment, the structural gene sequence is a reporter gene, such as but not limited to the β-glucuronidase gene, or the chloramphenicol acetyl transferase gene, or the firefly luciferase gene, amongst others.

In an alternative embodiment, the structural gene sequence encodes, or is complementary to a structural gene sequence encoding, a cytotoxin or other gene product which, when produced in a plant cell, kills or significantly alters host cell metabolism to limit cell division.

In a further alternative embodiment, the structural gene sequence encodes, or is complementary to a structural gene sequence encoding, a hormone polypeptide or polypeptide which is involved in the biosynthesis of a hormone or other molecule. The invention particularly contemplates the expression of a phytohormone molecule under control of the promoter defined in SEQ ID NO:3 or an analogue or derivative thereof, to produce a high local concentration of said phytohormone in the undifferentiated cells which is sufficient to result in the development of a floral meristem or vegetative meristem, depending upon the nature of the phytohormone.

In a still further alternative embodiment, the structural gene sequence may be a ribozyme, abzyme, antisense or co-suppression molecule which targets the expression of a gene. According to this embodiment, expression of such a structural gene under the control of the genetic sequence of the invention will partially or completely reduce, delay or inhibit the expression of said structural gene.

Yet another alternative embodiment comprises a structural gene whose product facilitates the accumulation of a molecule which itself or a further metabolic or oxidised form thereof facilitates a change in the colour of plant tissue, cells, organs, leaves or flowers. For example, the structural gene may encode a flavonoid pathway enzyme or a cytochrome P450 molecule such as a plant, mammalian or bacterial monooxygenase.

Wherein the structural gene being targeted is normally expressed in more than one cell type, the expression of said structural gene under control of the promoter of the present invention may further result in the gene being expressed in a cell-type or tissue-type specific pattern.

The genetic construct according to this aspect of the invention may further comprise a transcription termination sequence, placed operably in connection with the structural gene sequence.

In an alternative embodiment, the transcription termination sequence is placed downstream of the promoter of the present invention, optionally spaced therefrom by a nucleotide sequence which comprises one or more restriction endonuclease recognition sites, to facilitate the insertion of a structural gene sequence as hereinbefore defined between said genetic sequence and said transcription termination sequence.

The term "terminator" refers to a DNA sequence at the end of a transcriptional unit which signals termination of transcription. Terminators are 3'-non-translated DNA sequences containing a polyadenylation signal, which facilitates the addition of polyadenylate sequences to the 3'-end of a primary transcript. Terminators active in cells derived from viruses, yeasts, moulds, bacteria, insects, birds, mammals and plants are known and described in the literature. They may be isolated from bacteria, fungi, viruses, animals and/or plants.

Examples of terminators particularly suitable for use in the genetic constructs of the present invention include the nopaline synthase (NOS) gene terminator of *Agrobacterium tumefaciens*, the terminator of the Cauliflower mosaic virus (CaMV) 35S gene, the zein gene terminator from *Zea mays*, the Rubisco small subunit (SSU) gene terminator sequences, subclover stunt virus (SCSV) gene sequence terminators, any rho-independent *E. coli* terminator, amongst others.

The genetic construct of the instant invention may further include an origin of replication sequence which is required for replication in a specific cell type, for example a bacterial cell, when said genetic construct is required to be maintained as an episomal genetic element (e.g. plasmid or cosmid molecule) in said cell.

Preferred origins of replication include, but are not limited to, the f1-ori and co/E1 origins of replication.

In a further alternative embodiment, the genetic construct of the invention further comprises one or more selectable marker genes or reporter gene sequences, placed operably in connection with a suitable promoter sequence which is operable in a plant cell and optionally further comprising a transcription termination sequence placed downstream of said selectable marker gene or reporter gene sequences.

As used herein, the term "selectable marker gene" includes any gene which confers a phenotype on a cell in which it is expressed to facilitate the identification and/or selection of cells which are transfected or transformed with a genetic construct of the invention or a derivative thereof.

Suitable selectable marker genes contemplated herein include the ampicillin resistance gene ($Amp^r$), tetracycline resistance gene ($Tc^r$), bacterial kanamycin resistance gene ($Kan^r$), phosphinothricin resistance gene, neomycin phosphotransferase gene (nptII), hygromycin resistance gene, β-glucuronidase (GUS) gene, chloramphenicol acetyltransferase (CAT) gene and luciferase gene, amongst others.

Those skilled in the art will be aware that the choice of promoter for expressing a selectable marker gene or reporter gene sequence may vary depending upon the level of expression required and/or the species from which the host cell is derived and/or the tissue-specificity or development-specificity of expression which is required.

Examples of promoters suitable for use in expressing selectable marker or reporter gene in the genetic constructs of the present invention include promoters derived from the genes of viruses, yeasts, moulds, bacteria, insects, birds, mammals and plants which are capable of functioning in isolated plant cells or whole organisms regenerated therefrom; including whole plants. The promoter may regulate the expression of the selectable marker gene or reporter gene constitutively, or differentially with respect to the tissue in which expression occurs, or with respect to the developmental stage at which expression occurs, or in response to external stimuli such as physiological stresses, pathogens, or metal ions, amongst others.

Examples of promoters include the CaMV 35S promoter, NOS promoter, octopine synthase (OCS) promoter, *Arabidopsis thaliana* SSU gene promoter, napin seed-specific promoter, $P_{32}$ promoter, BK5-T imm promoter, lac promoter, tac promoter, phage lambda $\lambda_L\lambda_R$ or promoters, CMV promoter (U.S. Pat. No. 5,168,062), T7 promoter, lacUV5 promoter, SV40 early promoter (U.S. Pat. No. 5,118,627), SV40 late promoter (U.S. Pat. No. 5,118,627), adenovirus promoter, baculovirus P10 or polyhedrin promoter (U.S. Pat. Nos. 5,243,041; 5,242,687; 5,266,317; 4,745,051; and 5,169,784), and the like. In addition to the specific promoters identified herein, cellular promoters for so-called housekeeping genes are useful.

Those skilled in the art will be aware of additional promoter sequences and terminator sequences which may be suitable for use in performing the invention. Such sequences may readily be used without any undue experimentation.

A still further embodiment contemplates a genetic construct which further comprises one or more integration sequences.

As used herein, the term "integration sequence" shall be taken to refer to a nucleotide sequence which facilitates the integration into plant genomic DNA of a genetic sequence of the invention with optional other integers referred to herein.

Particularly preferred integration sequences according to this embodiment include the left border (LB) and right border (RB) sequences of T-DNA derived from the Ti plasmid of *Agrobacterium tumefaciens* or a functional equivalent thereof.

Another aspect of the invention provides a method of expressing a structural gene in a plant cell, said method comprising introducing into said plant cell a genetic construct comprising a promoter sequence which is at least capable of conferring, increasing or otherwise regulating expression of a structural gene to which it is operably connected in a plant cell, wherein said promoter sequence preferably comprises the nucleotide sequence set forth in SEQ ID NO: 3, or a functional derivative, part, fragment, homologue, or analogue thereof which is at least 25% similar thereto or a complementary sequence thereto or a sequence capable of hybridising to SEQ ID NO:3 under low stringency conditions such as 28° C. or 42° C. and wherein said structural gene is operably linked to said promoter sequence on said genetic construct.

The method according to this aspect of the invention is particularly useful for the expression of a wide range of foreign structural genes in cells of plants, including a cell cycle control protein; an antibody-expressing gene, such as a SCAB gene; a selectable marker gene that confers resistance against kanamycin, phosphinothricin, spectinomycin or hygromycin, amongst others; a reporter gene including GUS, CAT, LUC and pigment genes, amongst others; a gene encoding a regulatory protein which modulates expression of a gene in plant cells; and a gene which encodes a developmental regulatory protein, such as, for example, a homeobox protein, that is involved in regulating the developmental fate of a cell. As will be apparent from the disclosure herein, the present method is clearly applicable to the expression of antisense molecules, ribozyme molecules, co-suppression molecules, gene-targeting molecules, or other molecules that are intended to modulate the expression of one or more endogenous plant genes.

A further aspect of the present invention provides a transfected or transformed cell, tissue, organ or whole organism which comprises the promoter or its derivatives or homologues of the present invention. Preferably, the cell, tissue, organ or whole organism expresses a structural gene operably under the control of said promoter sequence.

This aspect of the invention clearly encompasses a transgenic plant such as a crop plant or flowering plant, transformed with a recombinant DNA molecule which comprises at least a genetic sequence which is at least 25% similar to SEQ ID NO:3.

The genetic construct of the present invention may be introduced into a cell by various techniques known to those skilled in the art. The technique used may vary depending on the known successful techniques for that particular organism.

Means for introducing recombinant DNA into bacterial cells, yeast cells, or plant, insect, fungal (including mould), avian or mammalian tissue or cells include, but are not limited to, transformation using $CaCl_2$ and variations thereof, direct DNA uptake into protoplasts, PEG-mediated uptake to protoplasts microparticle bombardment, electroporation, microinjection of DNA, microparticle bombardment of tissue explants or cells, vacuum-infiltration of tissue with nucleic acid, or in the case of plants, T-DNA-mediated transfer from *Agrobacterium* to the plant tissue.

For microparticle bombardment of cells, a microparticle is propelled into a cell to produce a transformed cell. Any suitable ballistic cell transformation methodology and apparatus can be used in performing the present invention. Exemplary apparatus and procedures are disclosed by Stomp et al. (U.S. Pat. No. 5,122,466) and Sanford and Wolf (U.S. Pat. No. 4,945,050). When using ballistic transformation procedures, the genetic construct may incorporate a plasmid capable of replicating in the cell to be transformed.

Examples of microparticles suitable for use in such systems include 0.1 to 10 μm gold or tungsten spheres such as a 0.5-5 μm gold or tungsten sphere. The DNA construct may be deposited on the microparticle by any suitable technique, such as by precipitation.

Once introduced into the plant tissue, the expression of a structural gene under control of the promoter of the present invention may be assayed in a transient expression system, or it may be determined after selection for stable integration within the plant genome.

Where the cell is derived from a multicellular organism and where relevant technology is available, a whole organism may be regenerated from the transformed cell, in accordance with procedures well known in the art.

Those skilled in the art will be aware of the methods for transforming, regenerating and propagating other type of cells, such as those of fungi.

In the case of plants, plant tissue capable of subsequent clonal propagation, whether by organogenesis or embryogenesis, may be transformed with a genetic construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem).

The regenerated transformed plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The regenerated transformed cells contemplated herein may take a variety of forms. For example, they may be chimeras of transformed cells and non-transformed cells; clonal transformants (e.g., all cells transformed to contain the expression cassette); grafts of transformed and untransformed tissues (e.g., in plants, a transformed root stock grafted to an untransformed scion).

The promoter of the present invention, in its native form (i.e. in cells in which it is indigenous), is inducible by physical stimulus which includes mechanical stress, movement, vibration, air pressure, water stress and the like. Other non-mechanical stimuli also induce the instant promoter including auxins, abscisic acid, salt concentration amongst others. Non-mechanical stimuli include environmental stimuli such as but not limited to chemical induction of the promoter. The promoter may also be developmentally regulated and/or may be tissue or organ specific.

As stated above, the identification of a promoter capable of induction by physical or mechanical stimuli provides a particularly useful basis for developing a range of genetically altered plants. For example, air movement may be used to activate expression of a nucleotide sequence operably linked to the subject promoter. This may be useful during the commercial cultivation of large numbers of plants. Generating air movement such as generated by fanning, or a change in air pressure over and/or around the plants can be used to activate expression of the promoter. Alternatively, or in addition, water droplets generated mechanically or by controlling humidity may be used to stimulate promoter activity. Heterologous nucleotide sequences operably linked to the promoter are then expressed. Such heterologous sequences may encode, for example, resistance to insect or other pathogens, salt tolerance, enzymes which manipulate the flow of metabolites down particular biochemical pathways, enzymes which alter the nutritional content of certain types of plant tissues including seeds and other reproductive parts and antisense, co-suppression, ribozyme or deoxyribozyme molecules to down regulate expression of an endogenous gene. Examples of the latter would be to render a plant male or female sterile, to alter biochemical pathways or to otherwise alter the characteristics of the target plant, such as to inhibit ethylene biosynthesis or to delay senescence.

Accordingly, another aspect of the present invention contemplates a method of altering a characteristic of a plant said method comprising introducing a genetic construct into a cell or group of cells of a plant, said genetic construct comprising a promoter as herein defined and a nucleotide sequence operably linked to said promoter and wherein said nucleotide sequence facilitates the altering of said plant characteristic, regenerating a plant or plantlet from said cell or group of cells carrying said genetic construct and growing or subjecting said plant or plantlet to conditions sufficient to induce the promoter in said genetic construct.

The genetically altered plant may be subjected to physical stimulus such as mechanical stress in order to induce the promoter. Alternative forms of stimulus, however, are also contemplated by the subject invention such as water droplets, air movement, air pressure and chemical stimuli such as auxins. The promoter may also be constitutively expressed.

An altered characteristic may be readily determined by comparing a transgenic plant with a non-transgenic plant of the same species. The comparison may be at the biochemical, physiological or visual level. Altered characteristics include but are not limited to resistance to plant viruses, bacteria, fungi, nematodes and other pathogens, improved nutritional value (e.g. using sunflower high sulphur gene), an expression of an "antibody" (often referred to as a "plantabody"), altered biochemical pathways, altered fertility, altered flower colour amongst many other characteristics.

The promoter of the present invention is in its native form, inducible by a range of stimuli including physical, environmental, chemical and genetic. The promoter comprises, therefore, different regulatory areas for different stimuli. The present invention contemplates the manipulation of the subject promoter such that it is inducible by a particular stimulus or stimuli.

Accordingly, another aspect of the present invention provides a modular promoter, said modular promoter comprising at least one portion which is derived from a promoter which, in its native form, directs expression of a gene associated with ethylene biosynthesis and is inducible by physical stimulation.

More particularly, the present invention is directed to a modular promoter, said modular promoter comprising at least one portion which is derived from a promoter which, in its native form, directs synthesis of an ACC synthase having an amino acid sequence substantially as set forth in SEQ ID NO:2 or an amino acid sequence having at least 60% similarity thereto.

Even more particularly, the present invention is directed to a modular promoter, said modular promoter comprising at least one portion which is derived from a promoter which, it is native form, directs synthesis of an ACC synthase encoded by a gene comprising a nucleotide sequence substantially as set forth in SEQ ID NO:1 or a nucleotide sequence having at least 50% similarity thereto or a nucleotide sequence capable of hybridizing to SEQ ID NO:1 under low stringency conditions.

Still more particularly, the present invention provides a modular promoter comprising a portion which is derived from a promoter which comprises, in its native form, a nucleotide sequence substantially as set forth in SEQ ID NO:3 or a nucleotide sequence having at least 25% similarity thereto or a nucleotide sequence capable of hybridizing to SEQ ID NO:3 under low stringency conditions.

Low stringency may be determined at about from room temperature to about 44° C. such as at 28° C. to 42° C. (e.g., 28° C. or 42° C.).

A "modular" promoter is considered as an example of a "derivative". Another derivative contemplated by the present invention includes the deletion of negatively acting cis element(s). This aspect of the present invention is predicated on the observation of high expression of the promoter in the presence of the protein synthesis inhibitor, cycloheximide, which inhibits production of a highly unstable, short-lived negative regulator (transcription factor) of the subject promoter. Accordingly, by deleting the negative cis element(s), higher inducible or even constitutive expression of the promoter may be obtained.

Another aspect of the present invention contemplates an isolated nucleic acid molecule comprising a sequence of nucleotides or a complementary sequence of nucleotides defining a promoter or a derivative or homologue thereof which is capable of constitutive expression in cells in which the promoter is non-indigenous.

This aspect of the present invention is predicated on the surprising observation that the promoter of the present invention, when placed in plant cells in which it is not indigenous, i.e. non-mung bean cells, is constitutively expressed. Although not intending to limit the present invention to any one theory or mode of action, it is proposed that in cells in which the promoter is indigenous, a negative regulatory molecule prevents constitutive expression of the promoter. This negative regulatory molecule would not normally be present in other plant cells and, hence, the promoter is constitutively expressed.

Accordingly, another aspect of the present invention provides an isolated nucleic acid molecule comprising a sequence of nucleotides or a complementary sequence of nucleotides defining a promoter or a derivative or homologue thereof, wherein said promoter, in its native form, directs expression in response to physical stimulation of a gene associated with ethylene production and in which in a non-native host cell is constitutively expressed.

More particularly, a further aspect of the present invention is directed to an isolated nucleic acid molecule comprising a sequence of nucleotides or a complementary sequence of nucleotides defining a promoter or a derivative or homologue thereof wherein said promoter, in its native form, directs expression of a gene encoding ACC synthase or another gene associated with ethylene biosynthesis and in a cell in which the promoter is indigenous, the promoter is inducible by physical stimulation whereas in a cell in which the promoter is non-indigenous, the promoter is constitutively expressed.

The present invention further contemplates a transgenic plant carrying the promoter of the present invention or parts, limbs, flowers, petals, reproductive portions or seeds thereof or progeny or clones thereof.

The present invention is further described by the following non-limiting Examples.

Example 1

Detection of Mechanical Strain-Induced Gene

A gene encoding 1-aminocyclopropane-1-carboxylic acid synthase ("ACC synthase"), induced inter alia by mechanical strain, auxin and salt stress was isolated according to Botella et al. (1992; 1995). The cDNA sequence and corresponding amino acid sequence is shown in SEQ ID NO:1. The amino acid sequence alone is shown in SEQ ID NO:2. This gene is referred to herein as AIM-1. Its promoter is referred to herein as "pGEL-1".

Example 2

Cloning of the ACC Synthase Gene (AIM-1) Promoter (pGEL-1)

(a) Recirculation of DNA

Ten micrograms of genomic DNA isolated by CsCl purification was digested with 2.5 U/μg of HindIII in the presence of 0.1 M spermidine, extracted with 1 volume phenol:chloroform:isamyl alcohol (25:24:1) and precipitated by addition of 0.1 vol NaOAc and 2 volumes EtOH. DNA was then re-ligated with 9 Weiss units of T4 DNA ligase and purified using Bresatec's Bresa Clean Kit. The effectiveness of recircularisation was analyzed by gel electrophoresis.

(b) Long Distance Inverse Polymerase Chain Reaction (LDIPCR) Procedure

A reaction mixture of 2 mM $MgSO_4$ pH 9.1, containing 60 mM Tris-$SO_4$ and a small number, e.g. see $MgSO_4$, 18 mM $(NH_4)_2 SO_4$, 0.2 mM of each dNTP, 0.2 μM of NSE oligonucleotide primers (see FIG. 1), sterile water and 300 ng of recircularised genomic DNA was prepared in a total volume of 40 μl. The reaction mixture was vortexed and briefly spun prior to incubation at 94° C. to prevent non-specific primer interactions. Before initialising the thermal cycle, 10 μl of sterile water containing 1 μl of Life Technologies' eLONGase enzyme mix (TaqI/Vent polymerases) was added to the reaction and mixed by pipetting. An equal volume of mineral oil was layered over the mix to prevent evaporation. The optimised PCR parameters are shown in Table 1.

TABLE 1

PCR profile times and temperatures used during amplification and reamplification protocols.

| | Optimised Temperatures and Times | | | |
|---|---|---|---|---|
| Amplification | Initial Step | Denaturation | Anneal and Extension | |
| | 60 sec. 94° C. | 30 sec. 94° C. 45 cycles | 480 sec. 68° C. | |
| Reamplification | Initial Step | Denaturation | Anneal | Extension |
| | 60 sec. 94° C. | 30 sec. 94° C. 35 cycles | 30 sec. 62° C. | 480 sec. 68° C. |

After the final step of thermal cycling, 1 volume of chloroform-isoamyl alcohol (24:1) was added to remove the oil layer and the samples were stored at 4° C.

Cloning Strategy

The circularised genomic DNA was first amplified with oligonucleotide primers NSE-1 and NSE-2 (refer to FIG. 1). The products of this first amplification were further reamplified using either NSE-3/NSE-4 or NSE-5/NSE-6 (FIG. 1). Electrophoretic analysis of the amplification products, generated with both combinations of primers, revealed a DNA fragment of approximately 4 kb.

Example 3

Analysis of 4 kb Fragment

The 4 kb product obtained with NSE3/NSE-4 was excised from the gel and purified with glassmilk (Bresatec's Bresa Clean). As attempts at cloning the 4 kb product were initially unsuccessful, alternative strategies were devised. The purified 4 kb product was digested with XbaI and two fragments of 1.3 kb and 0.9 kb (see FIG. 2) were sub-cloned into the vector pGEM11 (Promega corporation, USA), which had been previously digested with XbaI giving the plasmids pGX1.3 and pGX0.9, respectively. The 4 kb fragment was also digested with SpeI and blunt-ended before cloning the digestion products into pGEM11 (previously digested with XhoI and blunt-ended). As a result, two SpeI fragments of 1.1 kb and 1.4 kb (see FIG. 2) were sub-cloned and the plasmids named pGS1.1 and pGS1.4, respectively. The 1.4 kb fragment did not show any SpeI recognition sequences in one of its ends, indicating that some exonuclease activity had taken place during the blunt-ending process.

Example 4

Reconstruction and Sequencing of the 2.5 kb pGEL-1 Region

Figure 3:
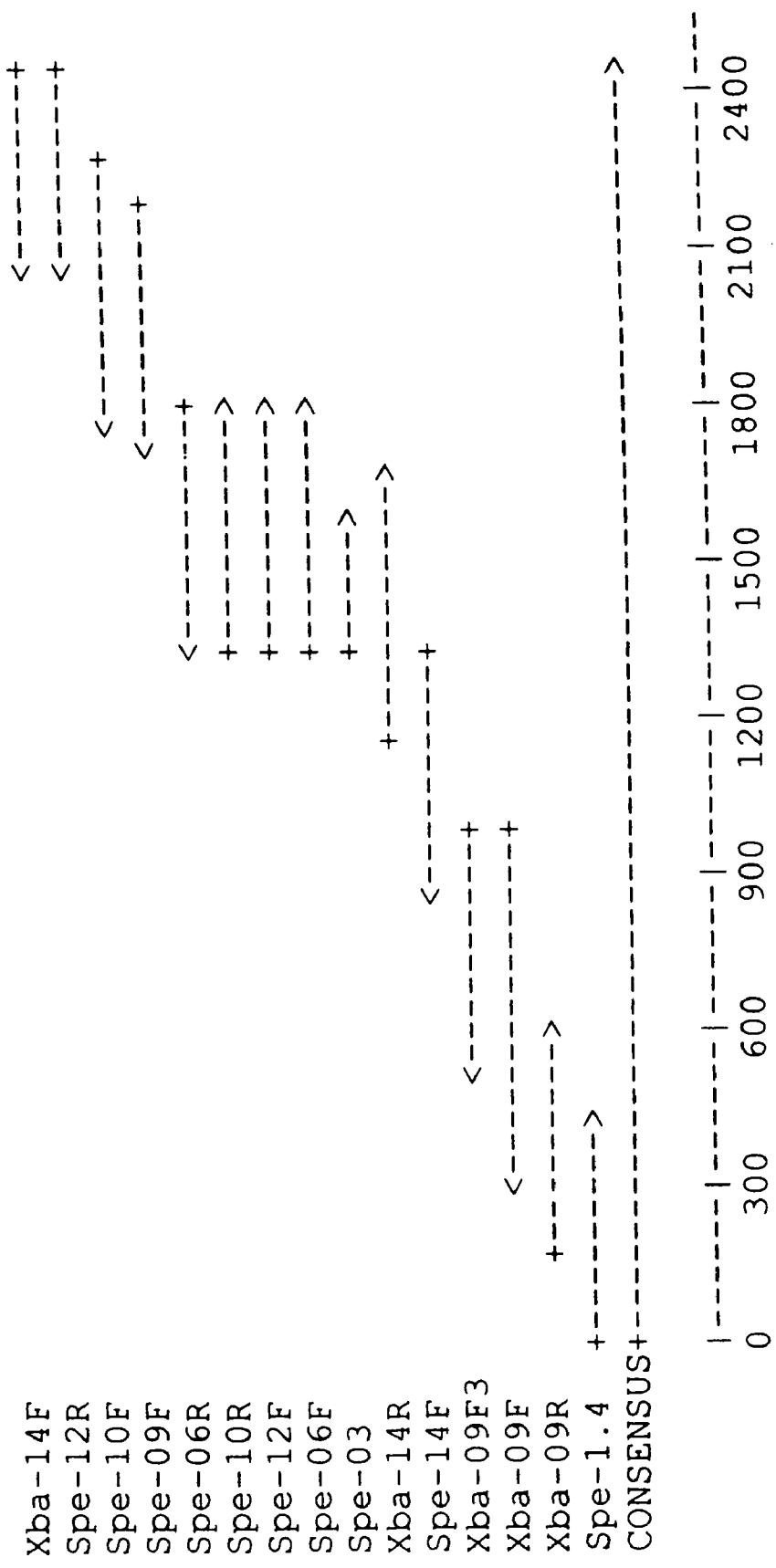
FIG. 3 is a diagrammatic representation of pGEL-1 sequencing strategy.
Figure 4:
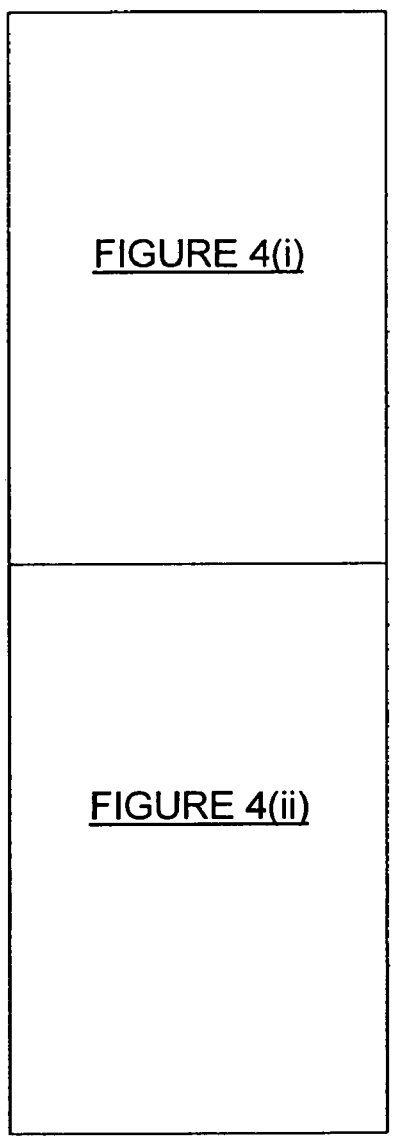
FIG. 4 is a representation of the nucleotide sequence of pGEL-1 (2470 bp).

The sequencing strategy for pGEL-1 is shown in FIG. 3. Sequencing was performed using the dideoxy chain termination method (Sanger et al, 1977) using a Applied Biosystems kit (Applied Biosystems, USA). Analysis of the sequences revealed that the four clones partially overlapped. The 1.3 kb XbaI and 1.1 kb SpeI fragments contained the 5' untranslated region of the AIM-1 cDNA, confirming that this region is upstream of the AIM-1 gene. As a result, a partial restriction map for a 2.5 kb region of the 4 kb DNA fragment was generated. The nucleotide sequence of pGEL-1 is shown in FIG. 4 and in SEQ ID NO:3.

With this information in hand, the promoter region was reconstructed by the following strategy (refer to FIG. 5). pGS1.4 was digested with HindIII and blunt ended. The promoter insert was then excised with SpeI, obtaining a 1.4 kb fragment with blunt-SpeI ends (see FIG. 5(a)).

pGS1.1 was linearised with SalI and blunt ended. Later the linearised construct was digested with SpeI resulting in a linearised vector with blunt-SpeI ends containing the 3' end of the promoter region (FIG. 5(b)). The fragment excised in (a) was ligated into (b) to reconstruct the 2.5 kb pGEL-1 promoter (FIG. 5(b)).

Example 5

Characterization of pGEL-1

(a) Generation of Deletion Fragments and Chimeric Gene Constructs

To fully characterize pGEL-1, two different lengths of the promoter sequence were used: the entire 2.5 kb sequence and a 1.4 kb fragment upstream of the first ATG codon. β-Glucuronidase (GUS) and luciferase (LUC) reporter genes were each ligated to one or other of the promoter fragments and to the 3' terminator region from the *Agrobacterium tumefaciens* nopaline synthase gene (NOS) to generate a series of chimeric gene constructs.

A series of 7 deletions in the promoter region were also generated, starting from 170 base-pairs upstream of the first ATG codon. Each of these was likewise ligated to the NOS 3' terminator region and to the GUS reporter gene. Intermediate vectors containing each of the promoter fragments (0.17, 0.23, 0.45, 0.70, 0.88, 1.1, 1.4, 1.6 or 2.5 kb) ligated to the GUS reporter gene and NOS terminator were generated in pBluescript. Intermediate vectors comprising the promoter fragments 1.4 and 2.5 kb were also ligated to the LUC reporter gene with the NOS terminator. For control purposes, additional constructs containing the cauliflower mosaic virus 35S promoter linked to either GUS or LUC were also prepared.

Figure 6A:
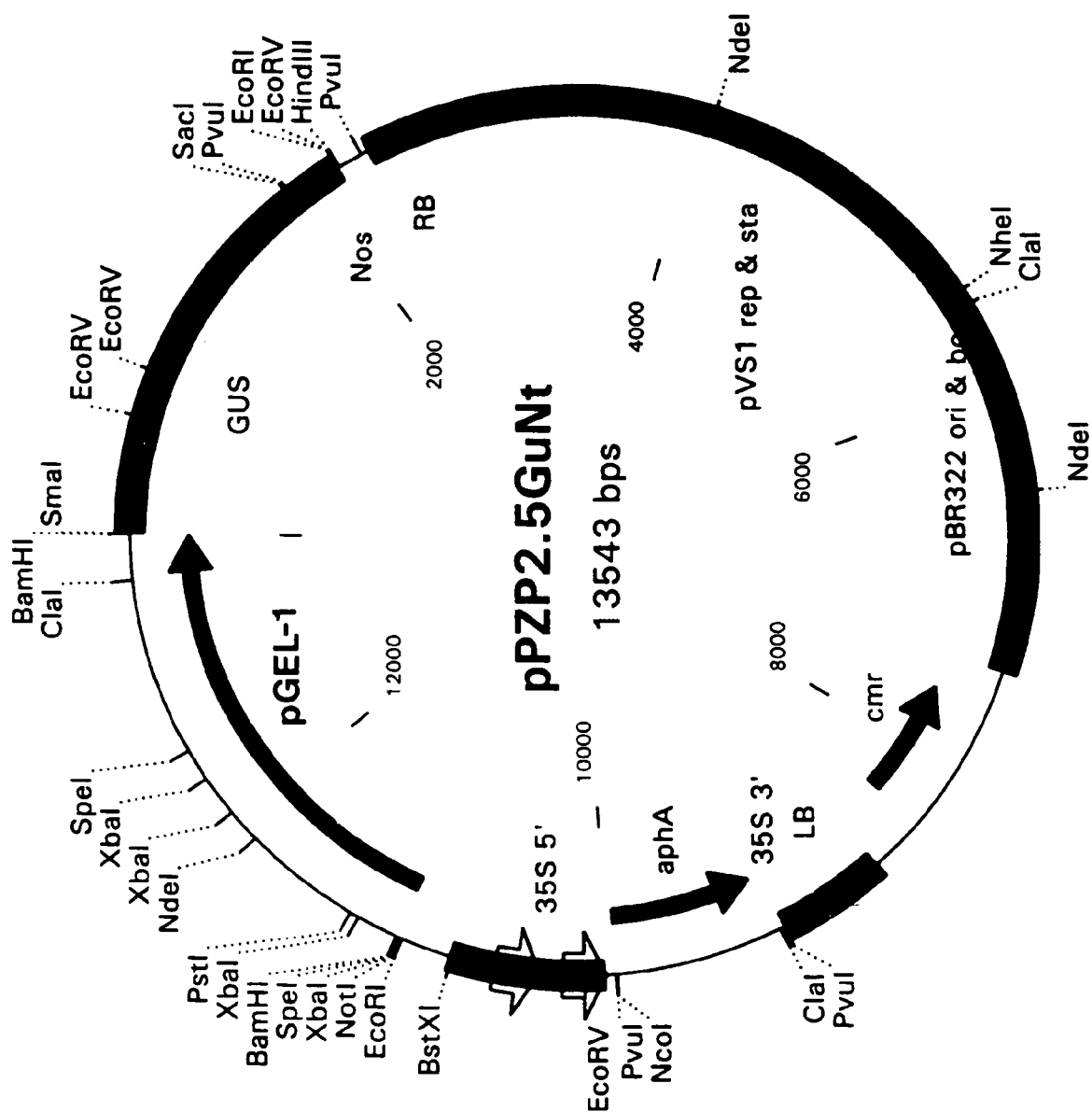
FIG. 6A(i)-6A(xii) are diagrammatic representations of plasmids pPZP2.5GuNt, pPZP2.5LuNt, pPZP1.4GuNt, pPZP1.4LuNt, pPZP35SGuNt, pPZP35SLuNt, pPZP017GuNt, pPZP023GuNt, pPZP045GuNt, pPZP070GuNt, pPZP088GuNt and pPZP1.1GuNt, respectively. Gu, GUS; Lu, luciferase (LUC); Nt, Nos terminator; 35S, cauliflower mosaic virus 35S promoter. The number given after the term "pPZP" represents the length of the promoter sequence in kilobases. For example, pPZP2.5LuNt contains the full length promoter, pGEL-1.
Figure 6A:
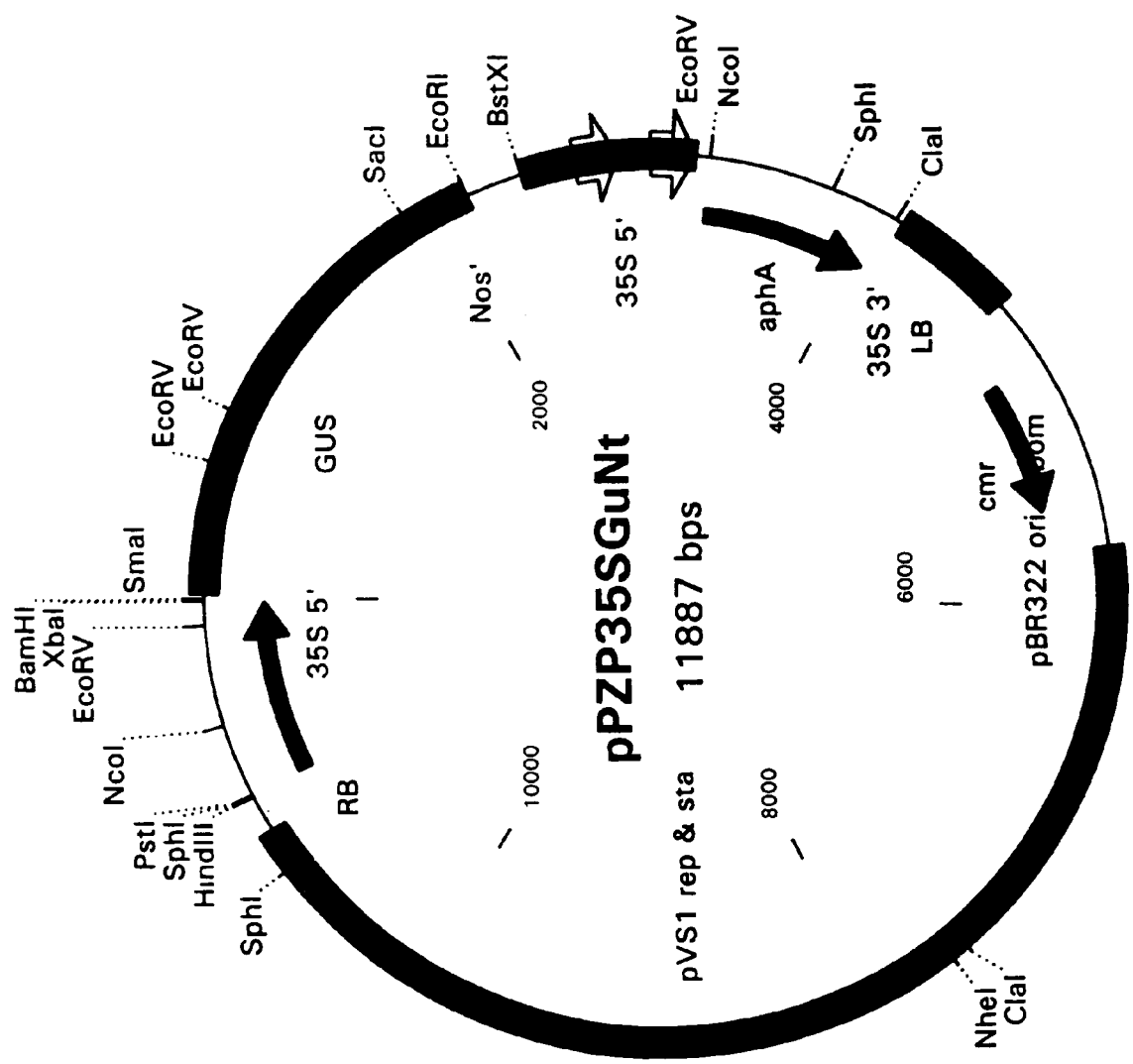
Figure 6A:
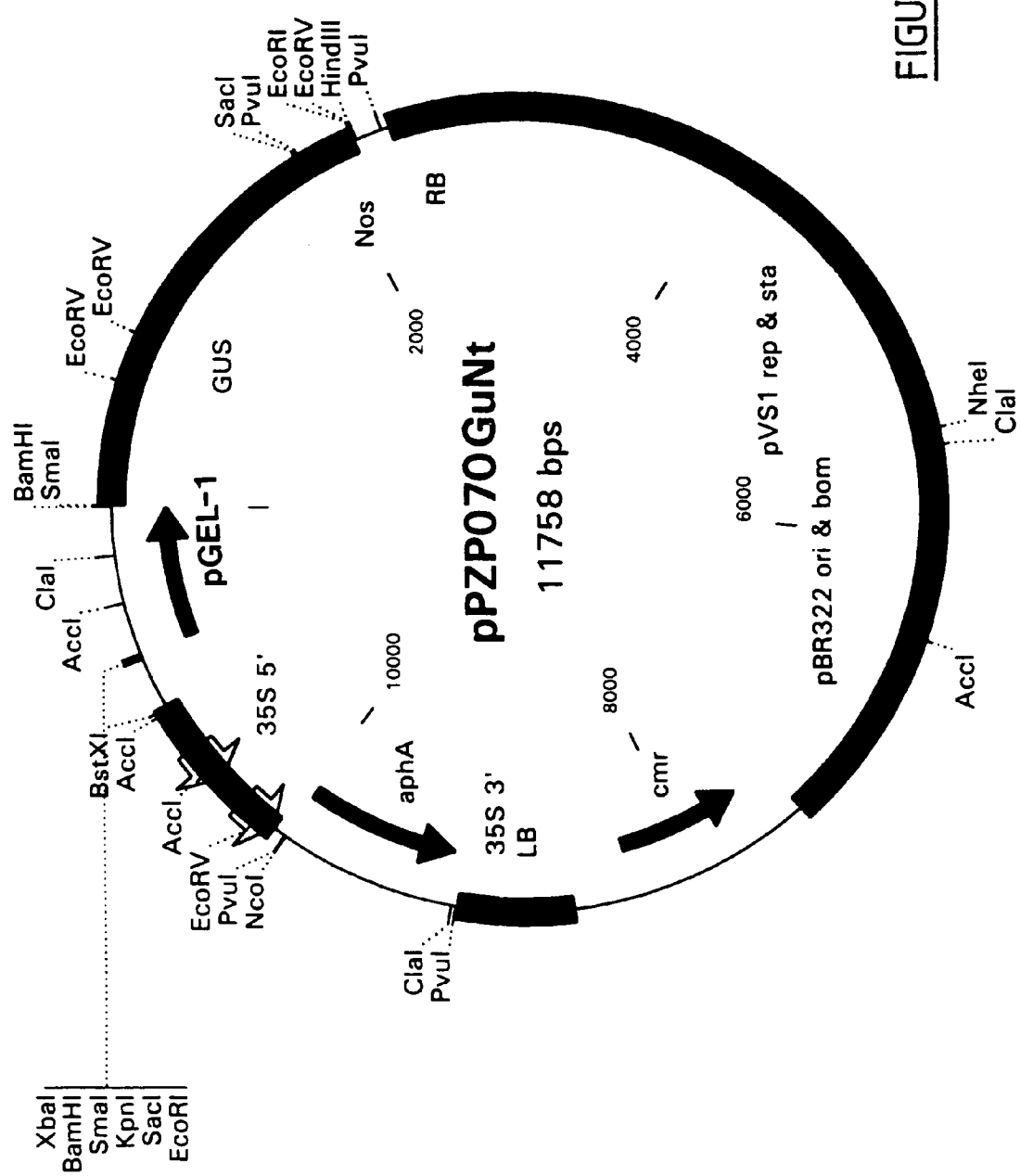
Figure 6B:
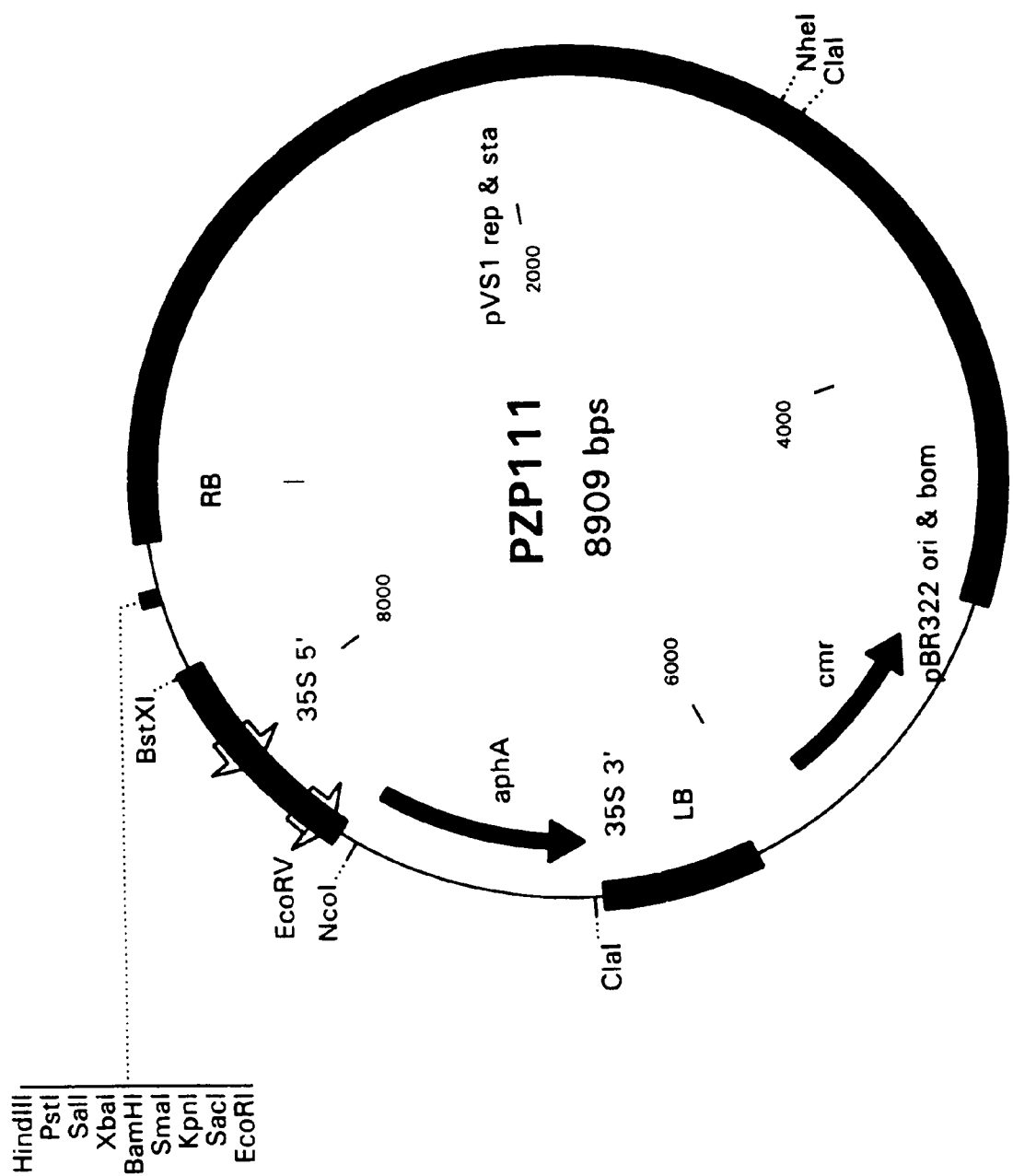
FIG. 6B is a diagrammatic representation of the backbone vector pPZP111 (Hajdukiewicz et al, 1994).
Figure 6C:
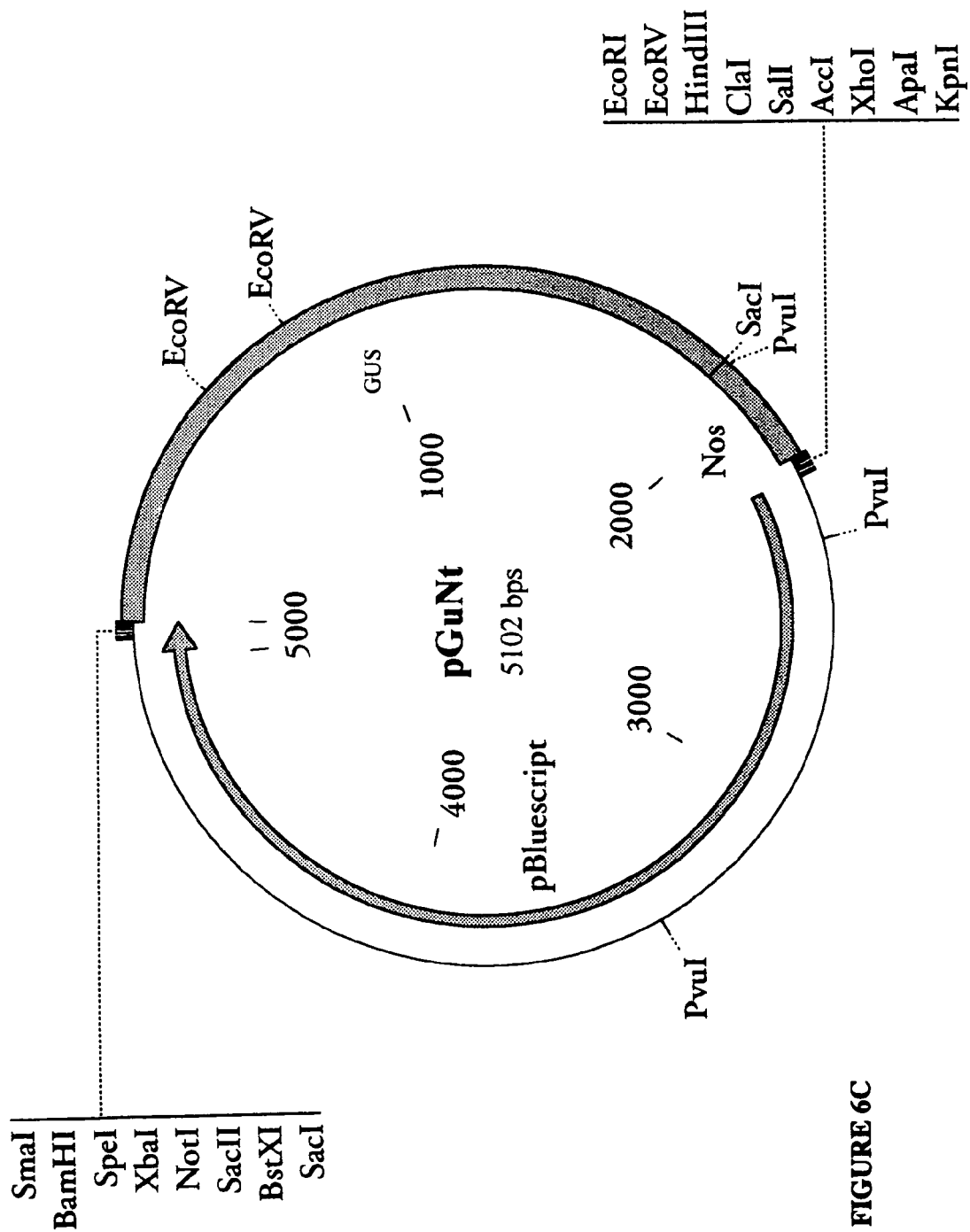
FIG. 6C is a diagrammatic representation of the vector pGuNt.

These chimeric constructs were then successfully ligated into the polylinker of the binary vector backbone pPZP111 (Hajdukiewicz et al, 1994), for use in plant transformation. A range of these constructs, comprising pGEL-1 is shown in FIGS. 6A(i) to 6A(xii). The backbone vector pPZP111 is shown in FIG. 6B. The bluescript vector comprising GUS and the NOS terminator (pGuNt) is shown in FIG. 6C.

(b) Transformation and Regeneration of Tobacco

The characterization of pGEL-1 was carried out using tobacco as the model plant system. Tobacco transformation was carried out as described by Svab et al. (1995). Multiple independent transgenic lines were generated with each of the binary constructs.

(c) Generation of T2 Lines

Figure 7:
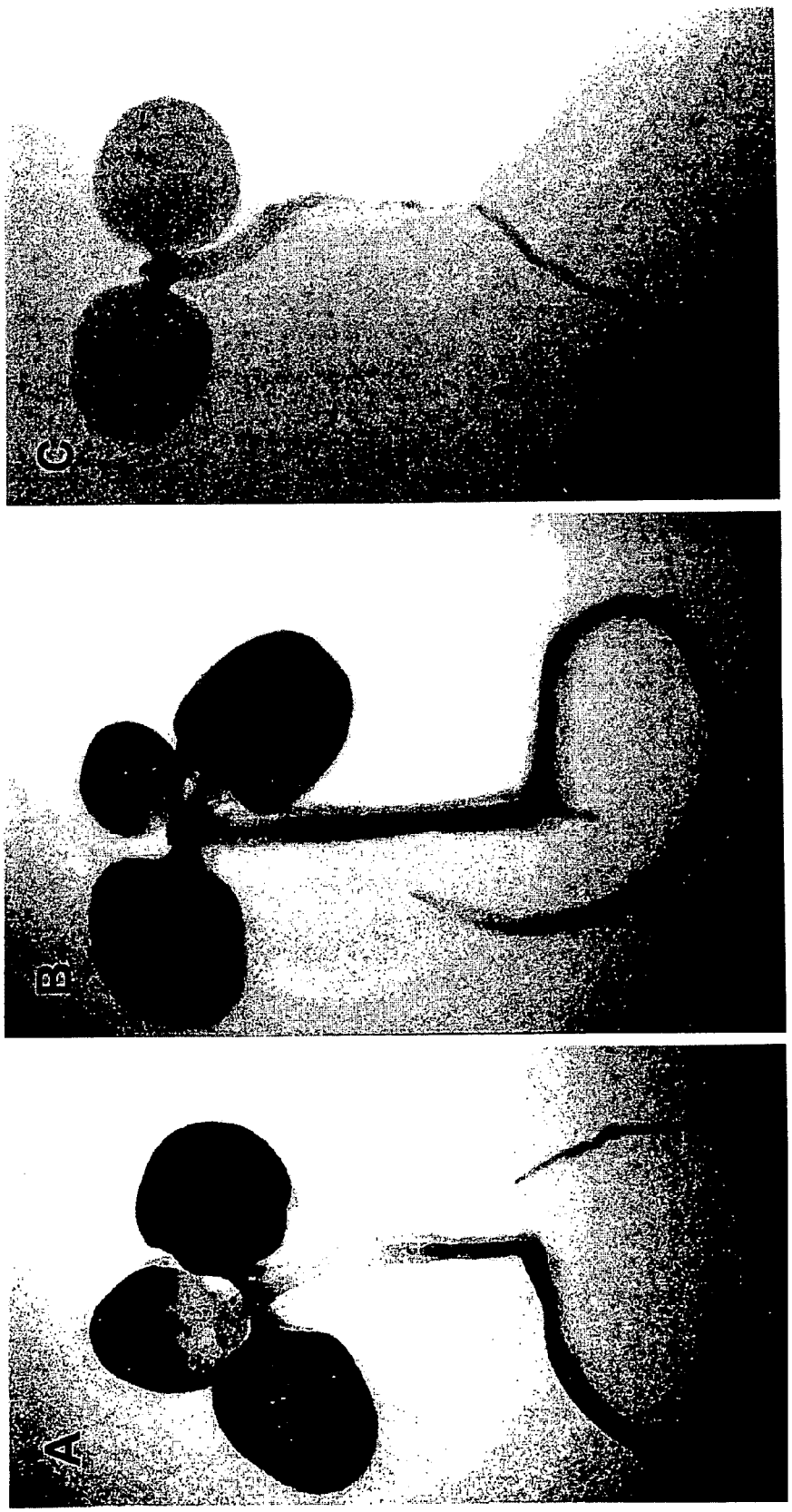
FIG. 7 are photographic representations showing (A) and (B) transgenic tobacco lines containing pGEL-1:GUS gene assayed to visualise GUS activity; and (C) wild-type tobacco stained for GUS (negative control).
Figure 8A:
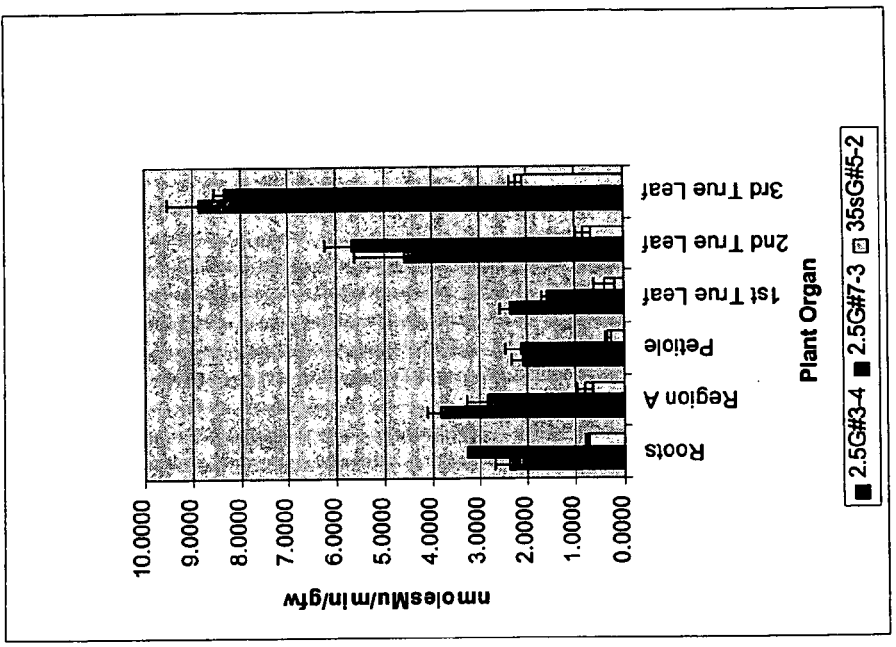
FIGS. 8(a) and (b) are graphical representations showing GUS activity in young tobacco plants, transformed with pGEL-1:GUS and CaMV35S:GUS constructs. 2.5G#3-4 and 2.5G#7-3 are two independent transgenic lines containing full length promoter, pGEL-1, fused to the GUS gene; 35SG#5-2 is a transgenic line containing CaMV35S promoter fused to the GUS gene. (A) is GUS activity measured as nmoles Mu per minute per mg protein. (B) is GUS activity measured as nmoles Mu per minute per gram fresh weight (gfw) of pant material. Mu is equal to 4-methyl-umbrelliferone.
Figure 8B:
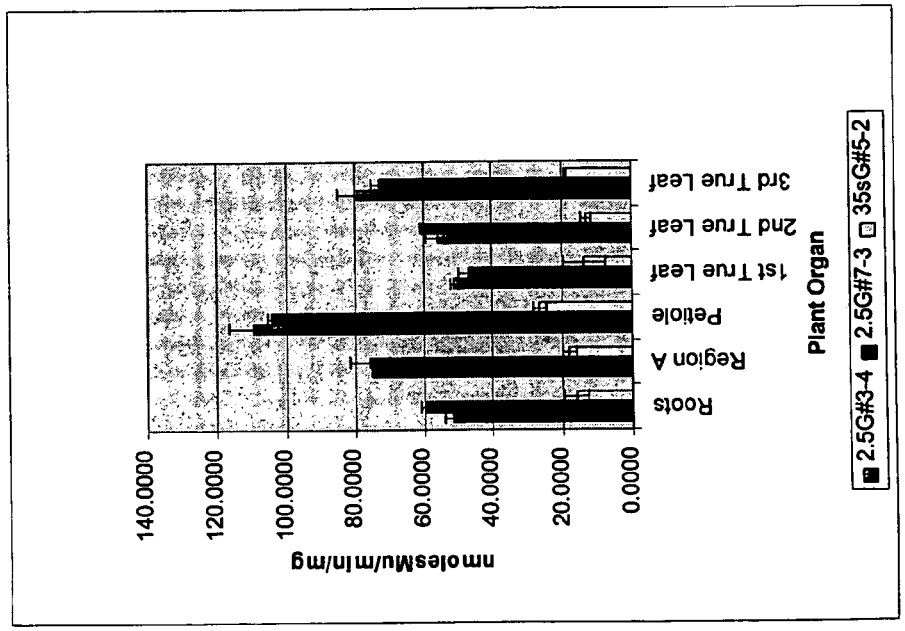
Figure 9A:
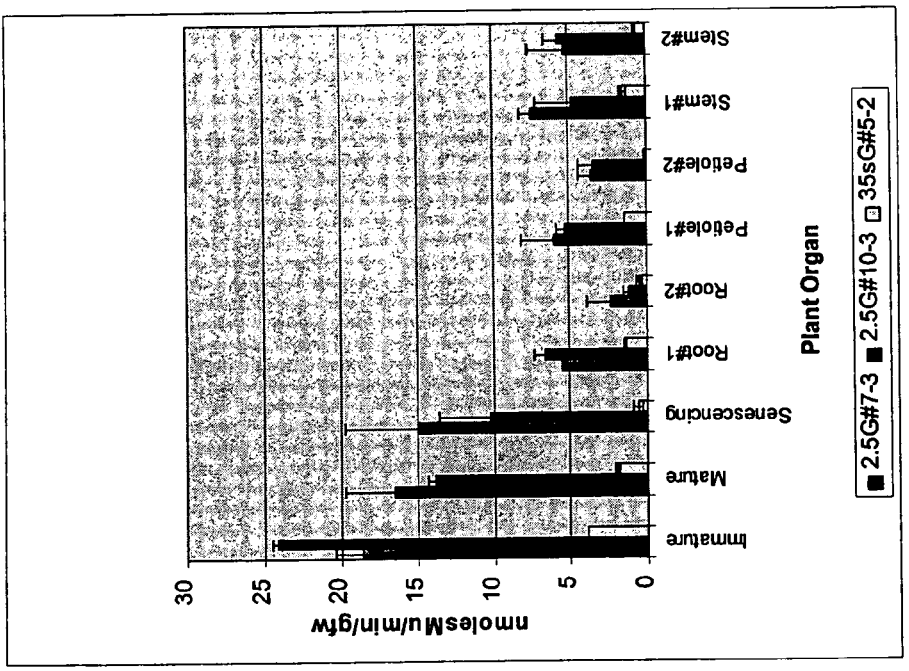
FIG. 9 is a graphical representation showing quantitative analysis of pGEL-1 and 35S cauliflower mosaic virus (CaMV) promoter: GUS fusions in mature vegetative transgenic tobacco. (A) expressed as nmoles of Mu produced per minute per mg protein; (B) expressed as nmoles of Mu produced per minute per gram fresh weight (gfw) of plant material.
Figure 9B:
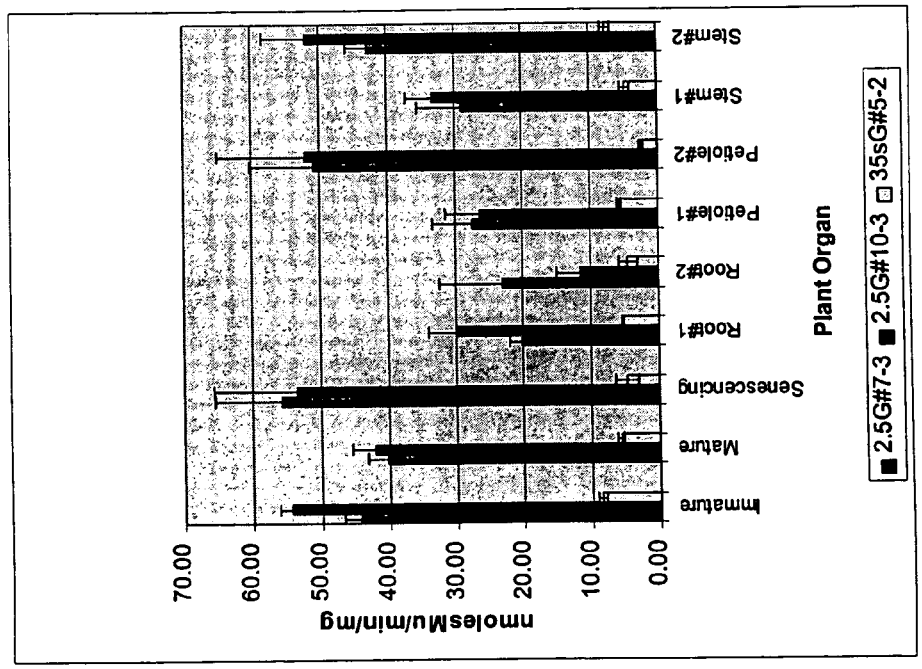
Figure 10B:
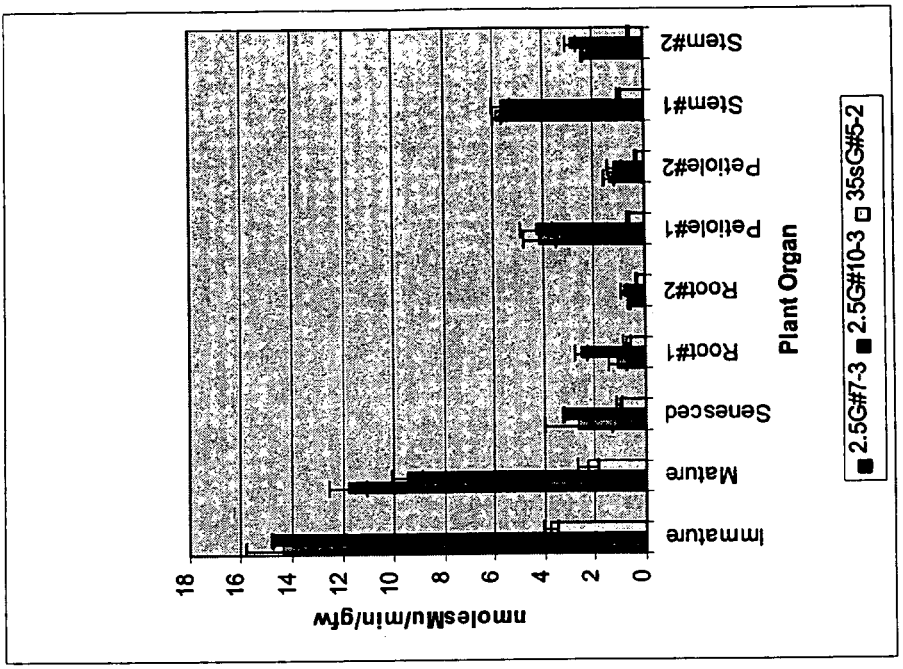
FIG. 10 is a graphical representation showing a quantitative analysis of pGEL1 and 35SCaMV promoter:GUS fusions in mature flowering transgenic tobacco. (A) expressed as nmoles of Mu produced per minute per mg protein; (B) expressed as nmoles of Mu produced per minute per gram fresh weight (gfw) of plant material.
Figure 10A:
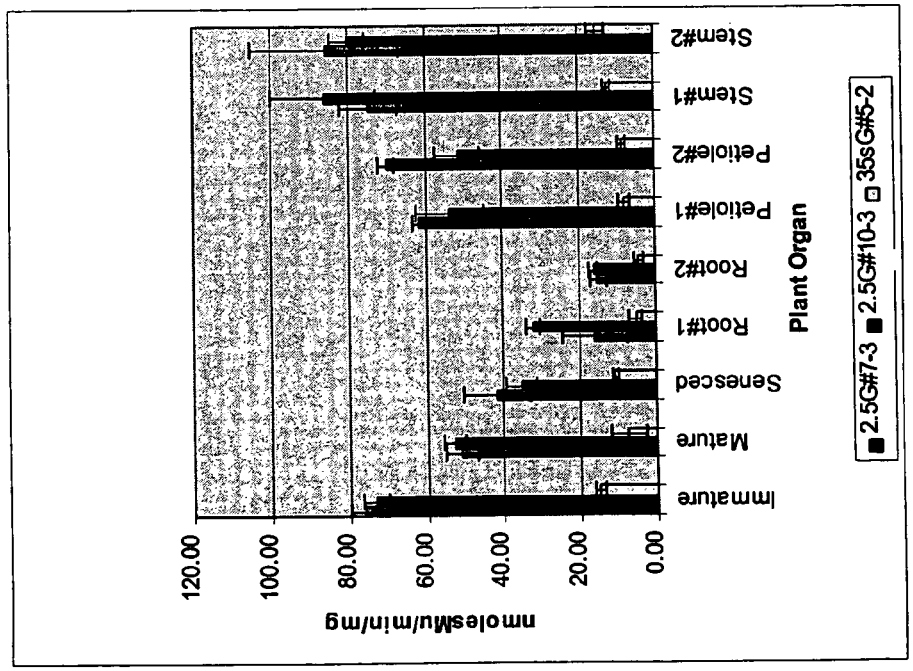

T2 lines were generated from selected T1 lines by self-pollination. Tissue of young transgenic tobacco lines, containing the pGEL-1:GUS gene construct, were histochemically assayed to visualise GUS activity. Very intense levels of histochemical stain indicate high levels of expression of the GUS gene in tissues of young plants (FIGS. 7A, B).

(d) Quantitative Analysis of pGEL-1

To quantify levels of expression of the GUS gene under control of pGEL-1 and compare it to levels obtained using the CaMV35S promoter, quantitative analysis was carried out on two independent transgenic T2 tobacco lines (3-4 and 7-3) containing the pGEL-1:GUS genetic construct and one transgenic T2 line (5-2) containing the 35S:GUS genetic construct. Assays were performed according to the method of Jefferson (1987) on different plant tissues including root, stem, petiole and first, second and third true leaves. The results indicated that constructs containing pGEL-1 drive levels of expression two to five times higher than that obtained using the 35S promoter (see FIGS. 8, 9, 10 and 11).

(e) Deletion Analysis

Figure 11:
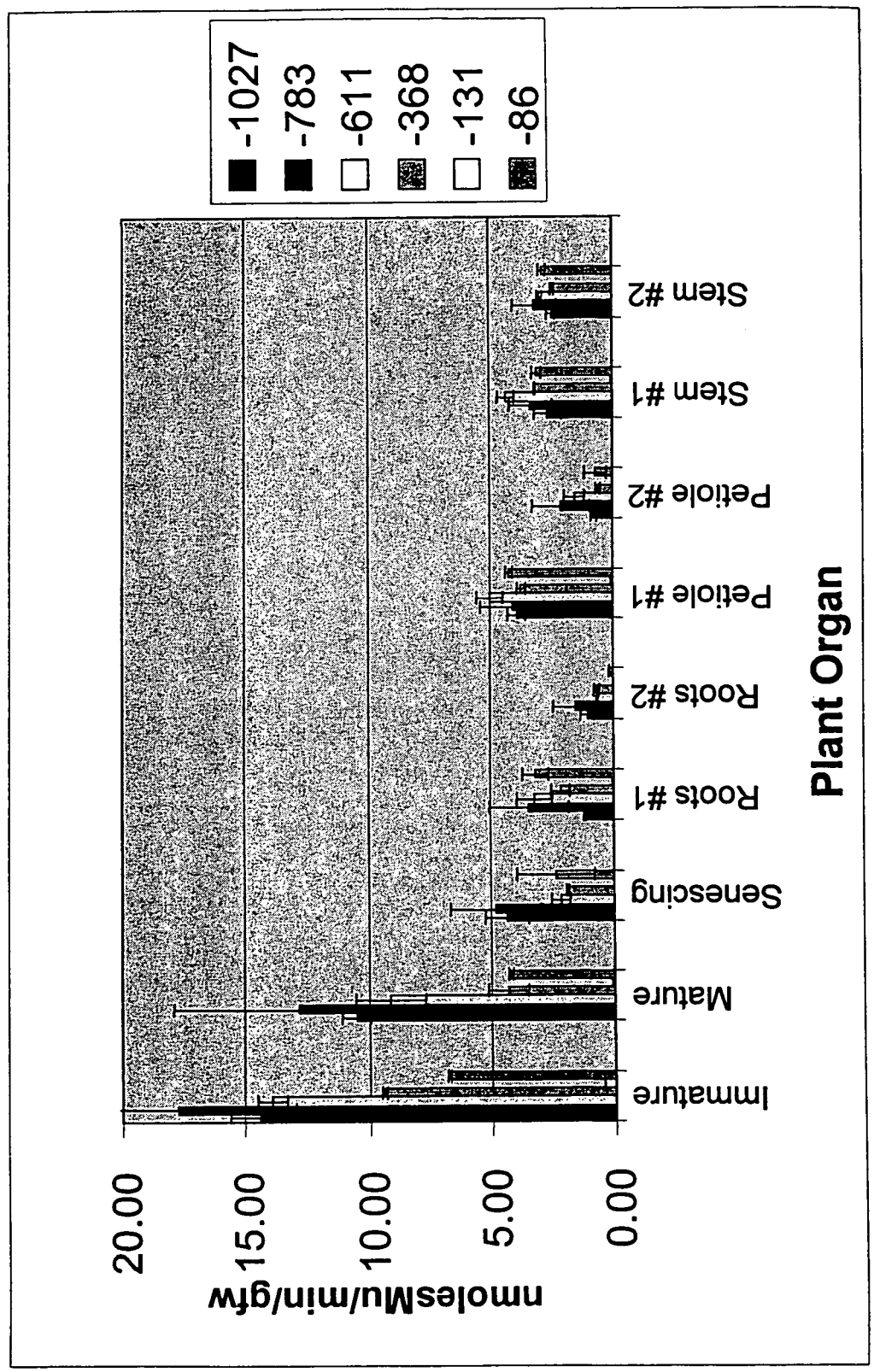
FIG. 11 is a graphical representation showing quantitative analysis of a range of deletions of pGEL-1:GUS fusions in mature vegetative transgenic tobacco. Deletions range from 1.027 by to 86 bp. Activity is expressed as nmoles of Mu produced per minute per gram fresh weight (gfw) of plant material.
Figure 12:
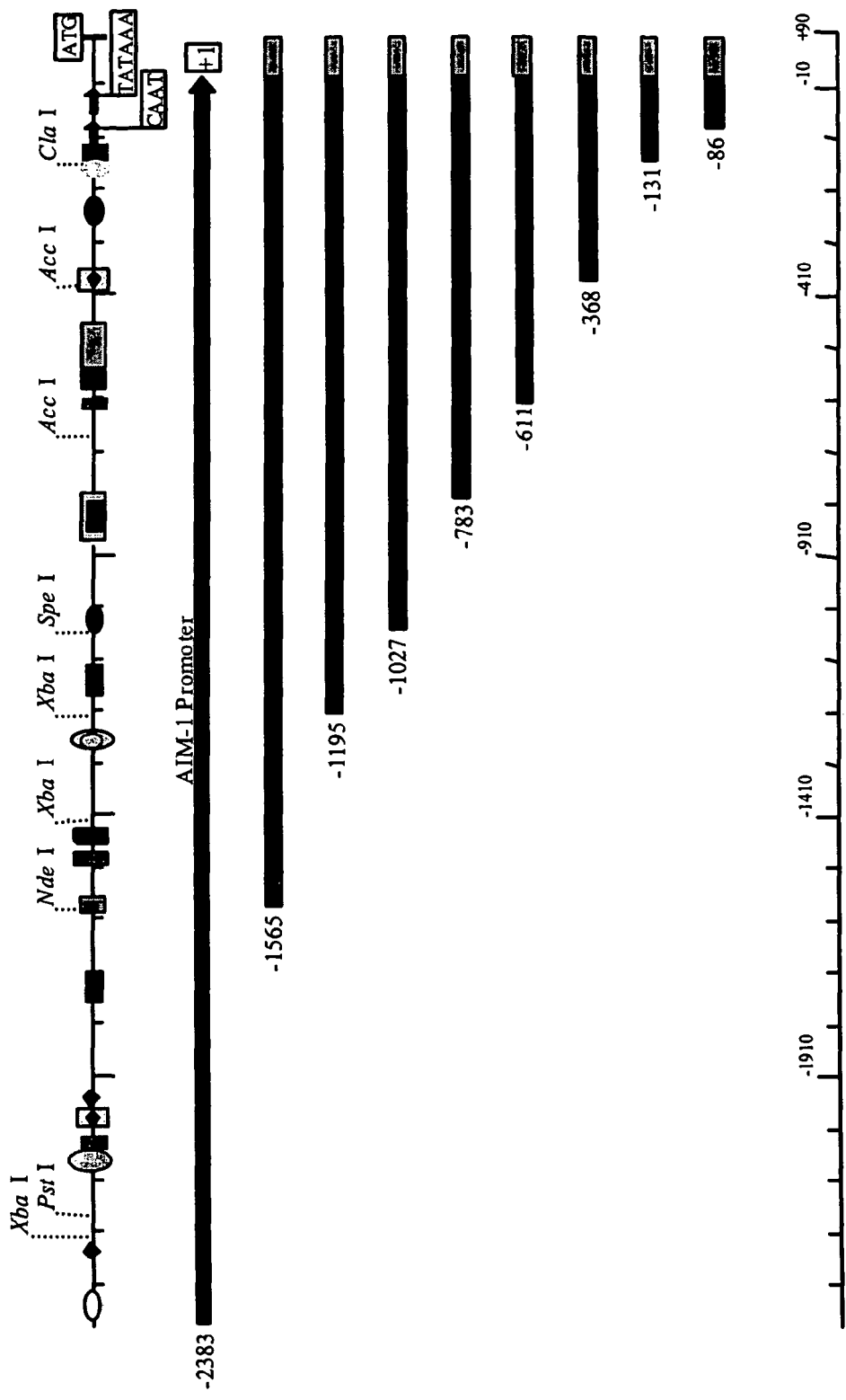
FIG. 12 is a diagrammatic representation showing deletions in pGEL-1.

Several deletions of the pGEL-1 promoter regions were made and fused to the GUS gene ranging from 1.027 by to 86 bp. FIG. 11 shows the GUS activity measures performed in several plant organs at different developmental stages. It is observed that there is a general decline in activity in the shorter promoter constructs in immature and mature leaf tissue. Nevertheless. the decrease in activity is not so evident in other tissues.

Example 6

Transformation Procedures

The promoter is introduced into a range of plants generally from within a construct. Genetic material is introduced into the *Agrobacterium tumefaciens* strain AGL0 by adding 5 µg of plasmid DNA to 100 µl of competent AGL0 cells prepared by inoculating a 50 ml culture of MG/L (Garfinkel and Nester, 1980). These are cultured and grown for 16 hours with shaking at 28° C. The cells are then pelleted and resuspended in 0.5 ml of 85% v/v 100 mM $CaCl_2$/15% v/v glycerol. The DNA-*Agrobacterium* mixture is frozen by incubation in liquid $N_2$ for 2 minutes and then allowed to thaw by incubation at 37° C. for 5 minutes. The DNA/bacterial mix is then placed on ice for a further 10 minutes. The cells are then mixed with 1 ml of LB (Sambrook et al., 1989) media and incubated with shaking for 16 hours at 28° C. Cells of *A. tumefaciens* carrying genetic material are selected on LB agar plates containing 10 µg/ml gentamycin or other suitable selection such as another antibiotic or a herbicide. The presence of genetic material is confirmed by Southern analysis of DNA isolated from the gentamycin-resistant transformants or any other selectable molecule such as another antibiotic or a herbicide.

Petunia Transformations (a) Plant Material

Leaf tissue from mature plants is treated in 1.25% w/v sodium hypochlorite for 2 minutes and then rinsed three times in sterile water. The leaf tissue is then cut into 25 mm² squares and precultured on MS media (Murashige and Skoog, 1962) supplemented with 0.05 mg/l kinetin and 1.0 mg/l 2,4-dichlorophenoxyacetic acid (2,4-D) for 24 hours.

(b) Co-Cultivation of *Agrobacterium* Tissue

*Agrobacterium tumefaciens* strain AGL0 containing genetic material is maintained at 4° C. on MG/L agar plates with 100 mg/l gentamycin. A single colony is grown overnight in liquid medium containing 1% w/v Bacto-peptone, 0.5% w/v Bacto-yeast extract and 1% w/v NaCl. A final concentration of $5\times10^8$ cells/ml is prepared the next day by dilution in liquid MS medium containing B5 vitamins (Gamborg et al, 1968) and 3% w/v sucrose (BPM). The leaf discs were dipped for 2 minutes into BPM containing AGL0/genetic material. The leaf discs are then blotted dry and placed on co-cultivation media for 4 days. The co-cultivation medium consists of SH medium (Schenk and Hildebrandt, 1972) supplemented with 0.05 mg/l kinetin and 1.0 mg/l 2,4-D and included a feeder layer of tobacco cell suspension spread over the co-cultivation medium with a filter paper placed on top of the tobacco cell suspension.

(c) Recovery of Transgenic Plants

After co-cultivation, the leaf discs are transferred to a selection medium (MS medium supplemented with 3% w/v sucrose, a-benzylaminopurine (BAP) 2 mg/l, 0.5 mg/l a-naphthalene acetic acid (NAA), kanamycin 300 mg/l, 350 mg/l cefotaxime and 0.3% w/v Gelrite Gellan Gum (Schweizerhall). Regenerating explants are transferred to fresh selection medium after 4 weeks. Adventitious shoots which survive the kanamycin selection are isolated and transferred to BPM containing 100 mg/l kanamycin and 200 mg/l cefotaxime for root induction. All cultures are maintained under a 16 hour photoperiod (60 µmol. $m^{-2}$ $s^{-1}$ cool white fluorescent light) at 23±2° C. When roots reach 2-3 cm in length the transgenic petunia plantlets are transferred to autoclaved Debco 51410/2 potting mix in 8 cm tubes. After 4 weeks, plants are replanted into 15 cm pots, using the same potting mix, and maintained at 23° C. under a 14 hour photoperiod (300 µmol. $m^{-2}$ $s^{-1}$ mercury halide light).

Example 7

Transformation of *Dianthus caryophyllus* a. Plant Material

*Dianthus caryophyllus*, (cv. Crowley Sim, Red Sim, Laguna) cuttings are used in this experiment. The outer leaves are removed and the cuttings are sterilized briefly in 70% v/v ethanol followed by 1.25% w/v sodium hypochlorite (with Tween 20) for 6 minutes and rinsed three times with sterile water. All the visible leaves and axillary buds are removed under the dissecting microscope before co-cultivation.

b. Co-Cultivation of *Agrobacterium* and *Dianthus* Tissue

*Agrobacterium tumefaciens* strain AGL0 containing a genetic construct encoding a cytochrome P450 monooxygenase and optionally an associated protein as herein described is maintained at 4° C. on MG/L (Garfinkel and Nester, 1980) agar plates with 100 mg/l gentamycin. A single colony is grown overnight in liquid MG/L broth and diluted to $5\times10^8$ cells/ml the next day before inoculation. *Dianthus* tissue is co-cultivated with *Agrobacterium* on MS medium (Murashige and Skoog, 1962) supplemented with 3% w/v sucrose, 5 mg/l a-naphthalene acetic acid (NAA), 20 µM acetosyringone and 0.8% w/v Difco Bacto Agar (pH 5.7).

c. Recovery of Transgenic *Dianthus* Plants

Co-cultivated tissue is transferred to MS medium supplemented with 1 mg/l benzylaminopurine (BAP), 0.1 mg/l NAA, 150 mg/l kanamycin, 500 mg/l ticarcillin and 0.8% w/v Difco Bacto Agar (selection medium). After three weeks, explants are transferred to fresh selection medium and care is taken at this stage to remove axillary shoots from stem explants. After 6-8 weeks on selection medium, healthy adventitious shoots are transferred to hormone free MS medium containing 3% w/v sucrose, 150 mg/l kanamycin, 500 mg/l ticarcillin, 0.8% w/v Difco Bacto Agar. At this stage, GUS histochemical assay (Jefferson, 1987) and/or NPT II dot-blot assay (McDonnell et al, 1987) are used to identify transgenic shoots. Transgenic shoots are transferred to MS medium supplemented with 3% w/v sucrose, 500 mg/l ticarcillin and 0.4% w/v Gelrite Gellan Gum (Schweizerhall) for root induction. All cultures are maintained under a 16 hour photoperiod 120 µE cool white fluorescent light) at 23±2° C. When plants are rooted and reached 4-6 cm tall they are acclimatised under mist. A mix containing a high ratio of perlite (75% or greater) soaked in hydroponic mix (Kandreck and Black, 1984) is used for acclimation, which typically lasts 4-5 weeks. Plants are acclimatised at 23° C. under a 14 hour photoperiod (200 µE mercury halide light).

Example 8

Transformation of *Rosa hybrida*

1. *Rosa hybrida* cv Royalty

Plant tissues of the rose cultivar Royalty are transformed according to the method disclosed in PCT/AU91/04412, having publication number WO92/00371.

2. *Rosa hybrida* cv Kardinal a. Plant Material

Kardinal shoots are used. Leaves are removed and the remaining shoots (5-6 cm) are sterilized in 1.25% w/v sodium hypochlorite (with Tween 20) for 5 minutes followed by three rinses with sterile water. Isolated shoot tips are soaked in sterile water for 1 hour and precultured for 2 days on MS medium containing 3% w/v sucrose, 0.1 mg/l BAP, 0.1 mg/l kinetin, 0.2 mg/l Gibberellic acid, 0.5% w/v polyvinyl pyrrolidone and 0.25% w/v Gelrite Gellan Gum, before co-cultivation.

b. Co-Cultivation of *Agrobacterium* and *Rosa* Shoot Tissue

*Agrobacterium tumefaciens* strains ICMP 8317 (Janssen and Gardner, 1989) and AGL0, containing genetic constructs comprising pGEL-1 and optionally a structural gene operably linked thereto are maintained at 4° C. on MG/L agar plates with 100 mg/l gentamycin. A single colony from each *Agrobacterium* strain is grown overnight in liquid MG/L broth. A final concentration of $5 \times 10^8$ cells/ml is prepared the next day by dilution in liquid MG/L. Before inoculation, the two *Agrobacterium* cultures are mixed in a ratio of 10:1. A longitudinal cut is made through the shoot tip and an aliquot of 2 µl of the mixed *Agrobacterium* cultures is placed as a drop on the shoot tip. The shoot tips are co-cultivated for 5 days on the same medium used for preculture.

*Agrobacterium tumefaciens* strain AGL0 is maintained at 4° C. on MG/L agar plates with 100 mg/l kanamycin. A single colony from each *Agrobacterium* strain is grown overnight in liquid MG/L broth. A final concentration of $5 \times 10^8$ cells/ml is prepared the next day by dilution in liquid MG/L.

c. Recovery of Transgenic *Rosa* Plants

After co-cultivation, the shoot tips are transferred to selection medium. Shoot tips are transferred to fresh selection medium every 3-4 weeks. Galls observed on the shoot tips are excised when they reached 6-8 mm in diameter. Isolated galls are transferred to MS medium containing 3% w/v sucrose, 25 mg/l kanamycin, 250 mg/l cefotaxime and 0.25% w/v Gelrite Gellan Gum for shoot formation. Shoots regenerated from gall tissue are isolated and transferred to selection medium. GUS histochemical assay and callus assay are used to identify transgenic shoots. Transgenic shoots are transferred to MS medium containing 3% w/v sucrose, 200 mg/l cefotaxime and 0.25% w/v Gelrite Gellan Gum for root induction. All cultures are maintained under 16 hour photoperiod (60 µE cool white fluorescent light) at 23±2° C. When the root system is well developed and the shoot reached 5-7 cm in length the transgenic rose plants are transferred to autoclaved Debco 514110/2 potting mix in 8 cm tubes. After 2-3 weeks plants are replanted into 15 cm pots using the same potting mix and maintained at 23° C. under a 14 hour photoperiod (300 µE mercury halide light). After 1-2 weeks potted plants are moved to glasshouse (Day/Night temperature: 25-28° C./14° C.) and grown to flowering.

Example 9

Transformation of *Chrysanthemum morifolium* a. Plant Material

*Chrysanthemum morifolium* (cv. Blue Ridge, Pennine Chorus) cuttings are obtained. Leaves are removed/from the cuttings, which are then sterilized briefly in 70% v/v ethanol followed by 1.25% w/v sodium hypochlorite (with Tween 20) for 3 minutes and rinsed three times with sterile water. Internodal stem sections are used for co-cultivation.

b. Co-Cultivation of *Agrobacterium* and *Chrysanthemum* Tissue

*Agrobacterium tumefaciens* strain LBA4404 (Hoekema et al, 1983), containing a genetic construct of the present invention is grown on MG/L agar plates containing 50 mg/l rifampicin and 10 mg/l gentamycin. A single colony from the *Agrobacterium* is grown overnight in the same liquid medium. These liquid cultures are made 10% v/v with glycerol and 1 ml aliquots transferred to the freezer (−80° C.). A 100-200 µl aliquot of each frozen *Agrobacterium* is grown overnight in liquid MG/L containing 50 mg/l rifampicin and 10 mg/l gentamycin. A final concentration of $5 \times 10^8$ cells/ml is prepared the next day by dilution in liquid MS containing 3% w/v sucrose. Stem sections are co-cultivated with *Agrobacterium* in co-cultivation medium for 4 days.

c. Recovery of Transgenic *Chrysanthemum* Plants

After co-cultivation, the stem sections are transferred to selection medium. After 3-4 weeks, regenerating explants are transferred to fresh medium. Adventitious shoots which survive the kanamycin selection are isolated and transferred to MS medium containing kanamycin and cefotaxime for shoot elongation and root induction. All cultures are maintained under a 16 hour photoperiod (80 µE cool white fluorescent light) at 23±2° C. Leaf samples are collected from plants which rooted on kanamycin and Southern blot analysis is used to identify transgenic plants. When transgenic chrysanthemum plants reach 4-5 cm in length, they are transferred to autoclaved Debco 51410/2 potting mix in 8 cm tubes. After 2 weeks, plants are replanted into 15 cm pots using the same potting mix and maintained at 23° C. under a 14 hour photoperiod (300 µE mercury halide light). After 2 weeks potted plants are moved to glasshouse (Day/Night temperature: 25-28° C./14° C.) and grown to flowering.

Example 10

Bombardment of Plant Tissue with Genetic Material Comprising pGEL-1 Operably Linked to a Gene of Interest The aim of these experiments is to introduce genetic constructs comprising pGEL-1 into plant tissue such as petals and then to screen for at least transient expression. The gene bombardment protocol is initially optimised using the reporter vector pGEL-1:GUS. GUS expression is assayed using the method described by Jefferson et al (1992). Efficiency of the transformation is measured by the mean number of blue spots per petal bombardment. The parameters examined during these initial optimisation experiments are target distance, bombardment pressure and petal developmental stage.

Plasmid DNA is obtained from *E. coli* using a standard alkaline lysis procedure with and without additional procedures for purification of the resultant DNA (Sambrook et al, 1989). The DNA is prepared for bombardment by combining various amounts of tungsten particle solution with DNA. After vortexing, the particles are precipitated with $CaCl_2$ and spermidine. After removing a portion of the supernatant, the tungsten suspension was vortexed and an aliquot removed for bombardment.

In this experiment, white petunia flowers are used for bombardment. Petunia plants having other colours may also be used. The device used for bombardment is the particle inflow gun developed by Finer et al (1992) which propels tungsten particles directly in a stream of helium towards the target. The petal is placed in a petri dish containing filter paper moistened with appropriate medium. Each petal preparation is bombarded with one of:

a) vector containing pGEL-1 alone; or b) vector containing pGEL-1 operably linked to GUS (or other gene of interest);

c) vector containing a GUS control (or other gene of interest).

In some cases, the vector containing the GUS control is bombarded simultaneously with either or both types of vectors containing pGEL-1.

The optimum petal distance and helium pressure found during these experiments is 12.5 cm shelf height and 1000 Kpa, respectively. Optimum DNA is about 2-5 ng DNA/petal. A negative control containing tungsten particles only is also included.

The success of the bombardment is analysed by the presence of blue spots after overnight incubation of the bombarded petal in the presence of GUS substrate.

Example 11

Optimization of Microprojectile Bombardment of "Sunrise Solo" Somatic Embryos

A gene gun (based on the particle inflow gun; Finer et al, 1992) is used for bombardment. Tungsten particles (0.7 µm, Biorad) are used as microprojectiles; 16-20 mg tungsten is washed with ethanol and then washed three times with sterile double distilled water (ddH$_2$O) before suspension in 200 µl double distilled water. For preparation of microprojectiles, 100 µg/l tungsten suspension is mixed with 1 µg/l plasmid DNA, 2.5 mM CaCl$_2$ and 100 mM spermidine-free base. The plasmid DNA used is, for example, p2.5GuNt (pGEL-1 promoter::GUS gene::Nos Terminator in a pBluescript backbone). However, any pGEL-1 construct may be used. For example, GUS may, of course, be replaced by a gene of interest. All solutions are kept on ice. The suspension is thoroughly mixed, then allowed to settle on ice for 5 minutes before 100 µg/l of the supernatant is removed and discarded. The remaining suspension is raked several times on the rack immediately before using 4 µl of the mixture for each bombardment. A protective buffle of nylon mesh (Franks and Birch, 1991) is placed over the tissue during bombardment. The tissues are bombarded using various pressures and distances. The bombarded embryos are then transferred onto a half-strength MS medium and incubated for 48 hours. After this period glucoronidase (GUS) activity is assayed histochemically by incubating the embryos in 8-bromo-4-chloro-3-indolyl glucoronide (X-gluc) solution overnight at 37° C. (Jefferson, 1987). Transient expression is assayed 12 hours after incubation and measured as total blue foci count per shot area.

In experiment one, somatic embryos are placed on osmoticum medium (half strength MS salts and vitamins, 0.2 M mannitol and 0.5% w/v phytagel) for a total of six hours (three hours before and after bombardment). A protective buffle of nylon mesh (Franks and Birch, 1991) is placed over the tissue during bombardment. The tissues are bombarded using four different pressures (1000, 1500, 1800 and 2000 KPa). The distance of the target tissue from the filter unit containing the microprojectiles is 17.5 cm. The bombarded embryos are then transferred on a half-strength MS medium and incubated for 48 hours. After this period, GUS activity is assayed histochemically by incubating the embryos in 5-bromo-4-chloro-3-indolyl glucoronide (X-gluc) solution overnight at 37° C. (Jefferson, 1987). Transient expression is assessed as total blue foci count per shot area.

In a second experiment, the somatic embryos produced from immature fruits are transferred onto a sterile filter paper (overlaided onto the medium) and are spread firmly over the surface of the filter paper with a sterile metal spatula in order to squash the embryos (Gonsalves et al, 1997). The embryogenic cells are allowed to proliferate for another four to six weeks and are re-spread over the filter paper and, bombarded three days later as described above.

Three distances of the target somatic embryos from the filter containing the microprojectiles are tested. These distances are 17.5, 15.0 and 12.5 cm, and the pressure is 1000 KPa. The target tissues are bombarded following the procedure previously described.

Example 12

Papaya Transformation

Papaya tissue is transformed with genetic material using the following protocol. Growing temperatures are at 22-35° C.

1. Somatic Embryo Induction

Embryos are cut from immature (90 days old) papaya seeds and cultured on somatic embryo induction medium (SEIM) for 4-6 weeks or 3-4 months. The embryos are sub-cultured every 2 weeks on fresh SEIM. Seven to 12 embryos are then squashed using a metal spatula on 3 MM filter paper, 3 days before shooting on SEIM.

2. Shooting

Embryos are placed, while still on the filter paper, onto osmoticum medium (OSM). Conveniently, this is done in the morning. The embryos are maintained on OSM for at least 8 hours before, during and after shooting.

a) Conditions for shooting are as follows:

| Pressure: | 1000 KPa |
|---|---|
| Distance target to filter: | 12.5 cm |
| Pulse time: | 50 msec | b) Tungsten Particles (0.7 µm): Particles are washed in ethanol 3 times, then 3 times in sterile double distilled H$_2$O (ddH$_2$O) and then resuspended to a final concentration of 100 µg/µl in ddH$_2$O.

c) DNA preparation:

The following components are added together:

50 µl Tungstein (100 µg/µl)

20 µl DNA (500-1000 ng total) [pPZP2.5GuNt or other suitable construct]

50 µl CaCl$_2$ (2.5 mM)

20 µl Spermidine (100 mM)

The latter two components are added in quick succession.

The mixture is allowed to sit for 5 min, for the tungsten to collect on the bottom and approximately 110 µl is removed from the top and discarded. This gives enough for 5 shots. Shots are made as quickly as possible because the DNA dissociates from tungsten.

d) Shooting:

Prior to shooting, the gun is swabbed together with the bench with alcohol. Tungsten-DNA is thoroughly resuspended and 4 µl is pipetted into the filter units Working aseptically, the baffle is placed onto the medium containing the tissue and slightly pressed into the agar. The filter is then screened into the gun. The gun chamber is evacuated until the vacuum gauge approximately reads −29 mmHg and the fire button is pressed. The vacuum is immediately released and the tissue removed.

3. Recovery

Embryos are placed, still on the filter paper onto recovery medium (RM) after shooting for 5-7 days.

4. Pre-Selection

Embryos are removed from the filter paper and placed onto PSM for 1 month and sub-cultured every 2 weeks.

5. Full Selection

All embryos are placed onto a full selection medium (FSM) and sub-culture every 2-3 weeks. Tissue which is growing well is placed onto to FSM with 300 mg/l. kanamycin for two sub-cultures. Surviving tissue is placed onto EGM.

6. Regeneration a) Embryo Germination.

Embryos are placed onto embryo germination medium (EGM) with 150 mg/l kanamycin for 3-4 months (or longer until germinating clumps emerge). The embryos are sub-cultured every 2-4 weeks and maintained until green tissue emerges (1-2 mm).

b) Single Shoot Growing.

Green tissue is placed onto full strength single shoot growing medium (SSGM) until a whole plant is obtained. Tissue is sub-cultured every month.

7. Micropropagation a) Shoot Multiplication.

Stems are cut and leaves and roots removed and placed onto shoot multiplication medium (SMM) for 2 weeks up to one month.

b) Root Induction.

New emerging shoots are cut from the central shoot and placed onto root induction medium (RIM) for 3 days.

c) Shoots are placed onto full strength SSGM and sub-cultured every month until formation of a full grown plant.

d) The plant can be kept longer (up to one year) in culture using a minimal growth medium containing full strength SSGM plus 1% w/v fructose instead of glucose.

8. Potting Out

The plants are planted out into Styrofoam seedling trays using steam sterilised soil. After 3 days, the seedling trays are drenched with a fungicide (e.g. Dithane M45 or Alliette). These plants are placed in a humidifying chamber with the following acclimatisation conditions:

| | |
|---|---|
| 1st week | 90-100% humidity |
| 2nd week | 70% humidity |
| 3rd week | 60% humidity |
| 4th week | open door a bit |

The plants are left in the chamber until the leaves become shiny. Plants are gently watered with distilled water when needed.

The Following Media are Used:

1. Somatic Embryo Induction Media (SEIM)

| | 1 liter |
|---|---|
| ½ strength MS salts | 2.17 g |
| MS Vitamins | 1 ml (1000x stock) |
| 2,4-D | 10 ml (1 mg/ml stock) |
| Glutamine | 20 ml (5 mg/ml stock) |
| Myo inositol | 10 ml (1 mg/ml stock) |
| thiamine HCl | 10 ml (1 mg/ml stock) |
| Sucrose | 30g |
| Agar | 8 g |
| or Phytagel | 5 g |
| pH 6.5-7 | |
| MS Vitamins(1000x): Stored frozen | 100 ml |
| Thiamine-HCl | 10 mg |
| Pyridoxine-HCl | 50 mg |
| Nicotinic acid | 50 mg |
| Glycine | 200 mg |
| Myo-inositol | 10 g |

2. Osmoticum Media (OSM)

| | 1 liter |
|---|---|
| ½ strength MS salts | 2.179 |
| ½ MS Vitamins | 500 µl (1000x stock) |
| Mannitol | 36.4 g |
| Agar | 8 g |
| or Phytagel | 5 g |
| pH 6.5-7 | |

3. Recovery Media (RM)

| | 1 liter |
|---|---|
| ½ strength MS salts | 2.17 g |
| ½ MS Vitamins | 500 µl (1000x stock) |
| Sucrose | 30 g |
| Agar | 8 g |
| or Phytagel | 5 g |
| pH 6.5-7 | |

4. Pre-Selection (PSM)

SEIM with 75 mg/l kanamycin (750 µl of a 100 mg/ml stock in 1 liter)

5. Full Selection Media (FSM)

SEIM with 150 mg/l kanamycin (1500 µl of a 100 mg/ml stock in 1 liter) or 300 mg/ml kanamycin (3000 µl of a 100 mg/ml stock in 1 liter)

7. Embryo Germination Media (EGM)

| | 1 liter |
|---|---|
| ½ Strength MS salts | 2.17 g |
| ½ MS Vitamins | 500 µl (1000x stock) |
| Kinetin | 0.25 µM (2.5 ml of a 100 µM stock) |
| IAA | 4.5 µM (45 ml of a 100 µM stock) |
| GA3 | 0.8 µM (8 ml of a 100 µM stock, filter sterilised, added after autoclaving) |
| Sucrose | 30 g |
| Agar | 8 g |
| or Phytagel | 5 g |
| pH 6.5-7 | |

After autoclaving add 1500 µl of a 100 mg/ml stock in 1 liter

8. Single Shoot Growing Media (SSGM)

| Full strength SSGM | 1 liter |
|---|---|
| De Fossard's Minerals | 80 ml (1X) |
| De Fossard's Vitamins | 50 ml (2X) |
| Sucrose | 30 g |
| Agar | 8 g |
| or Phytagel | 5 g |
| pH 6.5-7 | |

9. Shoot Multiplication Media (SMM)

| | 1 liter |
|---|---|
| De Fossard's Minerals | 80 ml (1X) |
| De Fossard's Vitamins | 50 ml (2X) |
| Sucrose | 30 g |
| 0.25 µM BAP | 2.5 ml of a 100 µM stock |
| 0.25 µM NAA | 250 µl of a 1000 µM stock |
| Agar | 8 g |
| or Phytagel | 5 g |
| pH 6.5-7 | |

10. Root Induction Media (RIM)

| | 1 liter |
|---|---|
| De Fossard's Minerals | 40 ml (1X) |
| De Fossard's Vitamins* | 50 ml (1X) |
| Sucrose | 30 g |
| 10 µM IBA | 10 ml of a 1000 µM stock |
| Agar | 8 g |
| or Phytagel | 5 g |
| pH 6.5-7 | |
| De Fossards Minerals (1X) | 2.4 liter |
| $NH_4NO_3$ | 300 ml |
| $KNO_3$ | 600 ml |
| $NaH_2PO_4 \cdot H_2O$ | 300 ml |
| $CaCl_2$ | 300 ml |
| (Ferric sodium salt) FeNaEDTA | 300 ml |
| $MgSO_4 \cdot 7H_2O$ | 300 ml |
| Micronutrients | 300 ml |
| Vitamins #6 (2X) | 2 liter |
| Inositol | 4.32 g |
| Nicotinic acids | 196 mg |
| Pyridoxine HCl (100 mg/ml) | 496 µl |
| Thiamine HCl | 539 mg |
| Biotin (50 mg/ml) | 200 µl |
| Folic acid (50 mg/ml) | 712 µl |
| Ca-Pantothenate (50 mg/ml) | 1910 µl |
| Riboflavin | 150.8 mg |
| Ascorbic acid (100 mg/ml) | 704 µl |
| Choline chloride (100 mg/ml) | 560 µl |
| Glycine (100 mg/ml) | 1504 µl |
| L-Cysteine HCl | 756 mg |
| Stock Solutions | g/liter |
| $NH_4NO_3$ | 160.1 (2 M) |
| $KNO_3$ | 101.11 (1 M) |
| $NaH2PO4 \cdot H_2O$ | 31.202 (0.23 M) |
| $CaCl_2$ | 59.46 (0.54 M) |
| (Ferric sodium salt) | |
| FeNaEDTA | 3.67 (0.01 M) |
| $MgSO4 \cdot 7H2O$ | 73.95 (0.3 M) |
| Micronutrients | 1 liter |
| $H_3Bo_3$ | 0.9276 (0.015 M) |
| $MnSO_4 \cdot 4H_2O$ | 2.2306 (0.01 M) |
| $ZnSO_4 \cdot 47H_2O$ | 1.1502 ($4 \times 10^{-3}$ M) |
| $CuSO_4 \cdot 5H_2O$ | 0.0374 ($1.5 \times 10^{-3}$ M) |
| Ammonium Molybdate | |
| $(NH_4)_6Mo_7O_{24} \cdot 4H_2O$ | 0.1236 ($1 \times 10^{-4}$ M) |
| $CoCl_2 \cdot 4H_2O$ | 0.0238 ($1 \times 10^{-4}$ M) |
| KCl | 0.0830 ($5 \times 10^{-4}$ M) |
| Vitamin Stocks | |
| Pyridoxine HCl (100 mg/ml) | 1.5 g/15 ml in $H_2O$/ETOH |
| Biotin (50 mg/ml) | 750 mg/15 ml dil HCl |
| Folic acid (50 mg/ml) | 750 mg/15 ml dil NaOH |
| Ca-Pantothenate (50 mg/ml) | 750 ml/15 ml $H_2O$ |
| Ascorbic acid (100 mg/ml) | 1.5 g/15 ml $H_2O$ |
| Choline chloride (100 mg/ml) | 1.5 g/15 ml $H_2O$ |
| Glycine (100 mg/ml) | 1.5 g/15 ml $H_2O$ |
| De Fossard media (full strength) contains (in 1 liter) | |
| $NH_4NO_3$ | 10 ml |
| $KNO_3$ | 20 ml |
| $NaH_2PO_4 \cdot H_2O$ | 10 ml |
| CaCl2 | 10 ml |
| FeNaEDTA | 10 ml |
| $MgSO_4 \cdot 7H_2O$ | 10 ml |
| Micronutrients | 10 ml |
| Vitamins #6 (1X) | 100 ml (50 ml of 2X) |

*De Fossards vitamins with no riboflavin

Example 13

Transformation of cotton, *Brassica* and *maize*

Genetic constructs comprising pGEL-1 or a functional derivative or homologue thereof operably linked to a gene of interest, such as, for example, a reporter gene, are introduced into cotton, *Brassica* (e.g. canola) and *maize*. Cotton is transformed using *Agrobacterium* using the method described in U.S. Pat. No. 5,004,863. *Brassica* sp are transferred using *Agrobacterium* using the method described in U.S. Pat. No. 5,188,958. Maize is transformed via immature embryos using the method described in U.S. Pat. No. 5,641,664. These plants may also be transformed using electroporation, biolistic procedures and polyethylene glycol amongst other methods.

Example 14

Transformation of Wheat, Barley and Rice

Wheat transformation was by the method of Karunaratne et al (1996) with slight modifications.

Target Tissue

Young caryopsis are dissected from spikes of *Triticum aestivum* L. cv. Hartog, approximately 12 to 14 days post anthesis and surface sterilised with 10% w/v Dairy-Chlor (100 g/l available chlorine). Immature embryos are isolated and cultured in dark on MS medium (Murashige and Skoog, 1962) supplemented with 2, 4-dichlorophenoxyacetic acid (10 µM). After 7 days of culture, the immature embryos are subjected to particle bombardment.

Microprojectile Bombardment

The genetic construct to be introduced into plant cells is precipitated onto tungsten particles (1.2 µm) as descried by Finer and McMullen (1990) with the following modifications. An aliquot of 25 µl of a 500 mg/ml suspension of tungsten particles (1.2 µm) in distilled water is taken in an eppendorf tube followed by stepwise addition of the following: 5 µl of plasmid DNA (5 µl), 25 µl of calcium chloride (2.5 M), 10 µl of spermidine (0.1 M). The contents in the tube is mixed by finger vortexing and kept on ice. After 5 min., 30 µl of the supernatant is discarded and 300 µl of ethanol (90%) is added and kept on ice after mixing the contents. After 1 min, the tube is centrifuged and all the supernatant discarded. The ethanol wash is repeated once and the DNA-coated tungsten is finally suspended in 300 μl of ethanol (90%). The DNA-coated tungsten particles (2 μl) are delivered to the target tissue using a particle inflow gun (Finer et al, 1992). The target tissue is placed on a shelf 14 cm from the screen of the filter holder, which carried a suspension of plasmid-DNA coated tungsten particles. After bombardment, the tissue is transferred to the original medium and cultured in the dark for 2 months with fortnightly subculture.

Plant Regeneration and Selection

Embryogenesis leading to plant regeneration is stimulated by transferring clumps of embryogenic callus to MS medium devoid of hormones and containing Phosphinotricin (PPT) at a concentration of 5 mg/l. After two weeks, PPT-resistant plants and callus is transferred to fresh medium and subcultured weekly. PPT-resistant plants which are 4-5 cm are transferred to soil and kept under water mist for two weeks. Plants are then transferred to larger pots and kept in the glasshouse under day and night temperature of 22° C. and 19° C., respectively.

Rice is transformed by the method of Abedinia et al (1997). Barley is transformed according to the method of Tingay et al (1997).

| Hormone stocks Hormone | Molecular Weight (g) | mg/l Stock | Concentration of stock |
|---|---|---|---|
| BAP | 225.2 | 22.6 | 100 μM |
| NAA | 186.2 | 186.2 | 1000 μM |
| IAA | 175.2 | 17.5 | 100 μM |
| GA3 | 346.4 | 34.6 | 100 μM |
| Kinetin | 215.2 | 21.5 | 100 μM |
| IBA | 203.23 | 203.2 | 1000 μM |

Example 15

Southern Analysis of Transgenic T2 Tobacco Lines

Genomic DNA (10 μg) was digested with EcoRI or BamHI restriction enzymes; separated in an electrophoresis gel and transferred to a Hybond™ (Amersham) Nylon membrane. The membrane was prehybridized and hybridized at high stringency following standard procedures (Sambrook et al, 1989). A DNA fragment containing the full GUS gene and Nos terminator was labelled with $^{32}P$ and used as a probe. After washing at high stringency the following results were observed:

a) The EcoRI lanes of lines 3-4, 7-3 and 10-3 show a single fragment of the expected 4.5 kb size indicating the intactness of the GEL-1:GUS:NosT construct in each of these lines.

b) The BamHI lanes of lines 3-4, 7-3 and 10-3 show single fragments of different sizes (one fragment per line) indicating the existence of a single copy of GUS:NosT construct in each of these lines.

c) The BamHI lane of lines 5-2 shows two bands indicating that this line contains two copies of the CaMV 35S:GUS:NosT portion of the construct.

Figure 13:
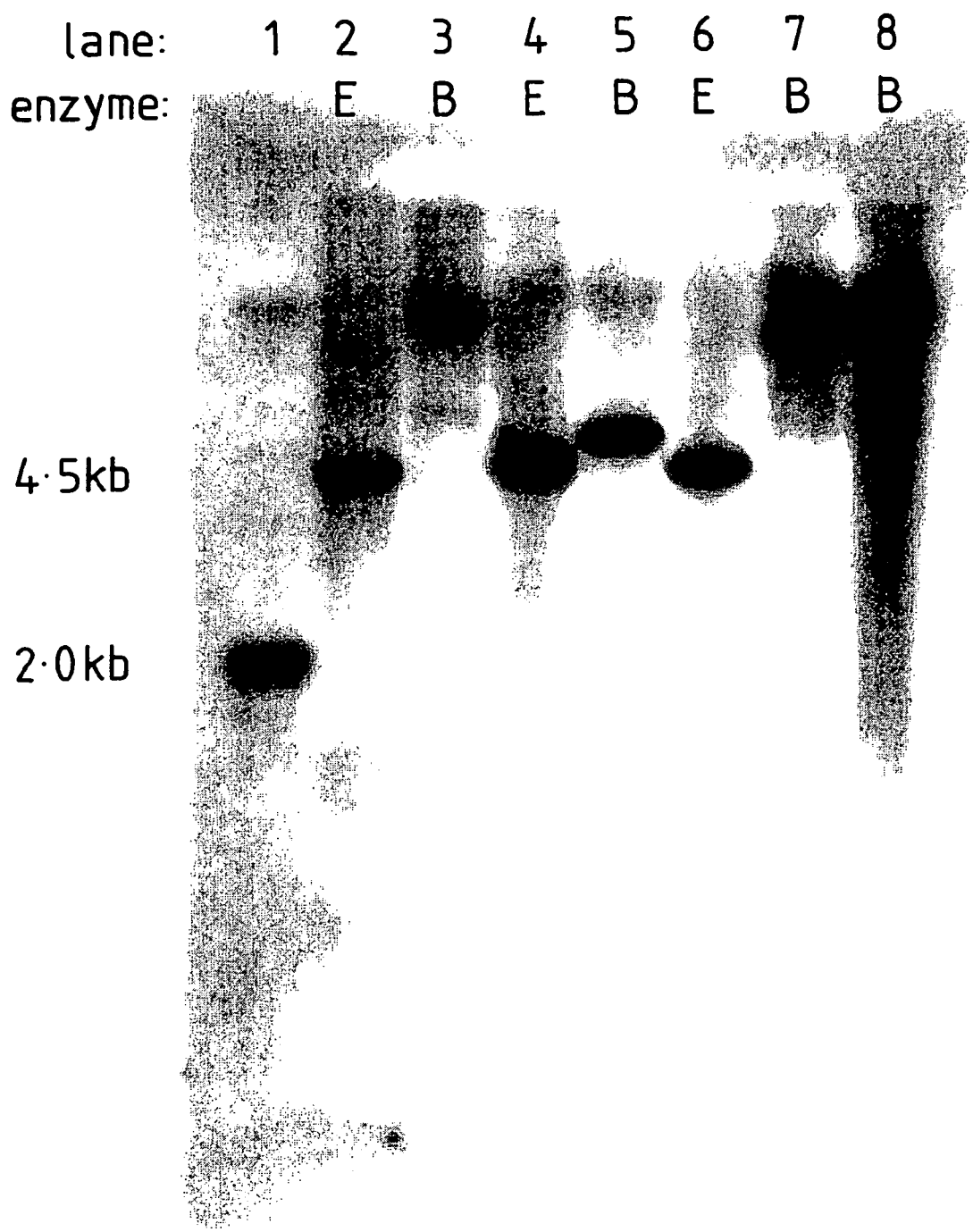
FIG. 13 is a photographic representation of Southern analysis of three T2 homozygous independent tobacco transgenic lines (3-4, 7-3 and 10-3) containing pGEL-1 fused to the GUS gene, and one T2 homozygous tobacco transgenic line (5-2) containing the CaMV 35S promoter fused to the GUS gene. Genomic DNA was digested with EcoRI (E) or BamHI (B) restriction enzymes. A $^{32}$P-labelled DNA fragment containing the full GUS gene and Nos terminator was used as a probe. Lane 1 contained size markers. Lanes 2 and 3: line 3-4; lanes 4 and 5: line 7-3; lanes 6 and 7: line 10-3; lane 8: line 5-2.

These results are shown in FIG. 13.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Abedinia et al. *Aust. J. Plant Physiol.* 24: 133-141, 1977.
Ausubel et al. In. Current Protocols in Molecular Biology. 1987. Wiley Interscience (ISBN 047 150338)
Botella et al. *Plant Mol. Biol.* 20:425-436, 1992.
Botella et al. *Proc. Natl. Acad. Sci. USA* 92:1595-1598, 1995.
Franks and Birch. *Aust. J. Plant Physiol.* 18: 471-480, 1991
Frier and McMullen. *Plant Cell Report.* 8: 586-589, 1990.
Frier et al. *Plant Cell Reports.* 11: 323-328, 1992.
Gambourg et al. *Experimental Cell Research,* 50: 151-158, 1968.
Garfinkel and Nester. *Journal of Bacteriology* 144: 732-743, 1980.
Gonsalves et al. International Symposium on Biotechnology of Tropical and Subtropical Species, 29 Sep.-3 Oct., 1997, Brisbane, Australia, p. 71.
Hajdukiewicz et al. *Plant Mol. Biol.* 25:989-994, 1994.
Hoekema et al. *Nature* 303: 179-180, 1983.
Jannsen and Gerdner. *Plant Molecular Biology* 14: 61-72, 1989.
Jefferson. *Plant. Mol. Biol. Reporter* 5(4): 387-405, 1987.
Jefferson. *Plant. Mol. Biol. Reporter* 23: 429-435, 1996.
Karunarate et al. *Aust. J. Plant. Physiol.* 23: 429-435, 1996.
McDonnell et al. *Plant Molecular Biology Reports* 4: 380-386, 1987.
Magdalita et al. *Aust. J. Bot.* 44: 343-353, 1996.
Murashige and Skoog. *Plant Physiology* 15: 73-97, 1962.
Needleman and Wunsch *J. Mol. Biol.* 48: 443-453, 1970.
Sambrook et al. *Molecular Cloning*: A Laboratory Manual Cold Spring Harbor Laboratories, Cold Spring Harbor, N.Y., USA, 1989.
Sanger et al. *Proc. Natl. Acad. Sci. USA* 74: 5463-5467, 1977.
Selker et al. *Dev. Biol.* 153:29-43, 1992.
Schenk and Hilderbrandt. *Canadian Journal of Botany* 50: 199-204, 1972.
Svab et al. "Methods in Plant Molecule Biology: A Laboratory Course Manual" pp 55-77, Cold Spring Harbor Laboratory Press, NY, 1995.
Tingay et al. *Plant Journal.* 11: 1369-1376, 1992.

The invention claimed is:

1. An isolated nucleic acid molecule comprising a promoter which confers or enhances the ability of an operably linked structural gene or other nucleic acid to be expressed, wherein the promoter comprises any one of:
   (i) a sequence of nucleotides having the sequence of SEQ ID NO:3;
   (ii) a fragment of (i) wherein said fragment comprises residues 2298 to 2384 of SEQ ID NO:3;
   (iii) a sequence of nucleotides complementary to any one of (i) or (ii).

2. The isolated nucleic acid molecule according to claim 1, wherein the promoter comprises a fragment comprising residues 1773-2384 of SEQ ID NO:3.

3. The isolated nucleic acid molecule according to claim 1, wherein the promoter comprises a fragment comprising residues 1601-2384 of SEQ ID NO:3.

4. The isolated nucleic acid molecule according to claim 1, wherein the promoter comprises a fragment comprising residues 1357-2384 of SEQ ID NO:3.

5. The isolated nucleic acid molecule according to claim 1, wherein the promoter comprises a fragment comprising residues 1189-2384 of SEQ ID NO:3.

6. The isolated nucleic acid molecule according to claim 1, wherein the promoter comprises a fragment comprising residues 819-2384 of SEQ ID NO:3.

7. The isolated nucleic acid molecule according to claim 1, wherein the promoter comprises a fragment comprising residues 2298-2473 of SEQ ID NO:3.

8. The isolated promoter of claim 1 obtainable by the method of: (i) amplifying a region of single stranded plant genomic DNA with the primers SEQ ID NO:4 and SEQ ID NO:5;
   (ii) optionally amplifying the amplified DNA of (i) above with primers selected from SEQ ID NO:6 and SEQ ID NO:7 or SEQ ID NO:8 and SEQ ID NO:9;
   (iii) running the amplified DNA on a gel and excising the amplified DNA from the gel; and
   (iv) wherein the excised amplified DNA comprises any one of: (a) a sequence of nucleotides having the sequences of SEQ ID NO:3; (b) a fragment of (a) wherein said fragment comprises residues 2298 to 2384 of SEQ ID NO:3; and (c) a sequence of nucleotides complementary to any one of (a) or (b).

9. An isolated promoter which confers or enhances the ability of an operably linked sequence to be expressed, the operably linked sequence comprising a structural gene or other nucleic acid; wherein the promoter is obtainable by a method of isolating a genomic DNA or a portion thereof from plant cells, rendering the genomic DNA or the portion thereof single stranded and then hybridizing to the genomic DNA or the portion thereof a primer corresponding to all or a part of SEQ ID NO: 1 or a complementary form thereof and isolating the nucleic acid upstream of the primer, wherein the upstream nucleic acid is the promoter and comprises any one of:
   (i) a sequence of nucleotides having the sequence of SEQ ID NO:3;
   (ii) a fragment of (i) wherein said fragment comprises residues 2298 to 2384 of SEQ ID NO:3;
   (iii) a sequence of nucleotides complementary to any one of (i) or (ii).

10. The isolated promoter of claim 9, wherein the promoter comprises a fragment comprising residues 1773-2384 of SEQ ID NO:3.

11. The isolated promoter of claim 9, wherein the promoter comprises a fragment comprising residues 1601-2384 of SEQ ID NO:3.

12. The isolated promoter of claim 9, wherein the promoter comprises a fragment comprising residues 1357-2384 of SEQ ID NO:3.

13. The isolated promoter of claim 9, wherein the promoter comprises a fragment comprising residues 1189-2384 of SEQ ID NO:3.

14. The isolated promoter of claim 9, wherein the promoter comprises a fragment comprising residues 819-2384 of SEQ ID NO:3.

15. The isolated nucleic acid molecule according to claim 1, wherein the promoter comprises a fragment comprising residues 2016-2384 of SEQ ID NO:3.

16. The isolated promoter of claim 9, wherein the promoter comprises a fragment comprising residues 2016-2384 of SEQ ID NO:3.

17. The isolated promoter of claim 9, wherein the promoter comprises a fragment comprising residues 2298-2473 of SEQ ID NO:3.

18. A genetic construct comprising the isolated nucleic acid of claim 1 or the isolated promoter of claim 9 or 8.

19. The genetic construct of claim 18, wherein the structural gene or other nucleic acid is operably linked to said promoter.

20. A method of altering a characteristic of a plant, the method comprising:
   introducing the genetic construct of claim 19 into a cell or group of cells of the plant, wherein the structural gene or the other nucleic acid alters the plant characteristic;
   regenerating a plant or plantlet from said cell or group of cells carrying the introduced structural gene or the other nucleic acid; and
   growing or subjecting said plant or plantlet to conditions sufficient to induce the promoter operably linked to the structural gene or the other nucleic acid which then alters the plant characteristic.

21. The method of claim 20, wherein the altered plant characteristic comprises resistance to a plant pathogen, altered nutritional characteristics, expression of a plantabody, an altered biochemical pathway, altered fertility or altered flower color.

22. A transgenic plant comprising the nucleic acid molecule according to anyone of claim 1 or 15.

23. A vegetative or a reproductive portion of the transgenic plant of claim 22.

24. A cut or severed flower from the transgenic plant of claim 22.

25. A modular promoter, comprising at least one portion, wherein the at least one portion comprises anyone of:
 (i) a sequence of nucleotides having the sequence set forth in SEQ ID NO:3;
 (ii) a fragment of (i) wherein said fragment comprises residues 2298 to 2384 of SEQ ID NO:3;
 (iii) a sequence of nucleotides complementary to anyone of (i) or (ii).

* * * * *

SEQUENCE LISTING

<160> NUMBER OF SEQ ID NOS: 9

<210> SEQ ID NO 1
<211> LENGTH: 1923
<212> TYPE: DNA

<213> ORGANISM: Plant
<220> FEATURE:
<221> NAME/KEY: CDS
<222> LOCATION: (88)..(1539)

<400> SEQUENCE: 1

```
atcctctctc ccacttactt cgatttcatc aattccaata aactcaacac acttttttac      60
actccacact ctaaccacat acaccat atg ggt ttc aag gcc atg gac caa act     114
                              Met Gly Phe Lys Ala Met Asp Gln Thr
                                1               5 ccc ttg ttg tcc aag atg gct att ggg gat gga cat ggc gaa tca tcc       162
Pro Leu Leu Ser Lys Met Ala Ile Gly Asp Gly His Gly Glu Ser Ser
 10              15                  20                  25 cca tac ttt gat gga tgg aag gct tat gat caa aac ccc ttt cat ccc       210
Pro Tyr Phe Asp Gly Trp Lys Ala Tyr Asp Gln Asn Pro Phe His Pro
                 30                  35                  40 aca gat aat cct aac ggt gtt atg caa atg ggt ctt gct gag aat cag       258
Thr Asp Asn Pro Asn Gly Val Met Gln Met Gly Leu Ala Glu Asn Gln
             45                  50                  55 ctt acc tct gat ttg gtt gaa gat tgg ata ctg aac aac cct gaa gcc       306
Leu Thr Ser Asp Leu Val Glu Asp Trp Ile Leu Asn Asn Pro Glu Ala
         60                  65                  70 tcc att tgc act cca gaa gga ata aat gat ttc agg gcc ata gct aac       354
Ser Ile Cys Thr Pro Glu Gly Ile Asn Asp Phe Arg Ala Ile Ala Asn
     75                  80                  85 ttt cag gat tat cat ggt ctg gcc gag ttc aga aat gct gtg gct aaa       402
Phe Gln Asp Tyr His Gly Leu Ala Glu Phe Arg Asn Ala Val Ala Lys
 90                  95                 100                 105 ttt atg gct aga aca agg gga aac aga atc acg ttt gac cct gac cgt       450
Phe Met Ala Arg Thr Arg Gly Asn Arg Ile Thr Phe Asp Pro Asp Arg
                110                 115                 120 att gtc atg agc ggt gga gcc acc gga gca cac gaa gtc act gcc ttt       498
Ile Val Met Ser Gly Gly Ala Thr Gly Ala His Glu Val Thr Ala Phe
            125                 130                 135 tgt ttg gca gat ccc ggc gag gca ttc tta gtg ccc att ccc tat tat       546
Cys Leu Ala Asp Pro Gly Glu Ala Phe Leu Val Pro Ile Pro Tyr Tyr
        140                 145                 150 cca ggc ttt gac cgg gat ttg agg tgg aga aca gga gtt aaa ctt gtt       594
Pro Gly Phe Asp Arg Asp Leu Arg Trp Arg Thr Gly Val Lys Leu Val
    155                 160                 165 cca gtt atg tgc gat agc tca aat aat ttc gtg ttg aca aag gaa gca       642
Pro Val Met Cys Asp Ser Ser Asn Asn Phe Val Leu Thr Lys Glu Ala
170                 175                 180                 185 ttg gaa gat gcc tat gag aaa gca aga gag gat aac atc aga gta aag       690
Leu Glu Asp Ala Tyr Glu Lys Ala Arg Glu Asp Asn Ile Arg Val Lys
                190                 195                 200 ggt tta ctg atc acc aat cca tca aat cca tta ggc aca atc atg gac       738
Gly Leu Leu Ile Thr Asn Pro Ser Asn Pro Leu Gly Thr Ile Met Asp
            205                 210                 215 aga aag aca ctg aga acc gtg gtg agc ttc atc aat gag aag cgt atc       786
Arg Lys Thr Leu Arg Thr Val Val Ser Phe Ile Asn Glu Lys Arg Ile
        220                 225                 230 cac ctt gta tgt gat gaa ata tat gct gca aca gtt ttc agc caa ccc       834
His Leu Val Cys Asp Glu Ile Tyr Ala Ala Thr Val Phe Ser Gln Pro
    235                 240                 245 ggt ttc ata agc ata gct gag ata tta gag gat gaa aca gac ata gag       882
Gly Phe Ile Ser Ile Ala Glu Ile Leu Glu Asp Glu Thr Asp Ile Glu
250                 255                 260                 265 tgt gac cgc aac ctc gta cac att gtt tat agt ctt tca aag gac atg       930
Cys Asp Arg Asn Leu Val His Ile Val Tyr Ser Leu Ser Lys Asp Met
```

-continued

```
                270                 275                 280
ggg ttc cct ggc ttc aga gtc ggc atc ata tac tct tac aat gat gct      978
Gly Phe Pro Gly Phe Arg Val Gly Ile Ile Tyr Ser Tyr Asn Asp Ala
            285                 290                 295 gtg gtt aat tgt gca cgc aaa atg tca agc ttt gga ttg gtg tca aca     1026
Val Val Asn Cys Ala Arg Lys Met Ser Ser Phe Gly Leu Val Ser Thr
        300                 305                 310 cag act cag tat ctt tta gca tcg atg cta aat gat gat gag ttt gtg    1074
Gln Thr Gln Tyr Leu Leu Ala Ser Met Leu Asn Asp Asp Glu Phe Val
    315                 320                 325 gag agg ttt ctg gca gag agt gca aag agg ttg gct caa agg ttc agg    1122
Glu Arg Phe Leu Ala Glu Ser Ala Lys Arg Leu Ala Gln Arg Phe Arg
330                 335                 340                 345 gtt ttc act ggg ggg ttg gcc aaa gtt ggc ata aag tgc ttg caa agc    1170
Val Phe Thr Gly Gly Leu Ala Lys Val Gly Ile Lys Cys Leu Gln Ser
                350                 355                 360 aat gct ggt cta ttt gtg tgg atg gat tta agg caa ctt ctc aaa aag    1218
Asn Ala Gly Leu Phe Val Trp Met Asp Leu Arg Gln Leu Leu Lys Lys
            365                 370                 375 cca act ttc gac tct gaa acg gag ctt tgg aaa gtt atc att cat gaa    1266
Pro Thr Phe Asp Ser Glu Thr Glu Leu Trp Lys Val Ile Ile His Glu
        380                 385                 390 gtt aag atc aat gtt tca cct ggc tat tcc ttc cat tgc act gag cca    1314
Val Lys Ile Asn Val Ser Pro Gly Tyr Ser Phe His Cys Thr Glu Pro
    395                 400                 405 ggg tgg ttt agg gtg tgc tat gcc aac atg gat gat atg gct gtg caa    1362
Gly Trp Phe Arg Val Cys Tyr Ala Asn Met Asp Asp Met Ala Val Gln
410                 415                 420                 425 att gct ttg caa cga atc cgc aac ttt gtg ctt caa aac aag gag gtc    1410
Ile Ala Leu Gln Arg Ile Arg Asn Phe Val Leu Gln Asn Lys Glu Val
                430                 435                 440 gtg gtg tct aat aag aaa cat tgt tgg cac agt aac ttg agg ctg agc    1458
Val Val Ser Asn Lys Lys His Cys Trp His Ser Asn Leu Arg Leu Ser
            445                 450                 455 ctc aaa acc aga agg ttt gat gat atc acc atg tca cct cac tct ccc    1506
Leu Lys Thr Arg Arg Phe Asp Asp Ile Thr Met Ser Pro His Ser Pro
        460                 465                 470 cta cct cag tca cct atg gtt aaa gcc aca aat tgagtttgca tattcctctg  1559
Leu Pro Gln Ser Pro Met Val Lys Ala Thr Asn
    475                 480 aatcgtttag aagaagtaac tgatatgtga agattacttg gttctttat ttgttatttt    1619 gagaaggtac ataagtgctg gatttgttct ttggaacagc aataacagga aattcctgat    1679
gttgttttgt gatcggcatc acaatccagt gtcctacaag ttgtgctgct tcatgcacgc    1739
cccttcaatc ttaggggcat tttttctttt ttcacttacc aaaggttcaa ggtgaaaaaa    1799
gtttatagag tctgtaatgt tattggttta tcagaagagt ccaaaagatg tctgtaatct    1859
gctactgaaa ttgtaacttt caattatgaa taaattgtta ataaggtct tcaaattcat    1919 ttcc                                                                 1923

<210> SEQ ID NO 2
<211> LENGTH: 484
<212> TYPE: PRT
<213> ORGANISM: Plant

<400> SEQUENCE: 2

Met Gly Phe Lys Ala Met Asp Gln Thr Pro Leu Leu Ser Lys Met Ala
 1               5                  10                  15
```

```
Ile Gly Asp Gly His Gly Glu Ser Ser Pro Tyr Phe Asp Gly Trp Lys
            20                  25                  30

Ala Tyr Asp Gln Asn Pro Phe His Pro Thr Asp Asn Pro Asn Gly Val
        35                  40                  45

Met Gln Met Gly Leu Ala Glu Asn Gln Leu Thr Ser Asp Leu Val Glu
    50                  55                  60

Asp Trp Ile Leu Asn Asn Pro Glu Ala Ser Ile Cys Thr Pro Glu Gly
65                  70                  75                  80

Ile Asn Asp Phe Arg Ala Ile Ala Asn Phe Gln Asp Tyr His Gly Leu
                85                  90                  95

Ala Glu Phe Arg Asn Ala Val Ala Lys Phe Met Ala Arg Thr Arg Gly
            100                 105                 110

Asn Arg Ile Thr Phe Asp Pro Asp Arg Ile Val Met Ser Gly Gly Ala
        115                 120                 125

Thr Gly Ala His Glu Val Thr Ala Phe Cys Leu Ala Asp Pro Gly Glu
    130                 135                 140

Ala Phe Leu Val Pro Ile Pro Tyr Tyr Pro Gly Phe Asp Arg Asp Leu
145                 150                 155                 160

Arg Trp Arg Thr Gly Val Lys Leu Val Pro Val Met Cys Asp Ser Ser
                165                 170                 175

Asn Asn Phe Val Leu Thr Lys Glu Ala Leu Glu Asp Ala Tyr Glu Lys
            180                 185                 190

Ala Arg Glu Asp Asn Ile Arg Val Lys Gly Leu Leu Ile Thr Asn Pro
        195                 200                 205

Ser Asn Pro Leu Gly Thr Ile Met Asp Arg Lys Thr Leu Arg Thr Val
    210                 215                 220

Val Ser Phe Ile Asn Glu Lys Arg Ile His Leu Val Cys Asp Glu Ile
225                 230                 235                 240

Tyr Ala Ala Thr Val Phe Ser Gln Pro Gly Phe Ile Ser Ile Ala Glu
                245                 250                 255

Ile Leu Glu Asp Glu Thr Asp Ile Glu Cys Asp Arg Asn Leu Val His
            260                 265                 270

Ile Val Tyr Ser Leu Ser Lys Asp Met Gly Phe Pro Gly Phe Arg Val
        275                 280                 285

Gly Ile Ile Tyr Ser Tyr Asn Asp Ala Val Val Asn Cys Ala Arg Lys
    290                 295                 300

Met Ser Ser Phe Gly Leu Val Ser Thr Gln Thr Gln Tyr Leu Leu Ala
305                 310                 315                 320

Ser Met Leu Asn Asp Asp Glu Phe Val Glu Arg Phe Leu Ala Glu Ser
                325                 330                 335

Ala Lys Arg Leu Ala Gln Arg Phe Arg Val Phe Thr Gly Gly Leu Ala
            340                 345                 350

Lys Val Gly Ile Lys Cys Leu Gln Ser Asn Ala Gly Leu Phe Val Trp
        355                 360                 365

Met Asp Leu Arg Gln Leu Leu Lys Lys Pro Thr Phe Asp Ser Glu Thr
    370                 375                 380

Glu Leu Trp Lys Val Ile Ile His Glu Val Lys Ile Asn Val Ser Pro
385                 390                 395                 400

Gly Tyr Ser Phe His Cys Thr Glu Pro Gly Trp Phe Arg Val Cys Tyr
                405                 410                 415

Ala Asn Met Asp Asp Met Ala Val Gln Ile Ala Leu Gln Arg Ile Arg
            420                 425                 430

Asn Phe Val Leu Gln Asn Lys Glu Val Val Val Ser Asn Lys Lys His
```

```
                435                 440                 445
Cys Trp His Ser Asn Leu Arg Leu Ser Leu Lys Thr Arg Arg Phe Asp
    450                 455                 460

Asp Ile Thr Met Ser Pro His Ser Pro Leu Pro Gln Ser Pro Met Val
465                 470                 475                 480

Lys Ala Thr Asn

<210> SEQ ID NO 3
<211> LENGTH: 2474
<212> TYPE: DNA
<213> ORGANISM: Plant

<400> SEQUENCE: 3
ttacagatac acagaatcag acgacacatc tactttaata acagaaaaat aataagtgtc      60
ggagattatg gtacgacaag atgaaatgtt tttatatggt tgagattatt ttggtctgtt     120
gttggaagtt tcacgaatca tgattttgat tttacgtatt aaaaaatgaa aagttgaatc     180
atgcatttta tctagaagct gggaactgaa ccaaaaaaat agccagttga caactgcag      240 tatttgtagg cgtattcatt tctcctttcc tacaataatc cttggttgct ctttatcgga     300
aaaaaaccaa aagcaatagc tactctgtaa ggtcctcgat tgccgacaag aacatcacat     360
gcgtgctgtc gaagaacaca taattttgag gttgaagctc acgtgcgagt tttgcatatt     420
tttaggttat gtgtacacgt atggagtgag ttccgcgtat atagtgtagg tagttgagtg     480
gctgagtagc gagtgaatca ggtaacacta tcttttcaag ccacctaatt aagggattta     540
atgttcatgc aactgttctt cgctaactaa ggccccactt acctttataa tattctctct     600
aactccgggc ttttggtaag tacaactttt ctactcttat ttaatggagg gattattttt     660
tccatatacc aattaattta ttttttaatt tatgcatttt gatcttatat taaaacaatt     720
atggtatgga ttaagtcgta tatcggtgac aattgaagtt ttcctcaagt ttagccattt     780
ttatgaaatt aaacttaatc actactatta ggtaaattca tatgtatcat taacaatttc     840
aatgtgagtt caattttacc caagatttga agttgttgt caacttctgt taactaaagt      900
tgtattataa ggttgacgac tttaacctaa atctattttg aattgaaggg gttgatgact     960
tcagctttaa ataattcaa ctaaagttct agactacatt ggagatttta gtgttcataa     1020
aattttagaa aaaggctgag ttaaagttat gaaaaagatt ggtgactatt caattaatta     1080
gttgtgaatt gatgacaaat atttcatgag cataaccaat cagagaaata ccacctcgac     1140
cgactacaac aatctcaatg ttaattaatg aagcattgta gtataaggag tctagaataa     1200
atttcttaaa tattagagga aaactatttt taaaaaatta caagaaaagt ttgatctata     1260
acctctttaa actttaaatt atctaacaat tttcttatga ctcacattgt gttgataggg     1320
tgattttgtc aaaatatatg tctattttat actagtatga tttgtctgcg aattatatat     1380
agtattaact tggagaaatg attgcctaat aagttataaa aaggagaaa atatttattc      1440 ataaaaaaaa tacacttaaa taagtaacaa taataaaaaa cattatataa gagattaaga     1500
taatttaata agtattgaat gtagaataat ttttatttat aaatttgaac taaaatattc     1560
aaataatatt caaagtaaat aatagatata attcatcatt caatacgagt aattcaatct     1620
attataatca tatattagat aaatatacaa atatttgtta aattttacat tattatatta     1680
ctaaatatat attaatttct ttgaatatct tttatacaag taggtagact agaagaatta     1740
tcttatctcc cgtatatttg tagatgttaa atgtaacggg cttagactga tgttttgta      1800 ttatattatt tataaatcca ttagagattt aagttaatgt ctctctttga ttttaacatg     1860
```

-continued

```
gttctaaaaa ttaggtttaa tcattgcgtc tcaatgaac ccatgctata tgttttaaag    1920
ttttttgttt tttgacaatg ttttttattt ctgagattgc tcttaggatt gaaattatgt    1980
ttgatactag aaaacgaaga agtagagagt agtgtataca cgtgtaaaaa ataatagttg    2040
tgggaactta agttggattt gaatactagg acgaggctgg aagggtttcc actaagttga    2100
caaaaattat tacaagtggc aactagctag gtctcacaaa gtattactaa ttaatagtgg    2160
gtctgtctgc ataccaactc ttgcctaatt tcaaacacc gcattctctc ttcttctctc    2220
cttcttcctc tggaaacttc atcgatgtgg acttctgtct ctcaaaagtc aagctcaatt    2280
tatccaatgc attataaata cacactctcc ctcccttcta ttcttcattg catcacattt    2340
cctctataaa ttactcacac cttattccta acttcatttc aacatcctct ctcccactta    2400
cttcgatttc atcaattcca ataaactcaa cacactttttt tacactccac actctaacca    2460
catacaccat atgg                                                       2474
```

<210> SEQ ID NO 4
<211> LENGTH: 29
<212> TYPE: DNA
<213> ORGANISM: Plant

<400> SEQUENCE: 4

```
gcggatccat cttggacaac aagggagtt                                         29
```

<210> SEQ ID NO 5
<211> LENGTH: 30
<212> TYPE: DNA
<213> ORGANISM: Plant

<400> SEQUENCE: 5

```
taggatccag aaagacactg agaaccgtgg                                        30
```

<210> SEQ ID NO 6
<211> LENGTH: 29
<212> TYPE: DNA
<213> ORGANISM: Plant

<400> SEQUENCE: 6

```
acggatccgg tgtatgtggt tagagtgtg                                         29
```

<210> SEQ ID NO 7
<211> LENGTH: 29
<212> TYPE: DNA
<213> ORGANISM: Plant

<400> SEQUENCE: 7

```
caggatccag acatagagtg tgaccgcaa                                         29
```

<210> SEQ ID NO 8
<211> LENGTH: 59
<212> TYPE: DNA
<213> ORGANISM: Plant

<400> SEQUENCE: 8

```
atcgatcata tgagctctag acccgggctg caggatccgg tgtatgtggt tagagtgtg       59
```

```
<210> SEQ ID NO 9
<211> LENGTH: 57
<212> TYPE: DNA
<213> ORGANISM: Plant

<400> SEQUENCE: 9
ccgcggagat ctatcgatct cgagaattca agcttcagac atagagtgtg accgcaa       57
```